United States Patent
Ivry et al.

(10) Patent No.: US 11,726,091 B2
(45) Date of Patent: Aug. 15, 2023

(54) COMPOSITIONS AND METHODS OF DIAGNOSING PANCREATIC CANCER

(71) Applicant: THE REGENTS OF THE UNIVERSITY OF CALIFORNIA, Oakland, CA (US)

(72) Inventors: Sam L. Ivry, San Francisco, CA (US); Anthony J. O'Donoghue, La Jolla, CA (US); Kimberly Kirkwood, San Francisco, CA (US); Charles S. Craik, San Francisco, CA (US)

(73) Assignee: THE REGENTS OF THE UNIVERSITY OF CALIFORNIA

( * ) Notice: Subject to any disclaimer, the term of this patent is extended or adjusted under 35 U.S.C. 154(b) by 328 days.

(21) Appl. No.: 16/500,752

(22) PCT Filed: Apr. 3, 2018

(86) PCT No.: PCT/US2018/025966
§ 371 (c)(1),
(2) Date: Oct. 3, 2019

(87) PCT Pub. No.: WO2018/187385
PCT Pub. Date: Oct. 11, 2018

(65) Prior Publication Data
US 2020/0081011 A1 Mar. 12, 2020

Related U.S. Application Data

(60) Provisional application No. 62/481,088, filed on Apr. 3, 2017.

(51) Int. Cl.
*G01N 33/574* (2006.01)
*G01N 33/68* (2006.01)
*C12Q 1/37* (2006.01)

(52) U.S. Cl.
CPC ......... *G01N 33/57438* (2013.01); *C12Q 1/37* (2013.01); *G01N 33/6848* (2013.01); *G01N 2333/96416* (2013.01)

(58) Field of Classification Search
CPC ......... G01N 33/57438; G01N 33/6848; G01N 2333/96416; G01N 33/57473; C12Q 1/37; C12N 9/6478
See application file for complete search history.

(56) References Cited

U.S. PATENT DOCUMENTS

| 2013/0251640 A1 | 9/2013 | Tung et al. |
| 2014/0227188 A1* | 8/2014 | Tung ............... A61K 45/06 424/9.6 |
| 2016/0324942 A1 | 11/2016 | Lester et al. |
| 2017/0089907 A1 | 3/2017 | Finkelstein et al. |

FOREIGN PATENT DOCUMENTS

| WO | WO-2014/144572 A2 | 9/2014 |
| WO | WO-2018/187385 A1 | 10/2018 |

OTHER PUBLICATIONS

Azuma et al., Int. J. Cancer., 1996, vol. 67, p. 492-497.*
Auf dem Keller U, Schilling O. Proteomic techniques and activity-based probes for the system-wide study of proteolysis. Biochimie. Nov. 2010;92(11):1705-14. doi: 10.1016/j.biochi.2010.04.027. Epub May 20, 2010. PMID: 20493233.*
Morana G, Guarise A. Cystic tumors of the pancreas. Cancer Imaging. Jul. 13, 2006;6(1):60-71. doi: 10.1102/1470-7330.2006. 0012. PMID: 16861136; PMCID: PMC1693784.*
Moris, M., et al., Association between advances in high-resolution cross-section imaging technologies and increase in prevalence of pancreatic cysts from 2005 to 2014, Clin. Gastroenterol. Hepatol., 2016, 14:585-593.
Lee, K. S., et al., Prevalence of incidental pancreatic cysts in the adult population on MR imaging, Am. J. Gastroenterol., 2010, 105:2079-2084.
Laffan, T. A., et al., Prevalence of unsuspected pancreatic cysts on MDCT, Am. J. Roentgenol., 2008, 191:802-807.
Volkan Adsay, N., Cystic lesions of the pancreas, Mod. Pathol., 2007, 20:S71-S93.
Matthaei, H., et al., Cystic precursors to invasive pancreatic cancer, Nat. Rev. Gastroenterol. Hepatol., 2011, 8(3):141-150.
Crippa, S., et al., Mucin-producing neoplasms of the pancreas: An analysis of distinguishing clinical and epidemiologic characteristics, Clin. Gastroenterol. Hepatol., 2011, 8:213-219.
Jang, K.-T., et al., Clinicopathologic characteristics of 29 invasive carcinomas arising in 178 pancreatic mucinous cystic neoplasms with ovarian-type stroma: Implications for management and prognosis, Am. J. Surg. Pathol., 2015, 39(2):179-187.
Tanaka, M., et al., International consensus guidelines 2012 for the management of IPMN and MCN of the pancreas, Pancreatology, 2012, 12:183-197 (Abstract only).
Correa-Gallego, C, et al., Incidental pancreatic cysts: Do we really know what we are watching? Pancreatology, 2010, 10:144-150.
Parra-Herran, C. E., et al., Cystic lesions of the pancreas: Clinical and pathologic review of cases in a five year period, J. Pancreas, 2010, 11(4):358-364.
Quan, S. Y., et al., Predictive factors for surgery among patients with pancreatic cysts in the absence of high-risk features for malignancy, J. Gastrointest. Surg., 2015, 19:1101-1105 (Abstract only).
Cho, C. S., et al., Preoperative classification of pancreatic cystic neoplasms: The clinical significance of diagnostic inaccuracy, Ann. Surg. Oncol., 2013, 20(9):3112-3119.

(Continued)

*Primary Examiner* — Kade Ariani
(74) *Attorney, Agent, or Firm* — The Belles Group, P.C.

(57) ABSTRACT

The present disclosure relates generally to detection of molecular biomarkers in a sample or diagnosis of a subject based upon detection or quantification of molecular biomarkers in a sample, specifically to the identification and use of biomarkers for pancreatic cysts.

8 Claims, 21 Drawing Sheets

Figure 1A:
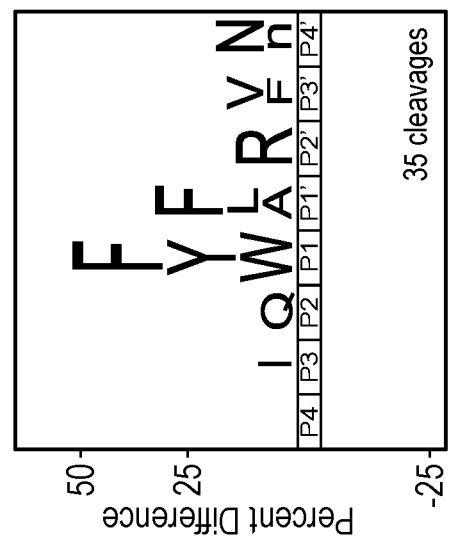

Specification includes a Sequence Listing.

(56) References Cited

OTHER PUBLICATIONS

Park, W. G., et al., Diagnostic performance of cyst fluid carcinoembryonic antigen and amylase in histologically confirmed pancreatic cysts, Pancreas, 2011, 40(1):42-45.
Ngamruengphong, S., et al., Cyst carcinoembryonic antigen in differentiating pancreatic cysts: A meta-analysis, Dig. Liver Dis., 2013, 45(11):920-926 (Abstract only).
Almoguera, C., et al., Most Human Carcinomas of the Exocrine Contain Mutant c-K-ras Genes, Cell, 1988, 53:549-554.
Hezel, A. F., et al., Genetics and biology of pancreatic ductal adenocarcinoma, Genes Dev., 2006, 20:1218-1249.
Khalid, A., et al., Pancreatic cyst fluid DNA analysis in evaluating pancreatic cysts: A report of the PANDA study, Gastrointest. Endosc., 2009, 69:1095-1102 (Abstract only).
Wu, J., et al., Recurrent GNAS mutations define an unexpected pathway for pancreatic cyst development, Sci. Transl. Med., 2011, 3(92):92ra66.
Hata, T., et al., Cyst fluid telomerase activity predicts the histologic grade of cystic neoplasms of the pancreas, Clin. Cancer Res., 2016, 20:5141-5151.
Zikos, T., et al., Cyst fluid glucose is rapidly feasible and accurate in diagnosing mucinous pancreatic cysts, Am. J. Gastroenterol., 2015, 110:909-914.
Yip-Schneider, M. T., et al., Vascular endothelial growth factor, a novel and highly accurate pancreatic fluid biomarker for serous pancreatic cysts, J. Am. Coll. Surg., 2014, 218(4):608-617.
Cao, Z., et al., Specific glycoforms of MUC5AC and endorepellin accurately distinguish mucinous from nonmucinous pancreatic cysts, Mol. Cell Proteomics, 2013, 12:2724-2734.
Maker, A. V., et al., Cyst fluid interleukin-1β (IL1β) levels predict the risk of carcinoma in intraductal papillary mucinous neoplasms of the pancreas, Clin. Cancer Res., 2011, 17(6):1502-1508.
Kessenbrock, K., et al., Matrix metalloproteinases: Regulators of the tumor microenvironment, Cell, 2010, 141(1):52-67.
Sevenich, L., et al., Pericellular proteolysis in cancer, Genes Dev., 2014, 28:2331-2347.
Sobotič, B., et al., Proteomic identification of cysteine cathepsin substrates shed from the surface of cancer cells, Mol. Cell Proteomics, 2015, 14:2213-2228.
Joyce, J. A., et al., Cathepsin cysteine proteases are effectors of invasive growth and angiogenesis during multistage tumorigenesis, Cancer Cell, 2004, 5:443-453.
Gocheva, V., et al., Distinct roles for cysteine cathepsin genes in multistage tumorigenesis, Genes Dev., 2006, 20:543-556.
Terris, B., et al., Characterization of gene expression profiles in intraductal papillary-mucinous tumors of the pancreas, Am. J. Pathol., 2002, 160(5):1745-1754.
Sato, N., et al., Gene expression profiling identifies genes associated with invasive intraductal papillary mucinous neoplasms of the pancreas, Am. J. Pathol., 2004, 164(3):903-914.
Fukushima, N., et al., Characterization of gene expression in mucinous cystic neoplasms of the pancreas using oligonucleotide microarrays, Oncogene, 2004, 23:9042-9051.
Ke, E., et al., Proteomic analyses of pancreatic cyst fluids, Pancreas, 2009, 38(2):e33-e42.
Räty, S., et al., Cyst fluid SPINK1 may help to differentiate benign and potentially malignant cystic pancreatic lesions, Pancreatology, 2013, 13:530-533 (Abstract only).
O'Donoghue, A. J., et al., Global identification of peptidase specificity by multiplex substrate profiling, Nat. Methods, 2012, 9(11):1095-1100.
Chalkley, R.J., et al., In-depth analysis of tandem mass spectrometry data from disparate instrument types, Mol. Cell Proteomics, 2008, 7:2386-2398.
Schilling, B., et al., Platform-independent and label-free quantitation of proteomic data using MS1 extracted ion chromatograms in skyline: Application to protein acetylation and phosphorylation, Mol. Cell Proteomics, 2012, 11:202-214.
Colaert, N., et al., Improved visualization of protein consensus sequences by iceLogo, Nat. Methods, 2009, 6:786-787.
Winter, M. B., et al., Global identification of biofilm-specific proteolysis in Candida albicans, MBio, 2016, 7(5):e01514-16, 13 pages.
O'Donoghue, A. J., et al., Destructin-1 is a collagen-degrading endopeptidase secreted by Pseudogymnoascus destructans, the causative agent of white-nose syndrome, PNAS, 2015, 112(24):7478-7483.
Small, J. L., et al., Substrate specificity of MarP, a periplasmic protease required for resistance to acid and oxidative stress in Mycobacterium tuberculosis, J. Biol. Chem., 2013, 288(18):12489-12499.
Impens, F., et al., A quantitative proteomics design for systematic identification of protease cleavage events, Mol. Cell Proteomics, 2010, 9:2327-2333.
O'Donoghue, A. J., et al., Procathepsin E is highly abundant but minimally active in pancreatic ductal adenocarcinoma tumors, Biol. Chem., 2016, 397(9):871-881.
Dunn, B. M., Structure and mechanism of the pepsin-like family of aspartic peptidases, Chem. Rev., 2002, 102:4431-4458 (First page only).
Von Figura, G., et al., The chromatin regulator Brg1 suppresses formation of intraductal papillary mucinous neoplasm and pancreatic ductal adenocarcinoma, Nat. Cell Biol., 2014, 16(3):255-267.
Abd-Elgaliel, W. R., et al., Selective detection of cathepsin E proteolytic activity, Biochim. Biophys. Acta, 2010, 1800(9):1002-1008.
Brugge, W. R., et al., Diagnosis of pancreatic cystic neoplasms: A report of the cooperative pancreatic cyst study, Gastroenterology, 2004, 126:1330-1336.
Kremer Hovinga, J. A., et al., Measurement of ADAMTS-13 activity in plasma by the FRETS-VWF73 assay: Comparison with other assay methods, J. Thromb. Haemost., 2006, 4:1146-1148.
Moll, S., et al., Monitoring warfarin therapy in patients with lupus anticoagulants, Ann. Intern. Med., 1997, 127:177-185 (Abstract only).
Prasad, N. B., et al., Gene expression profiles in pancreatic intraepithelial neoplasia reflect the effects of Hedgehog Signaling on Pancreatic Ductal Epithelial Cells, Cancer Res., 2005, 65(5):1619-1626.
Roy, N., et al., Brg1 promotes both tumor-suppressive and oncogenic activities at distinct stages of pancreatic cancer formation, Genes Dev., 2015, 29:658-671.
Sun, C., et al., Time resolved single-step protease activity quantification using nanoplasmonic resonator sensors, ACS Nano., 2010, 4(2):978-984.
Kokame, K., et al., FRETS-VWF73, a first fluorogenic substrate for ADAMTS13 assay, Brit. J. Haem., 2005, 129(1):93-100.
Kremer Hovinga, J. A., et al., Measurement of ADAMTS-13 activity in plasma by the FRETS-VWF73 assay: Comparison with other assay methods, J. Thrombo. Haem., 2006, 4(5):1146-1148.
Chiang, L., et al., Purification and properties of porcine gastricsin, J. Biol. Chem., 1967, 242(13):3098-3102.
Friedman, M., Applications of the ninhydrin reaction for analysis of amino acids, peptides, and proteins to agricultural and biomedical sciences, J. Agric. Food. Chem., 2004, 52(3):385-406 (Abstract only).
Kusebauch, U., et al., Human SRMAtlas: A resource of targeted assays to quantify the complete human proteome, Cell, 2016, 166(3):766-778.
Anderson, M., et al., 216 Molecular markers from EUS fine needle specimens can differentiate pancreatic neoplasia requiring surgery from chronic pancreatitis and other benign conditions of the pancreas, Gastrointestinal Endoscopy, 2005, 61(5):AB78.
Uno, K., et al., Clinical significance of cathepsin E in pancreatic juice in the diagnosis of pancreatic ductal adenocarcinoma, Journal of Gastroenterology and Hepatology, 2000, 15:1333-1338.
Ivry, S. L., Global protease activity profiling for pancreatic cancer diagnosis and treatment, Doctoral dissertation, UCSF, 2018.
International Search Report and Written Opinion of the International Searching Authority for PCT/US2018/025966 dated Aug. 24, 2018.

(56) References Cited

OTHER PUBLICATIONS

International Preliminary Report on Patentability for PCT/US2018/025966 dated Oct. 8, 2019.

* cited by examiner

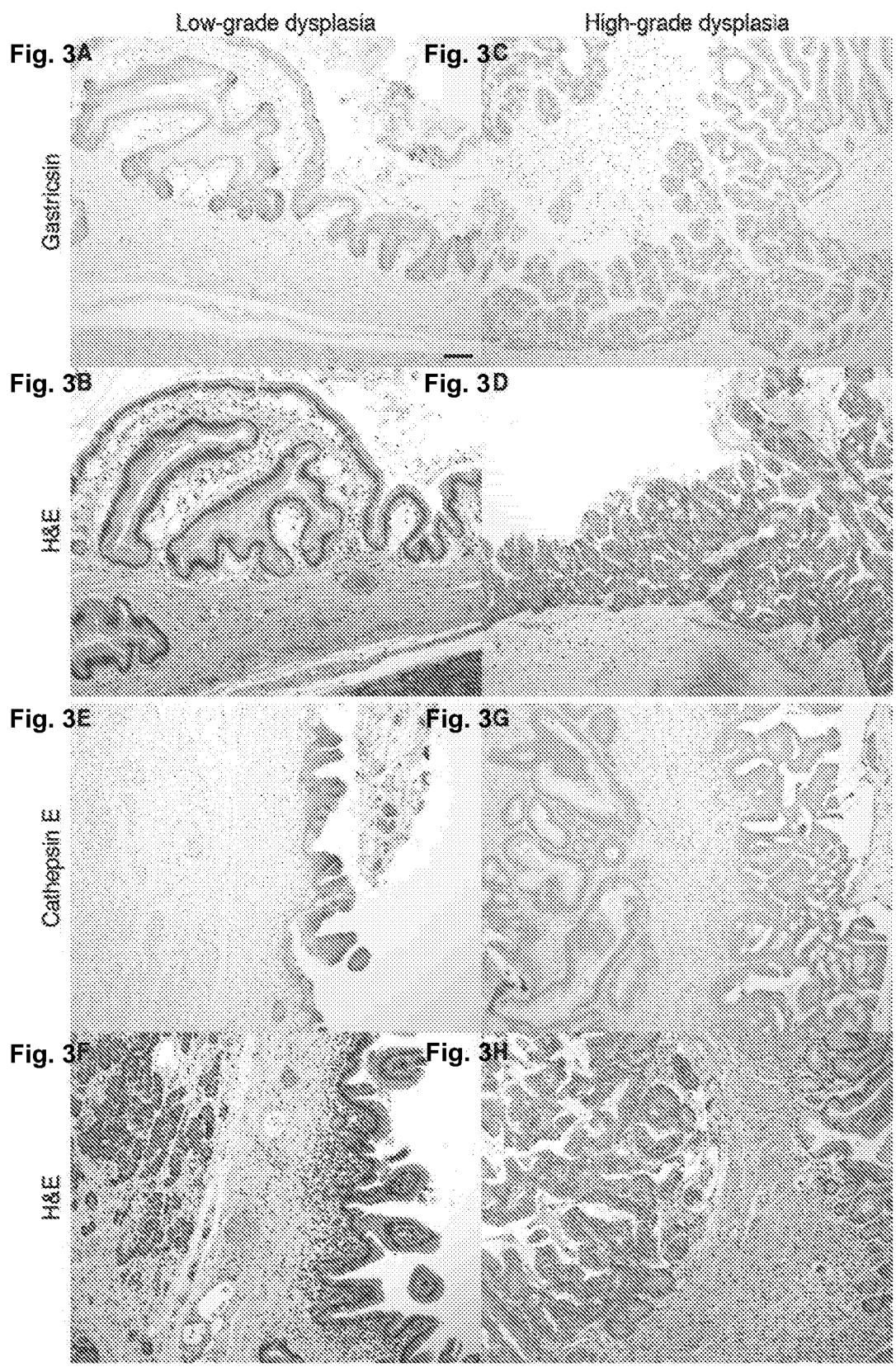

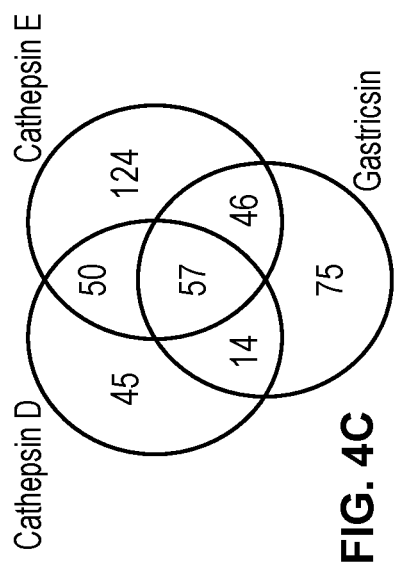
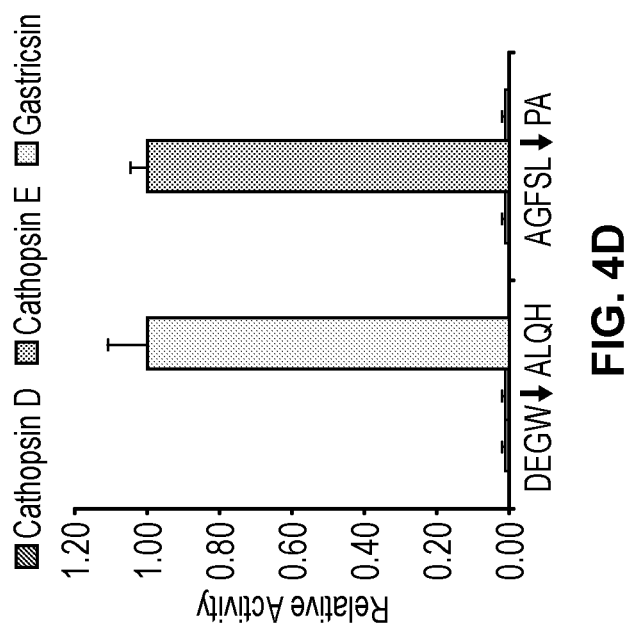
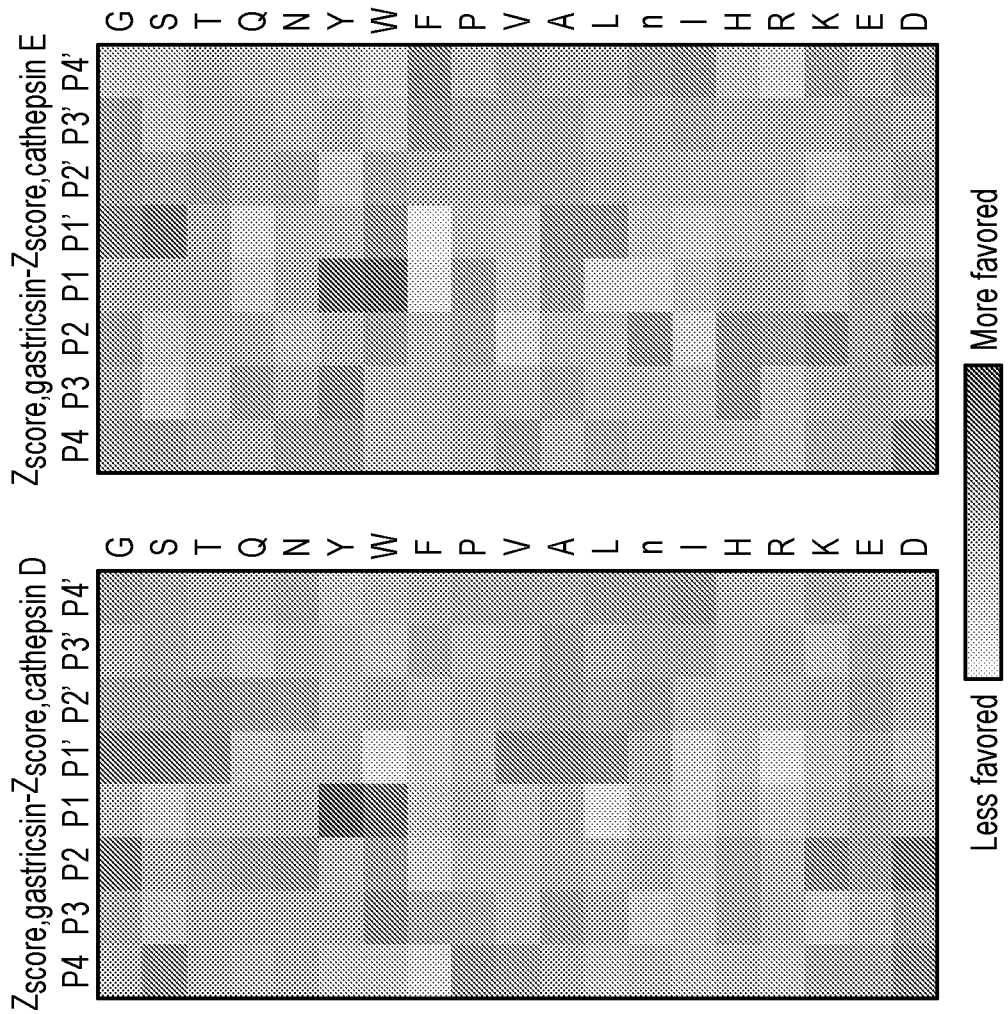
FIG. 4C
FIG. 4D
FIG. 4B

COMPOSITIONS AND METHODS OF DIAGNOSING PANCREATIC CANCER

CROSS-REFERENCE TO RELATED APPLICATIONS

The present application is a National Stage application filed under 35 U.S.C. § 371 of International Application No. PCT/US2018/025966, filed on Apr. 3, 2018, which claims priority to U.S. Provisional Patent Application No. 62/481,088, filed Apr. 3, 2017, the contents of each of which are hereby incorporated by reference in its entirety.

STATEMENT REGARDING FEDERALLY SPONSORED RESEARCH

This invention was made with government support under grant numbers R21 CA186077, TR000004, P41 CA196276, and R21 CA185689 awarded by the National Institutes of Health. The United States government has certain rights in this invention.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 37944_0006U2_SL. The size of the text file is 55 KB and the text file was created on Oct. 3, 2019.

TECHNOLOGY FIELD

The present disclosure relates generally to detection of protease activity in a sample, or diagnosis of a subject based upon detection or quantification of levels or activity of proteases in a sample, specifically to identify and use of molecular biomarkers for pancreatic cysts.

BACKGROUND

The detection of pancreatic cysts has increased dramatically due to the rising use of high-resolution abdominal imaging. Pancreatic cysts are incidentally detected in 13-45% of patients evaluated by magnetic resonance imaging and 2% of patients evaluated by computed tomography (1-3). The most frequently detected pancreatic cysts include intraductal papillary mucinous neoplasms (IPMNs), mucinous cystic neoplasms (MCNs), pseudocysts, and serous cystadenomas (SCAs) (4). Both IPMNs and MCNs, which are collectively referred to as mucinous cysts, may develop foci of high-grade dysplasia or cancer (5). At the time of resection, ~30% of IPMNs and ~15% of MCNs contain invasive cancer (6,7). Pseudocysts and SCAs, which are both nonmucinous, rarely undergo malignant degeneration and are considered benign lesions that typically do not require resection or continued surveillance. Clinical decision making for pancreatic cysts relies largely on radiographic and clinical features, augmented by analysis of cyst fluid collected by endoscopic ultrasound with fine needle need aspiration (EUS-FNA) (8). Unfortunately, with current clinical guidelines, distinguishing nonmucinous from mucinous cysts remains a challenge. The preoperative diagnosis of mucinous cysts is incorrect in up to 30% of cases and benign cysts are often resected, exposing patients to an unnecessary risk for morbidity (9-12).

As abdominal imaging remains unable to accurately differentiate pancreatic cyst types, there has been considerable effort towards developing improved diagnostic biomarkers. Most of these biomarkers utilize cyst fluid collected by EUS-FNA. Carcinoembryonic antigen (CEA) is the most widely investigated biomarker and is 60-80% accurate for differentiating mucinous from nonmucinous cysts (13,14). KRAS mutations occur in more than 90% of pancreatic cancers and are frequently observed in mucinous cysts (15,16). Analysis of cyst fluid DNA revealed that KRAS mutations are 100% specific, but only 50% sensitive for diagnosing a mucinous cyst (17). Similarly, analysis of mutations in the oncogene GNAS are specific for diagnosing IPMNs, but suffer from low sensitivity (18). A variety of other cyst fluid biomarkers have also been explored (19-23); however, CEA remains the only widely applied molecular biomarker for differentiating mucinous from nonmucinous cysts. The immunoenzymatic assay used for CEA analysis requires at least 500 µL of cyst fluid collected by endoscopic ultrasound-guided fine needle aspiration biopsy (EUS-FNA). However, many cyst fluid samples are low volume, limiting the use of CEA analysis.

Proteases mediate a variety of critical processes in cancer, including invasion of the basement membrane via cleavage of extracellular matrix proteins and promotion of oncogenic signaling pathways through activation of growth factors and receptor tyrosine kinases (24,25). In pancreatic cancer, members of the cathepsin family of endolysosomal proteases are upregulated and found extracellularly. Aberrant secretion leads to cleavage of extracellular substrates, driving increased cellular invasion (26). Either genetic deletion or pharmacological inhibition of cysteine cathepsin activity decreases tumor progression and invasion (27,28). Gene expression profiling studies of IPMNs and MCNs indicate overexpression of a range of proteases (29-31). Furthermore, analysis of protein expression in cyst fluid showed substantial differences in the abundance of pancreatic proteases and their cognate inhibitors between cyst types. The serine protease inhibitor SPINK1 was recently investigated as a biomarker for differentiating benign from malignant cysts (32,33). Collectively, these results suggest that there may be altered levels of proteolytic activity between mucinous and nonmucinous cysts and that these differences could be exploited to distinguish the type of lesion and its associated malignant potential.

SUMMARY OF EMBODIMENTS

The present disclosure relates to a method of diagnosing a subject with a benign, pre-malignant, or malignant growth of the pancreas. In one aspect, the method comprises detecting the presence, absence, and/or quantity of at least one aspartyl protease or functional fragment thereof in a sample.

The present disclosure also relates to a method of diagnosing a subject with a pancreatic ductal adenocarcinoma (PDA). In one aspect, the method comprises detecting the presence, absence, and/or quantity of at least one aspartyl protease or functional fragment thereof in a sample.

The present disclosure also relates to a method of diagnosing a subject with an intraductal papillary mucinous neoplasm (IPMN). In one aspect, the method comprises detecting the presence, absence, and/or quantity of at least one aspartyl protease or functional fragment thereof in a sample.

The present disclosure also relates to a method of diagnosing a subject with a mucinous cystic neoplasm (MCN). In one aspect, the method comprises detecting the presence, absence, and/or quantity of at least one aspartyl protease or functional fragment thereof in a sample.

The present disclosure also relates to a method of diagnosing a subject with a serous cystadenoma (SCA). In one aspect, the method comprises detecting the presence, absence, and/or quantity of at least one aspartyl protease or functional fragment thereof in a sample.

The present disclosure also relates to a method of diagnosing a subject with a pseudocyst. In one aspect, the method comprises detecting the presence, absence, and/or quantity of at least one aspartyl protease or functional fragment thereof in a sample.

The present disclosure also relates to a method of diagnosing a subject with a mucinous cyst. In one aspect, the method comprises: (a) detecting a presence or quantifying an amount of cathepsin E and/or gastricsin and/or functional fragment thereof, in a sample of the subject, by contacting the sample with a substrate specific for cathepsin E and/or gastricsin and/or functional fragment thereof; and (b) diagnosing a subject with a mucinous cyst when the presence or quantity of cathepsin E and/or gastricsin and/or functional fragment thereof is detected or quantified.

The present disclosure also relates to a method of diagnosing a subject with pancreatic cancer. In one aspect, the method comprises: (a) detecting a presence or quantifying an amount of cathepsin E and/or gastricsin and/or functional fragment thereof, in a sample of the subject, by contacting the sample with a substrate specific for cathepsin E and/or gastricsin and/or functional fragment thereof; and (b) diagnosing a subject with pancreatic cancer when the presence or quantity of cathepsin E and/or gastricsin and/or functional fragment thereof is detected or quantified.

The present disclosure also relates to a method of treating a subject in need thereof diagnosed with or suspected of having pancreatic cancer. In one aspect, the method comprises: (a) contacting a plurality of probes specific for cathepsin E and/or gastricsin and/or functional fragment thereof with a sample; (b) quantifying the amount of cathepsin E and/or gastricsin and/or functional fragment thereof in the sample; (c) calculating one or more scores based upon the presence, absence, or quantity of cathepsin E and/or gastricsin and/or functional fragment thereof; (d) correlating the one or more scores to the presence, absence, or quantity of cathepsin E and/or gastricsin and/or functional fragment thereof, such that if the amount of cathepsin E and/or gastricsin and/or functional fragment thereof is greater than the quantity of cathepsin E and/or gastricsin and/or functional fragment thereof in a control sample, the correlating step comprises diagnosing a subject with pancreatic cancer; and (e) administering to the subject a therapeutically effective amount of treatment for the pancreatic cancer.

The present disclosure also relates to a method of treating a subject in need thereof diagnosed with or suspected of having pancreatic cancer. In one aspect, the method comprises: (a) contacting one or a plurality of substrates specific for cathepsin E and/or gastricsin and/or functional fragment thereof with a sample; (b) quantifying the amount of cathepsin E and/or gastricsin and/or functional fragment thereof in the sample; (c) calculating one or more scores based upon the presence, absence, or quantity of cathepsin E and/or gastricsin and/or functional fragment thereof; (d) correlating the one or more scores to the presence, absence, or quantity of cathepsin E and/or gastricsin and/or functional fragment thereof, such that if the amount of cathepsin E and/or gastricsin and/or functional fragment thereof is greater than the quantity of cathepsin E and/or gastricsin and/or functional fragment thereof in a control sample, the correlating step comprises diagnosing a subject with pancreatic cancer; and (e) administering to the subject a therapeutically effective amount of treatment for the pancreatic cancer.

The present disclosure also relates to a system. In one aspect, the system comprises: (a) one or a plurality of probes and/or stains that bind to at least one cathepsin E and/or gastricsin and/or functional fragment thereof; and (b) one or more solid supports capable of quantifying the presence, absence and/or intensity of at least one or a plurality of probes and/or stains that bind to at least one cathepsin E and/or gastricsin and/or functional fragment thereof in a sample.

The present disclosure also relates to a method for characterizing the stage of development or pathology of a cyst comprising a hyperproliferative cell. In one aspect, the method comprises: (a) contacting a plurality of probes specific for cathepsin E and/or gastricsin and/or functional fragment thereof with a sample; (b) quantifying the amount of cathepsin E and/or gastricsin and/or functional fragment thereof in the sample; (c) calculating one or more normalized scores based upon the presence, absence, or quantity of cathepsin E and/or gastricsin and/or functional fragment thereof; and (d) correlating the one or more scores to the presence, absence, or quantity of cathepsin E and/or gastricsin and/or functional fragment thereof, such that if the amount of cathepsin E and/or gastricsin and/or functional fragment thereof is greater than the quantity of cathepsin E and/or gastricsin and/or functional fragment thereof in a control sample, the correlating step comprises characterizing the sample as comprising a cyst comprising a hyperproliferative cell.

The present disclosure also relates to a method of determining whether a subject has a mucinous cyst or malignant growth. In one aspect, the method comprises: detecting the presence, absence, or quantity of gastricsin or functional fragment thereof in a sample from the subject by contacting the sample with a probe specific for gastricsin or functional fragment thereof, and/or a substrate specific for gastricsin or functional fragment thereof.

The present disclosure also relates to a method of determining whether a subject has a mucinous cyst or malignant growth. In one aspect, the method comprises: detecting the presence, absence, or quantity of cathepsin E or functional fragment thereof in a sample from the subject by contacting the sample with a probe specific for cathepsin E or functional fragment thereof, and/or a substrate specific for cathepsin E or functional fragment thereof.

The present disclosure also relates to a method of detecting the presence of a pre-cancerous or cancerous cell in a subject. In one aspect, the method comprises: (a) contacting a plurality of probes specific for cathepsin E and/or gastricsin and/or CEA and/or functional fragment thereof with a sample from the subject; (b) quantifying the amount of cathepsin E and/or gastricsin and/or CEA and/or functional fragment thereof in the sample; (c) calculating one or more normalized scores based upon the presence, absence, or quantity of cathepsin E and/or gastricsin and/or CEA and/or functional fragment thereof; and (d) correlating the one or more scores to the presence, absence, or quantity of cathepsin E and/or gastricsin and/or CEA and/or functional fragment thereof, such that if the amount of cathepsin E and/or gastricsin and/or CEA and/or functional fragment thereof is greater than the quantity of cathepsin E and/or gastricsin and/or CEA and/or functional fragment thereof in a control sample, the correlating step comprises characterizing the sample as comprising a pre-cancerous or cancerous cell.

The present disclosure also relates to a method of determining whether a subject has a mucinous cyst or malignant growth. In one aspect, the method comprises detecting the presence, absence, or quantity of CEA, wherein the sensitivity to detecting CEA is equal to or greater than 70%.

The present disclosure also relates to a composition. In one aspect, the composition comprises one or a plurality of amino acid sequences comprising a substrate specific for an aspartyl protease.

The present disclosure also relates to a kit. In one aspect, the kit comprises a solid support comprising one or a plurality of compositions disclosed herein. In another aspect, the kit comprises (i) a solid support comprising one or a plurality of reaction vessels and (ii) a container comprising one or a plurality of substrates disclosed herein. In another aspect, the kit comprises (i) a first container comprising a solid support comprising one or a plurality of reaction vessels and (ii) one or a plurality of vials or tubes, each vial or tube comprising one or a combination of substrates disclosed herein. In another aspect, the kit comprises (i) a first container comprising a solid support comprising one or a plurality of reaction vessels and (ii) one or a plurality of probes for gastricsin or cathepsin E.

BRIEF DESCRIPTIONS OF THE DRAWINGS

Figure 1B:
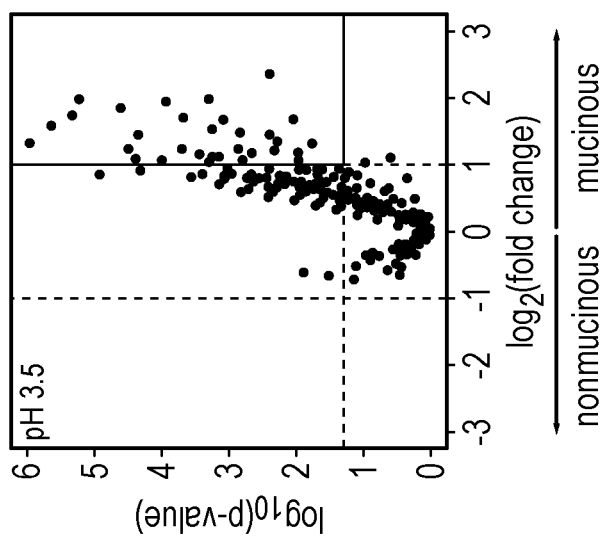
Figure 1C:
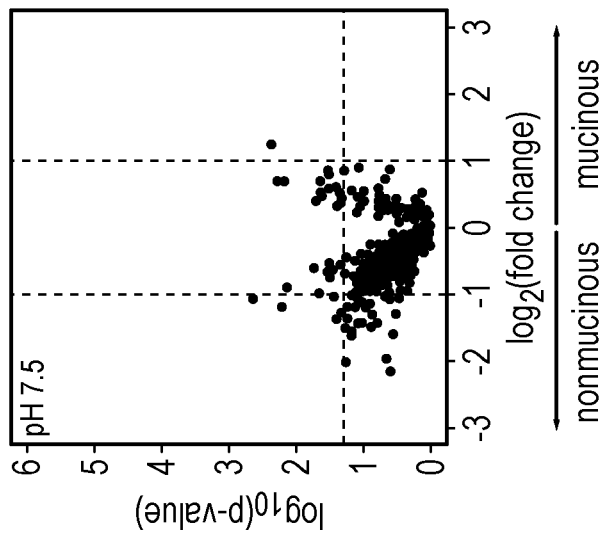

FIG. 1A-FIG. 1C: Comparison of global proteolytic activity in mucinous and nonmucinous cysts by MSP-MS. FIG. 1A and FIG. 1B show volcano plots displaying the peptide cleavages generated by mucinous (n=16) and nonmucinous cysts (n=7) when assayed at pH 7.5 (FIG. 1A) or pH 3.5 (FIG. 1B). Spectral counts of peptide cleavage products were used for relative quantification of the fold change (mucinous/nonmucinous) and hypothesis testing. Cleavages that met the criteria for differentiating mucinous from non-mucinous cysts (+/−1 $\log_2$ (fold change), p<0.05) are shown in blue. The substrate specificity of the cleavages within the red box is displayed with an iceLogo plot (FIG. 1C). Residues shown are statistically significant with p<0.05.

Figure 2A:
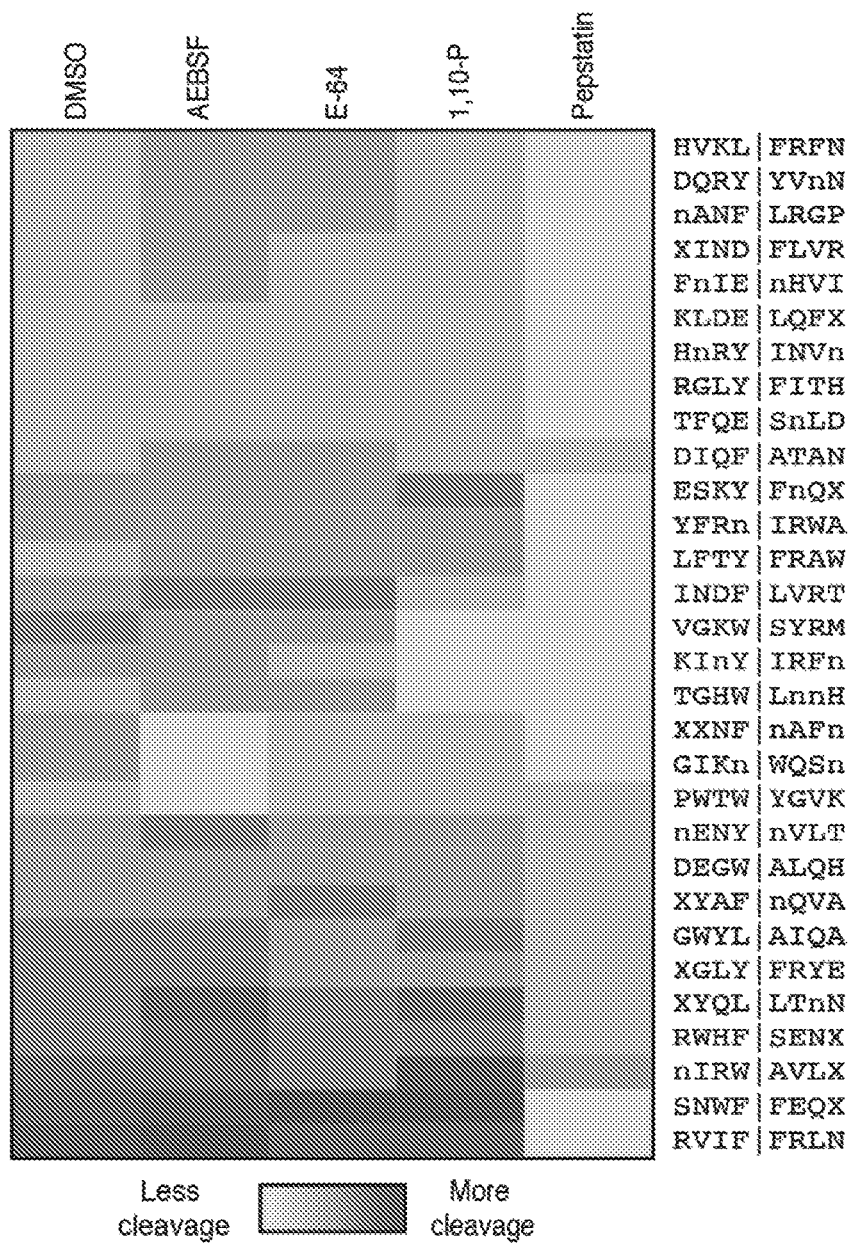
Figure 2B:
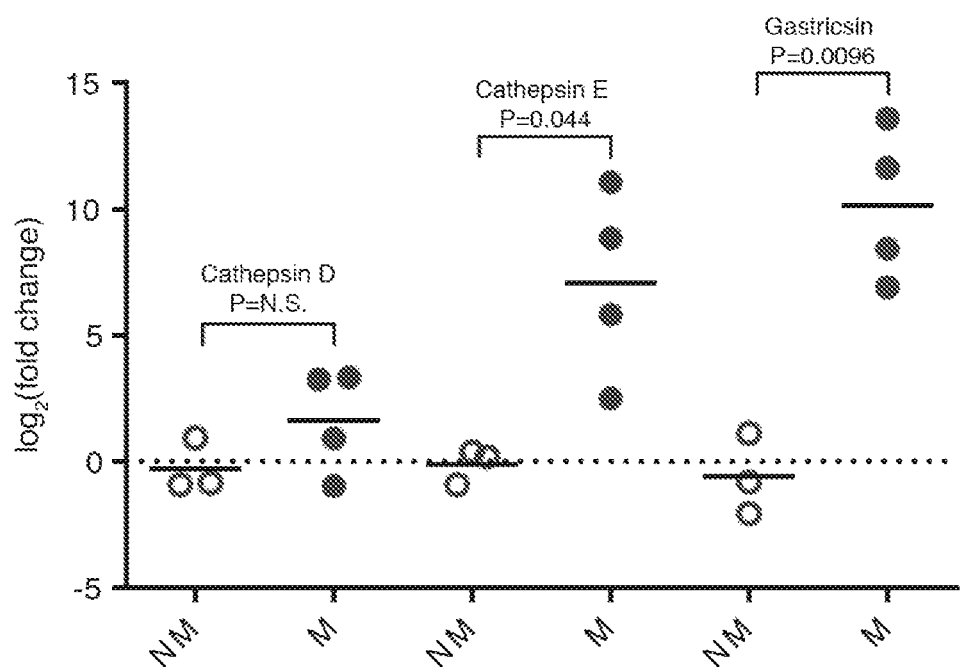
Figure 2C:
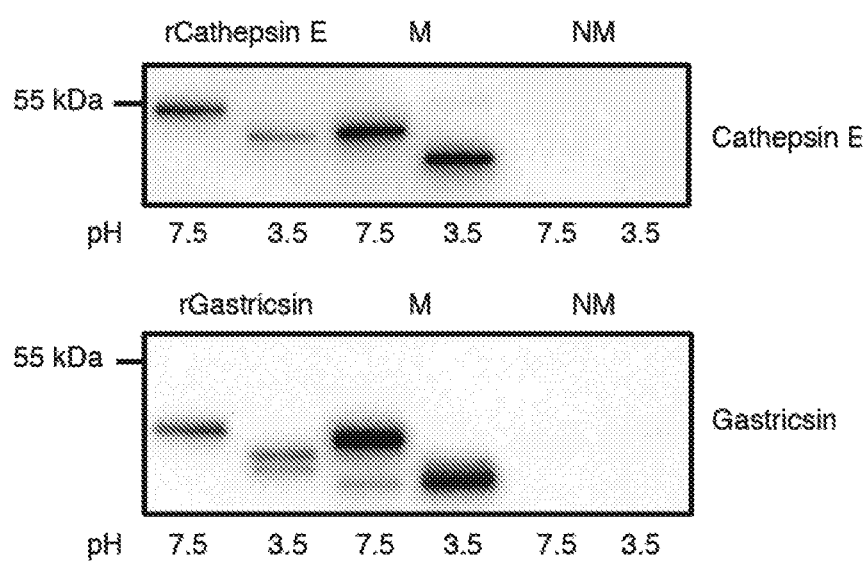

FIG. 2A-FIG. 2C: Identification of enriched aspartyl protease activity in mucinous cysts. FIG. 2A is a heatmap displaying cleavage of 30 mucinous-specific substrates (SEQ ID NOs: 14 through 43, from top to bottom) following treatment of a mucinous cyst fluid sample with DMSO or various broad-spectrum protease inhibitors. Spectral counts were used for relative quantification of peptide cleavage products. Vertical bar (I) indicates the site of cleavage within substrates. "n" in this figure refers to norleucine, used as an isostere for methionine, and "X" refers to no amino acid being present at that location. FIG. 2B shows label-free quantitation of aspartyl protease relative abundance in mucinous (M) and nonmucinous (NM) cysts. FIG. 2C is a Western blot analysis of recombinant (r) and cyst fluid-derived cathepsin E and gastricsin. Samples were pre-incubated at the indicated pH for 10 minutes.

FIG. 3A-FIG. 3H: Immunohistochemical analysis of gastricsin and cathepsin E in mucinous cysts. Histological analysis of mucinous cysts with low-grade dysplasia (FIG. 3A, FIG. 3B, FIG. 3E, FIG. 3F) and high-grade dysplasia (FIG. 3C, FIG. 3D, FIG. 3G, FIG. 3H). Gastricsin (FIG. 3A, FIG. 3C), cathepsin E (FIG. 3E, FIG. 3G), and haematoxylin and eosin (H&E) staining (FIG. 3B, FIG. 3D, FIG. 3F, FIG. 3H) in IPMNs (FIG. 3A-FIG. 3F) and MCNs (FIG. 3G-FIG. 3H). Scale bar is 10 μm.

FIG. 4A-FIG. 4D: Design and synthesis of gastricsin selective fluorescent substrate. (FIG. 4A) Substrate specificity of cathepsin D, cathepsin E, and gastricsin as determined by MSP-MS. Residues shown in iceLogo are statistically significant with p<0.05. (FIG. 4B) Heatmap comparing the amino acid enrichment Z-scores for gastricsin relative to cathepsin D and cathepsin E. (FIG. 4C) Venn diagram depicting the unique and overlapping cleavages detected by MSP-MS with cathepsin D, cathepsin E, and gastricsin. (FIG. 4D) Cleavage of the fluorescent substrates (SEQ ID NO: 1 and SEQ ID NO: 9) by cathepsin D, cathepsin E, and gastricsin. Activity was normalized to 1.00 based on the maximal activity against each substrate. Red arrow indicates the site of cleavage. Error bars denote standard error of the mean (SEM) from triplicate analysis.

Figure 5A:
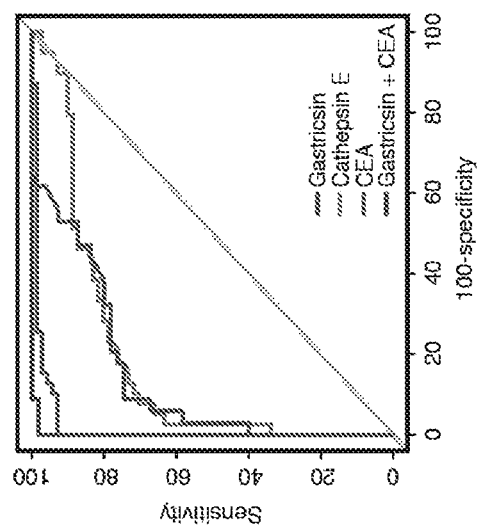
Figure 5B:
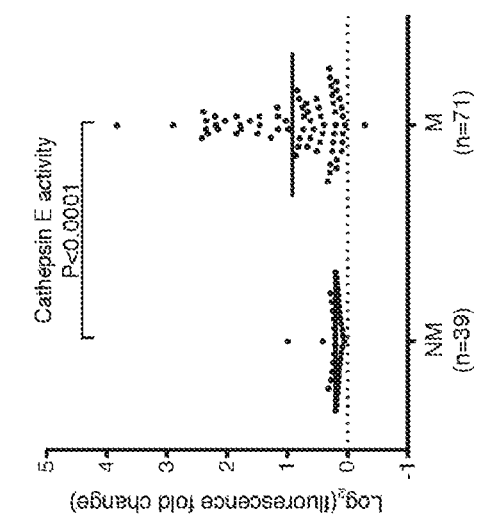
Figure 5C:
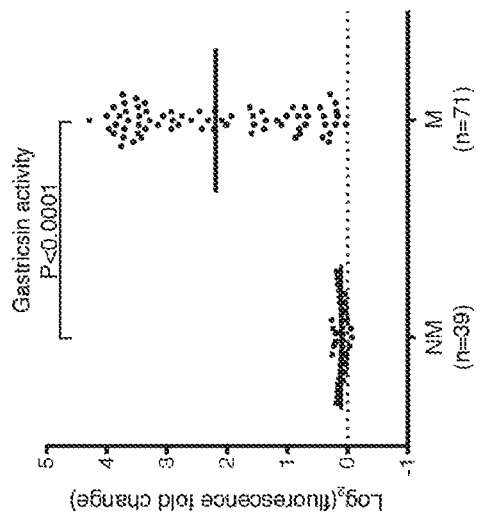

FIG. 5A-FIG. 5C: Quantification of gastricsin and cathepsin E activity in 110 cyst fluid samples. Analysis of gastricsin (FIG. 5A) and cathepsin E (FIG. 5B) activity in nonmucinous and mucinous cysts using fluorescent substrates. (FIG. 5C) ROC curves comparing sensitivity and specificity of CEA, gastricsin, cathepsin E, and CEA and gastricsin in combination.

Figures 6A, 6B:
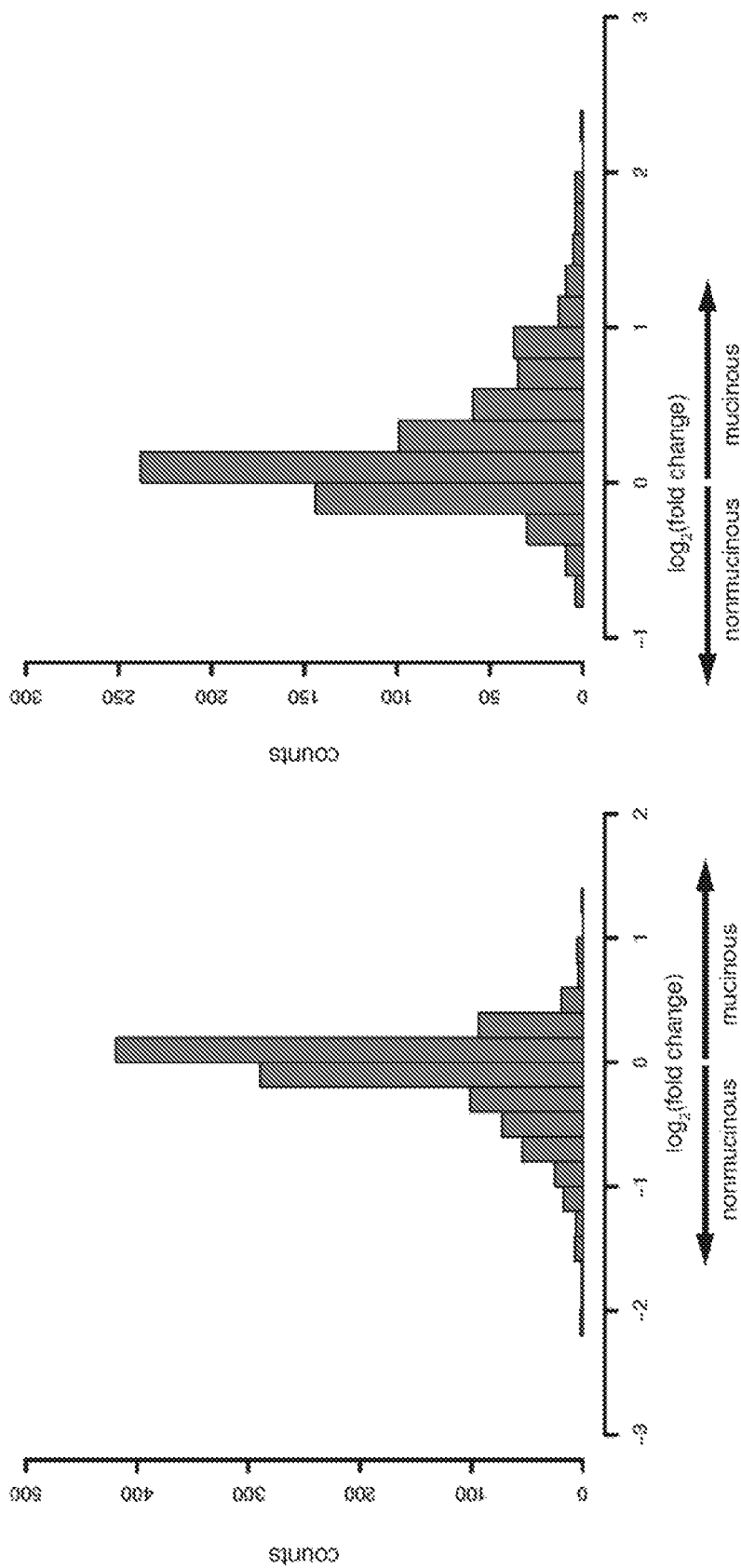

FIG. 6A-6B: Comparison of global proteolytic activity in mucinous and nonmucinous cysts by MSP-MS. Histograms depicting the number of cleavages enriched in mucinous and nonmucinous cysts at pH 3.5 (FIG. 6A) and pH 7.5 (FIG. 6B). Spectral counts of peptide cleavage products were used for quantification of the fold change (mucinous/nonmucinous) and counts are the number of peptide cleavages in each bin.

Figure 7B:
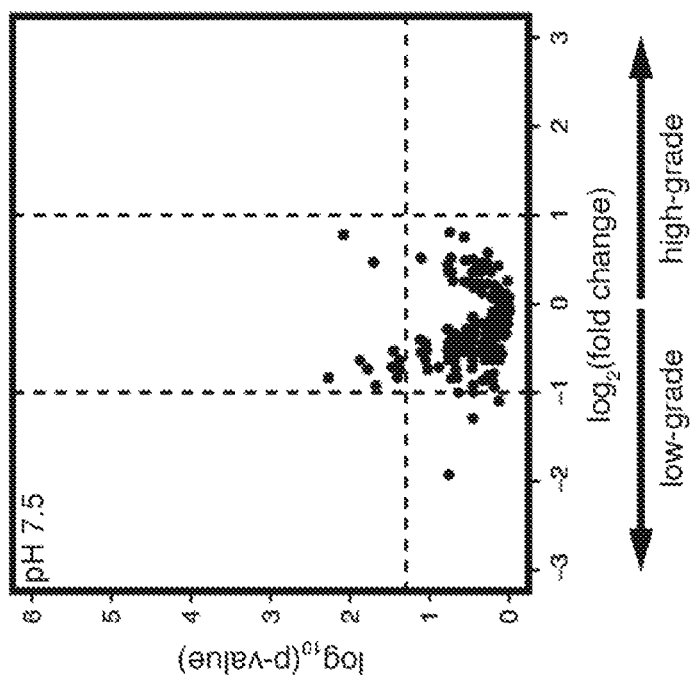
Figure 7A:
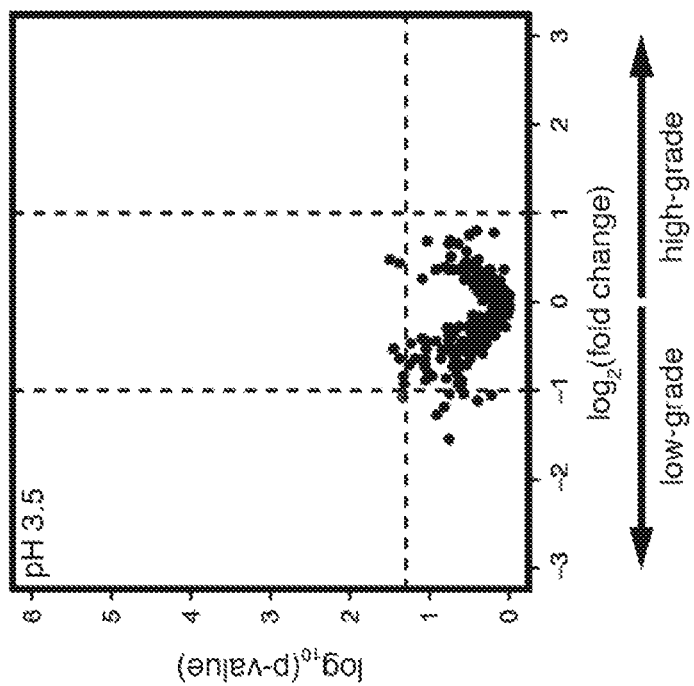

FIG. 7A-FIG. 7B: Comparison of global proteolytic activity in mucinous cysts with low- and high-grade dysplasia. Volcano plots displaying the peptide cleavages generated by the mucinous cysts with low-grade dysplasia (n=9) and high-grade dysplasia (n=7) at pH 3.5 (FIG. 7A) and pH 7.5 (FIG. 7B). Fold change corresponds to low-grade dysplasia/high-grade dysplasia.

Figure 8:
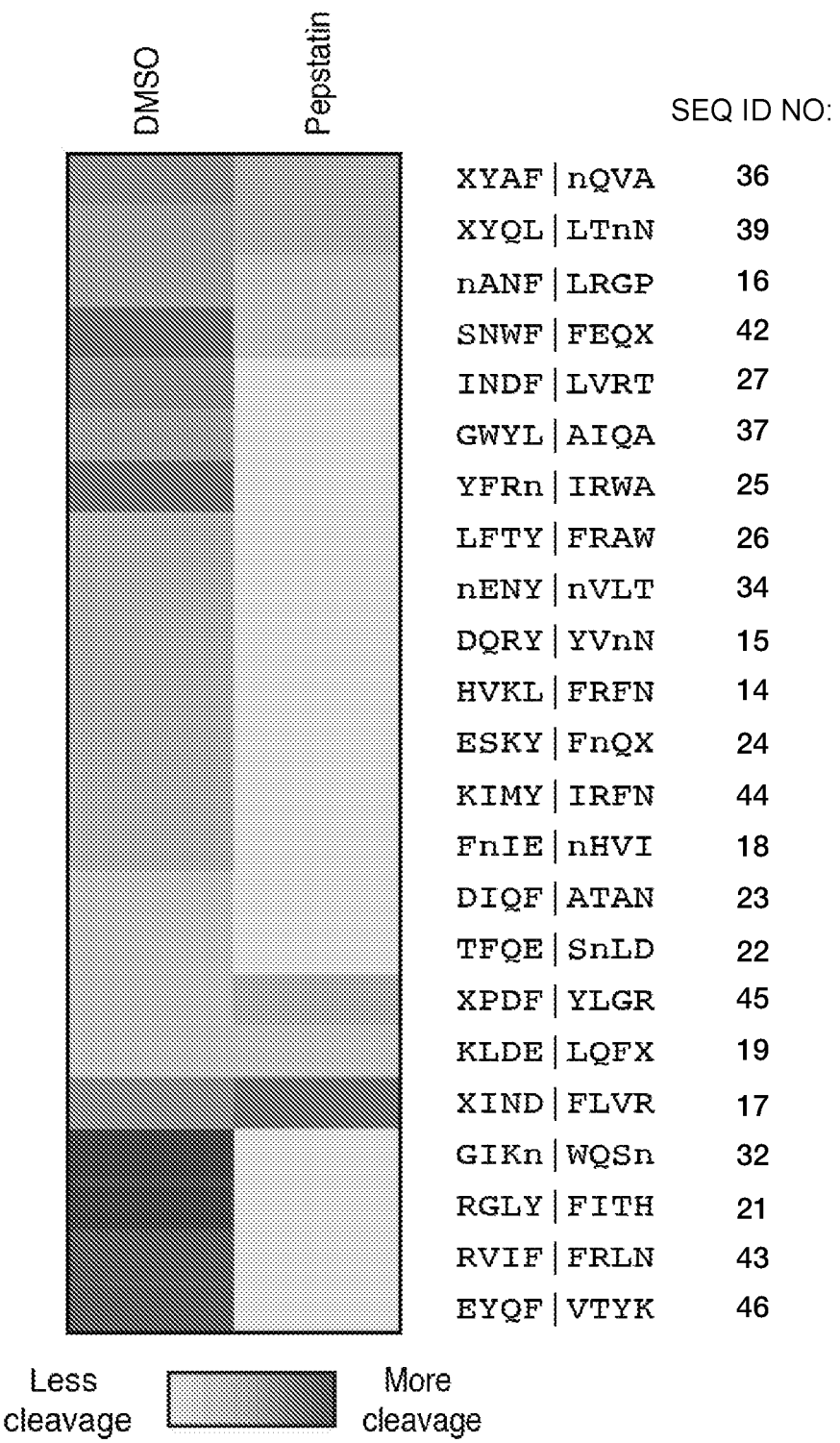

FIG. 8: Analysis of pepstatin inhibition on protease activity through MSP-MS. Heatmap displaying cleavage of 28 mucinous-specific substrates following treatment of a mucinous cyst fluid sample with DMSO or pepstatin. Spectral counts were used for relative quantification of peptide cleavage products. "n" in this figure refers to norleucine, used as an isostere for methionine, and "X" refers to no amino acid being present at that location.

Figure 9B:
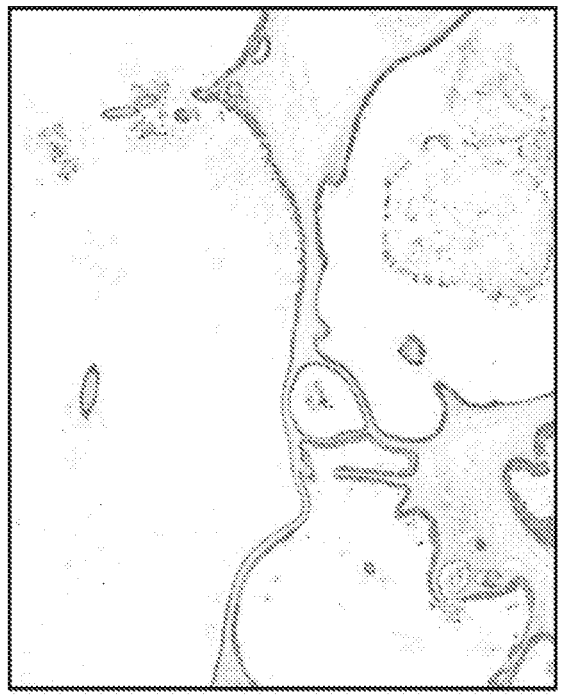
Figure 9A:

FIG. 9A-FIG. 9B: Immunohistochemical analysis of IPMN genetic mouse model. Immunohistochemical analysis of gastricsin (FIG. 9A) and cathepsin E (FIG. 9B) in a cystic lesion from a 40-week-old Ptf1a-Cre; LSL-Kras$^{G12D}$; Brg1$^{f/f}$ mouse.

Figure 10:
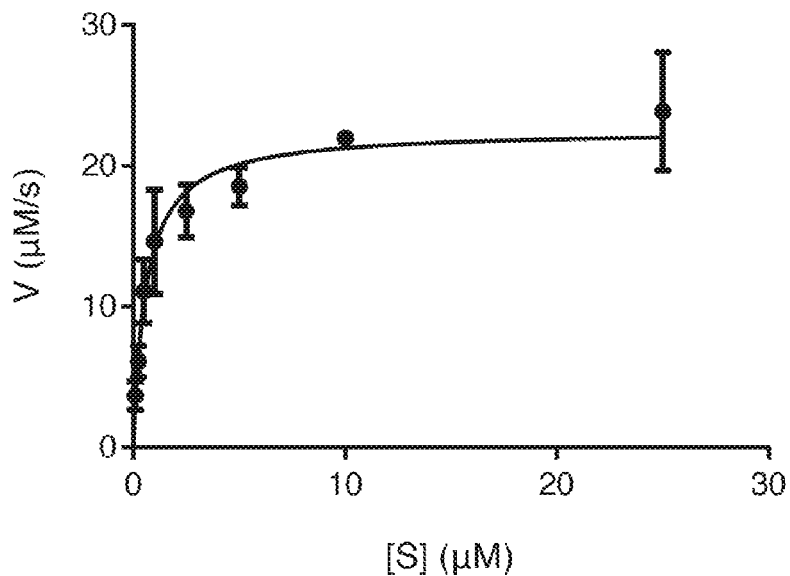

FIG. 10: Kinetic analysis of gastricsin selective substrate. Michaelis-Menten analysis of cleavage of DEGW^ALQH (SEQ ID NO: 1) substrate by gastricsin. kcat/Km=X, Vmax is Y. Error bars denote SEM from triplicate analysis.

Figure 11:
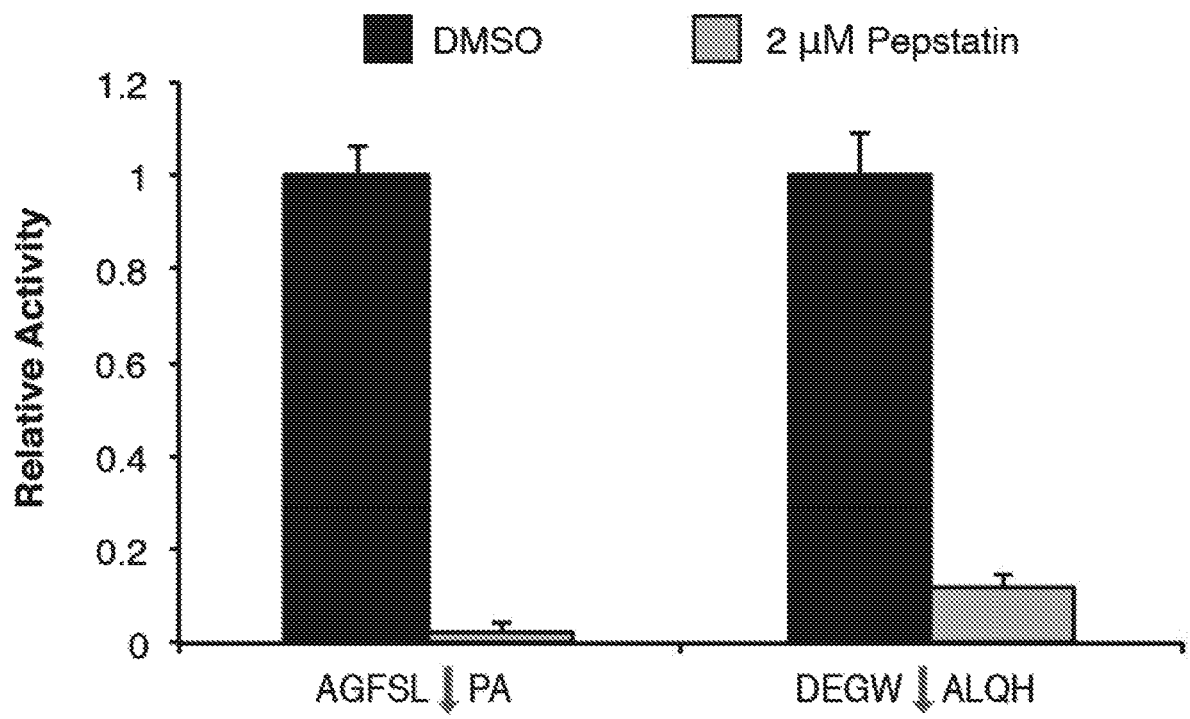

FIG. 11: Cleavage of aspartyl protease substrates in mucinous cysts. Pepstatin inhibition of cleavage of fluorescent substrates (SEQ ID NO: 9, left and SEQ ID NO: 1, right) by a mucinous cyst fluid sample. Activity was normalized relative to DMSO control treatment and error bars denote SEM from triplicate analysis.

Figure 12A:
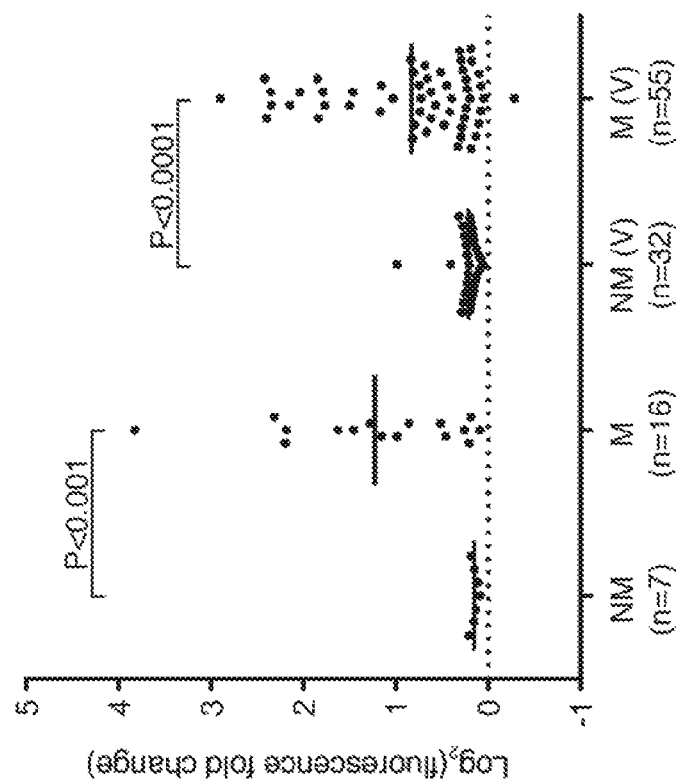
Figure 12B:
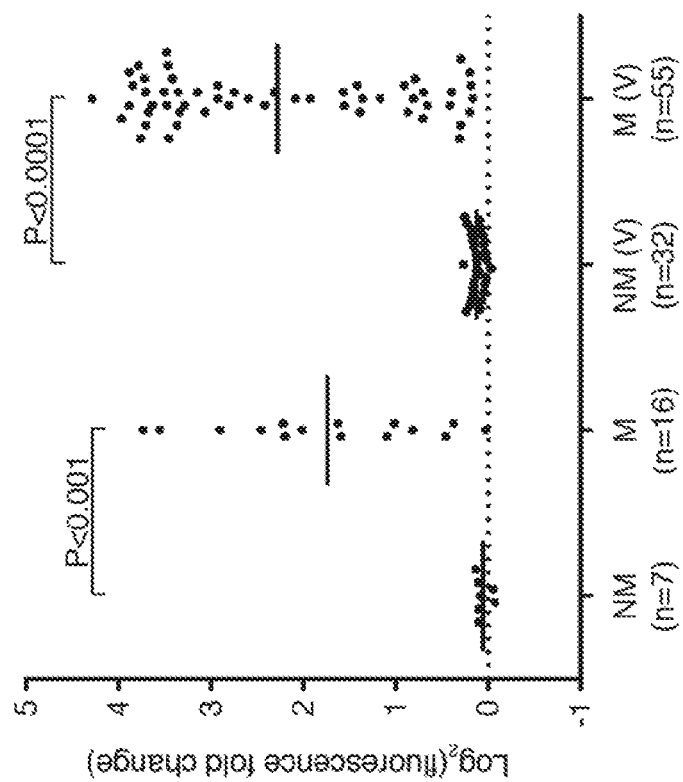

FIG. 12A-FIG. 12B: Quantification of aspartyl protease activity in cyst fluid samples using fluorescent peptide substrates. Gastricsin (FIG. 12A) and cathepsin E (FIG. 12B) activity in samples analyzed by MSP-MS and fluorescence (n=23) and in samples from validation (V) cohort (n=87) that were just assayed using fluorescent substrates.

Figures 13A, 13B:
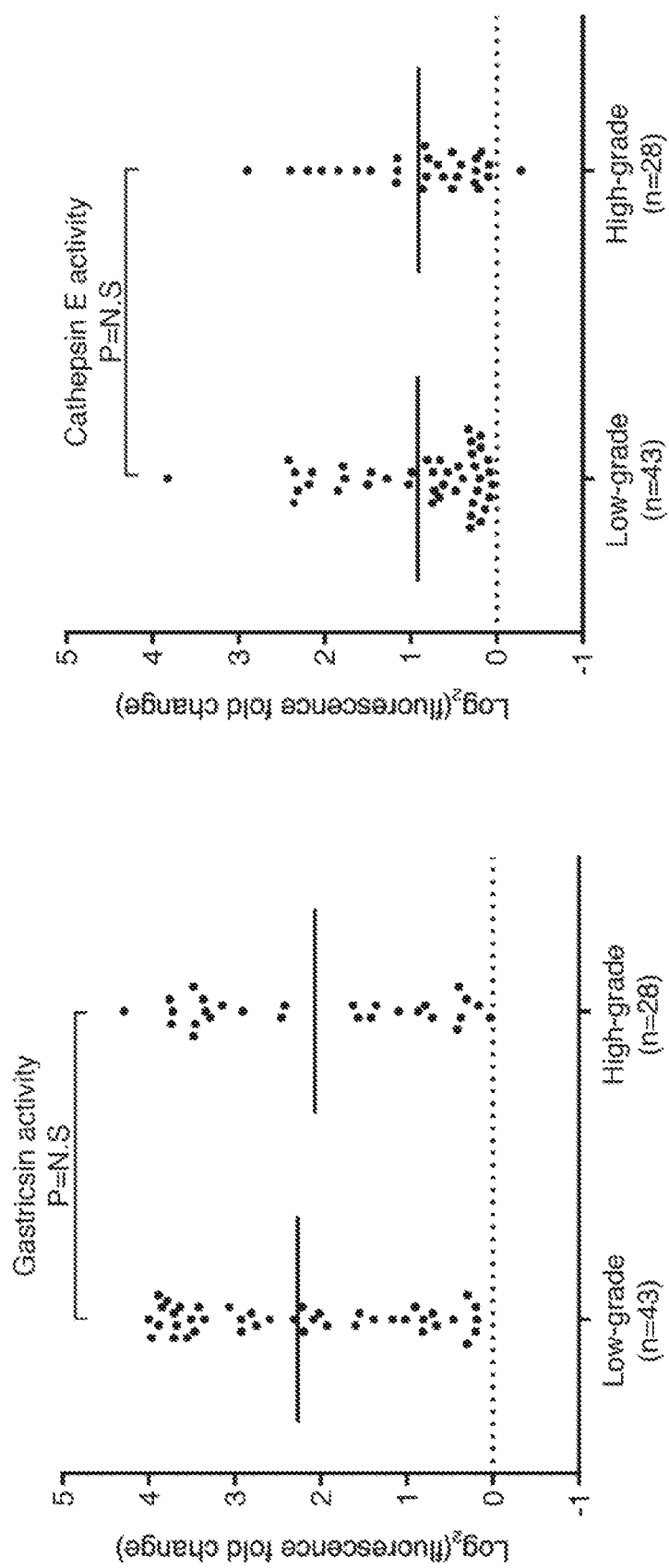
Figure 13D:
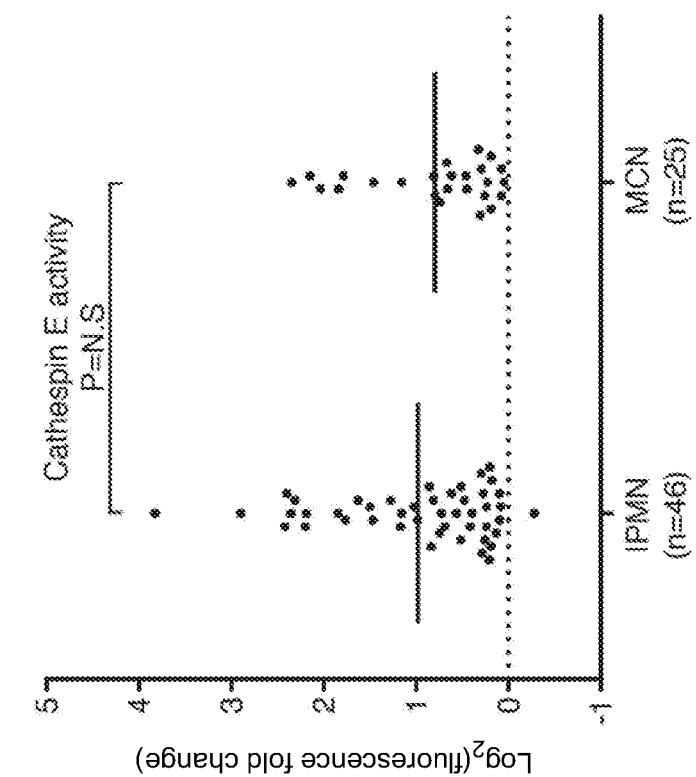
Figure 13C:
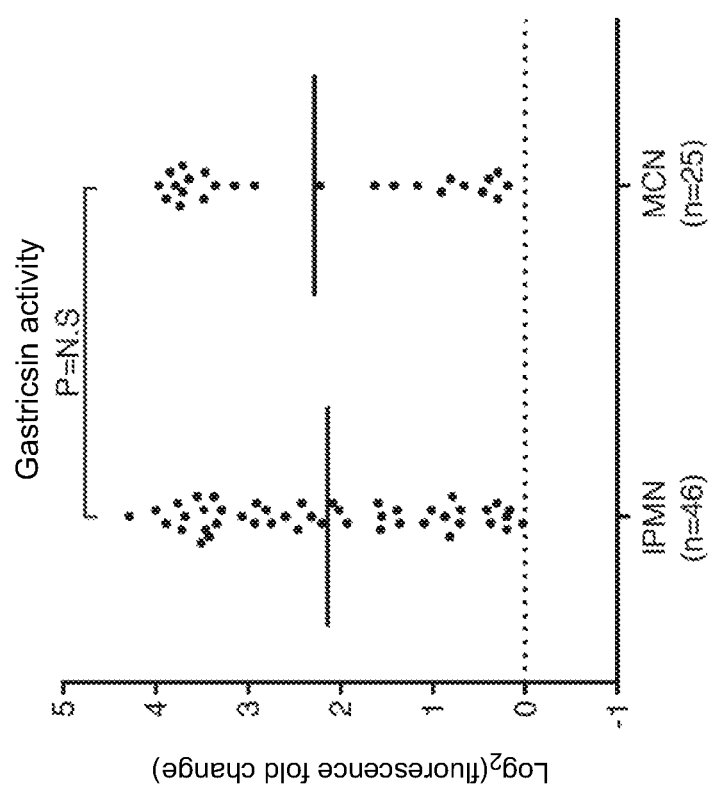

FIG. 13A-FIG. 13D: Analysis of gastricsin and cathepsin E activity in 71 mucinous cyst fluid samples. Gastricsin and cathepsin E activity in mucinous cysts with low- and high-grade dysplasia (FIG. 13A-FIG. 13B) or IPMNs and MCNs (FIG. 13C-FIG. 13D).

Figure 14:
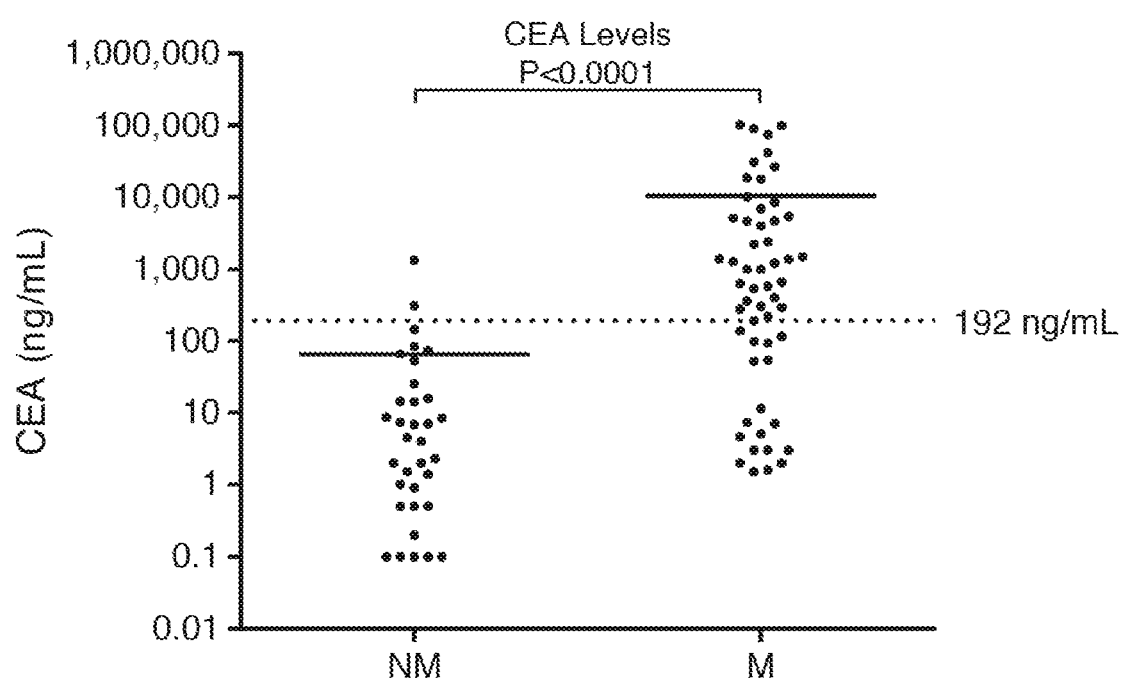

FIG. 14: CEA levels in mucinous and nonmucinous cysts. Dashed line indicates the standard clinical cutoff of 192 ng/mL.

Figure 15:
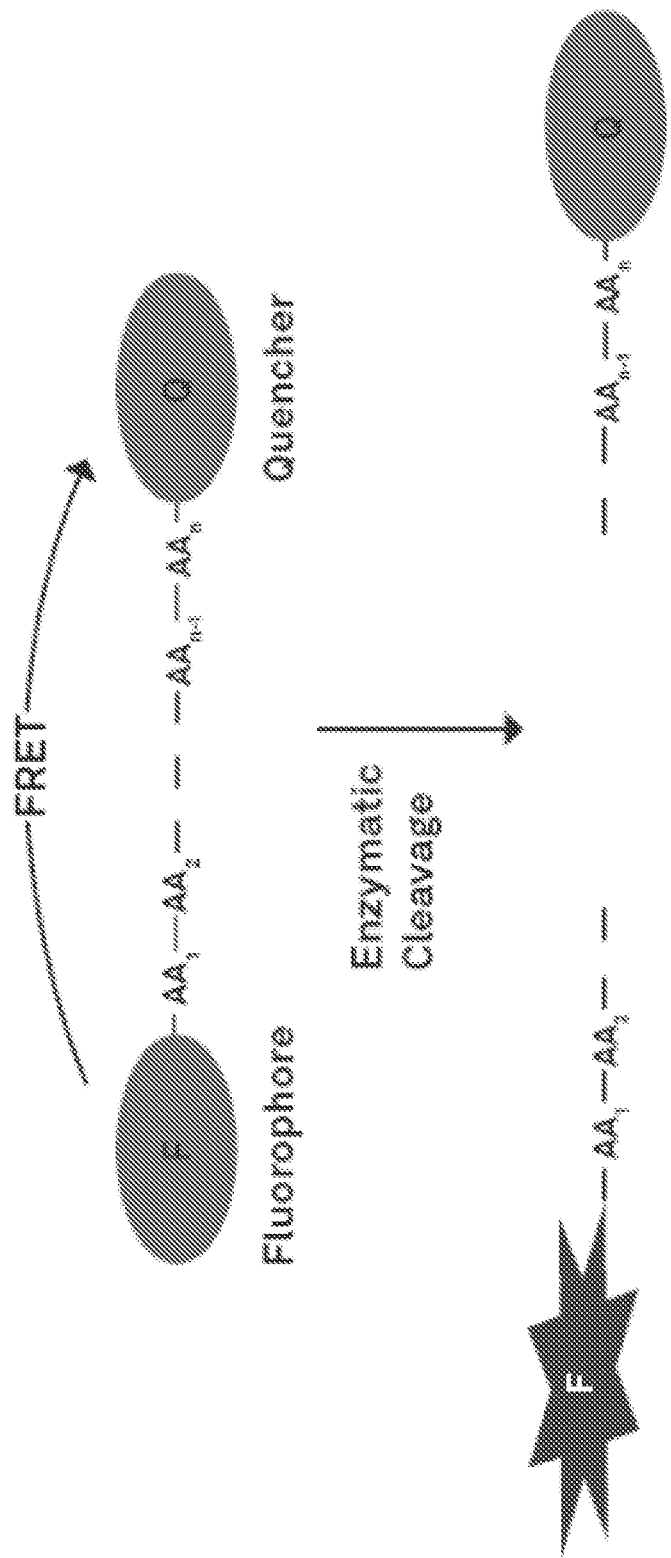

FIG. 15: Enzymatic cleavage of aspartyl protease substrates. Depiction of the cleavage of fluorescent peptide substrates.

Figure 16:
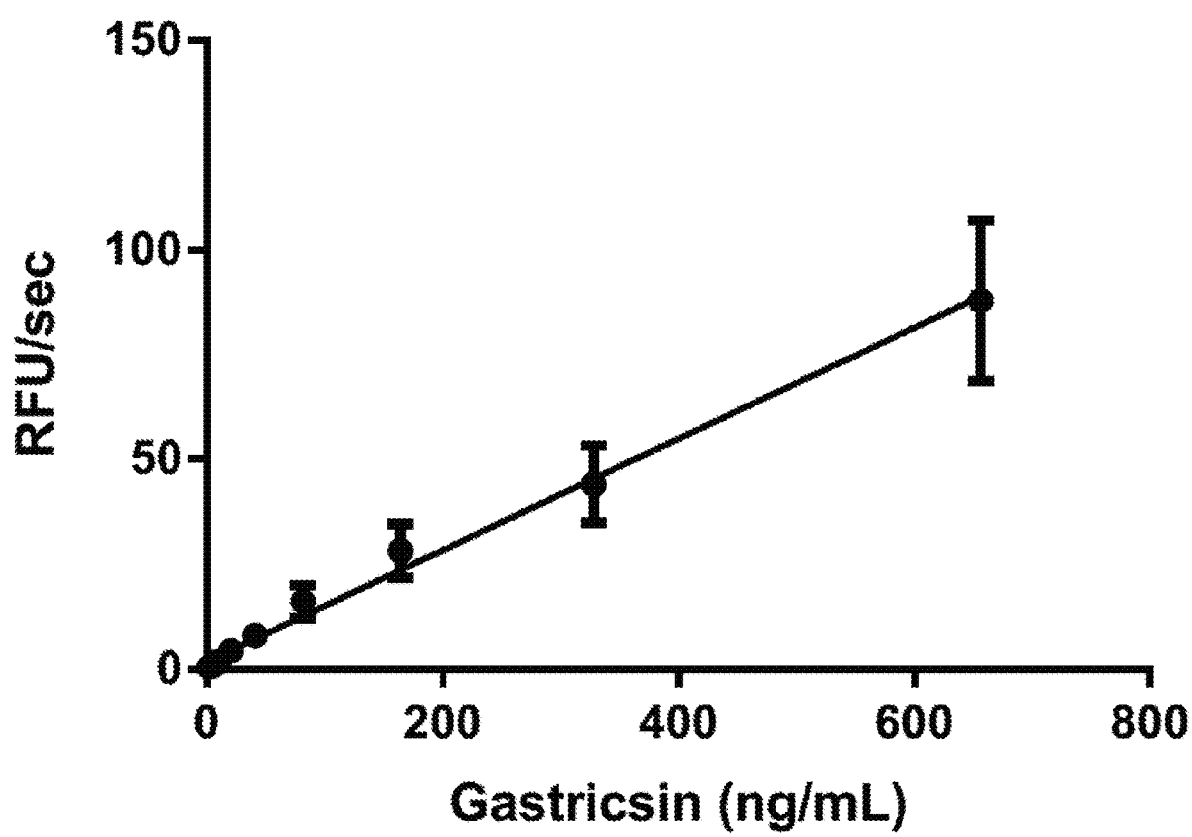

FIG. 16: Analysis of gastricsin abundance through fluorescence-based activity assay. Using the fluorescent substrate, the abundance of gastricsin was quantitated across a wide concentration range. The limit-of-detection is approximately 600 ng/mL.

Figure 17:
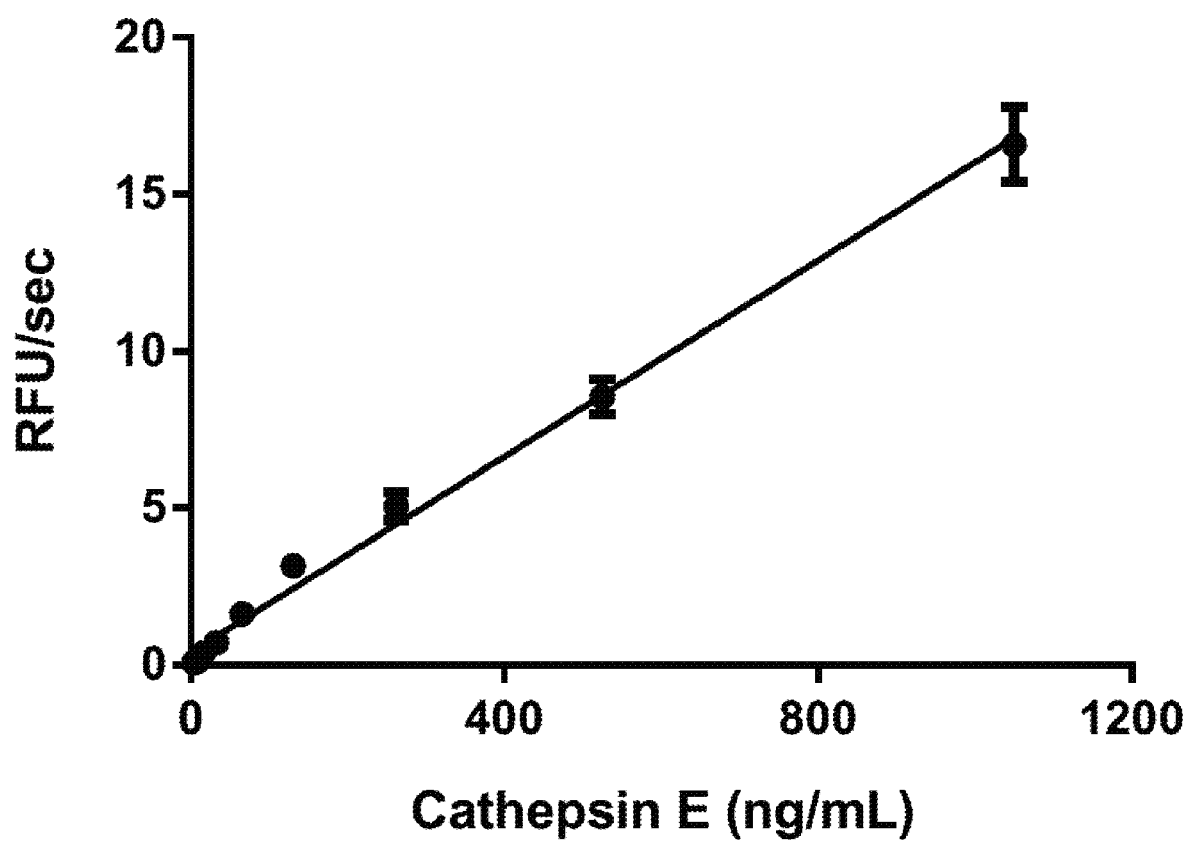

FIG. 17: Analysis of cathepsin E abundance through fluorescence-based activity assay. Using a previously reported fluorescent substrate, the abundance of cathepsin E was quantitated across a wide concentration range. The limit-of-detection is approximately 4 µg/mL.

Figure 18:
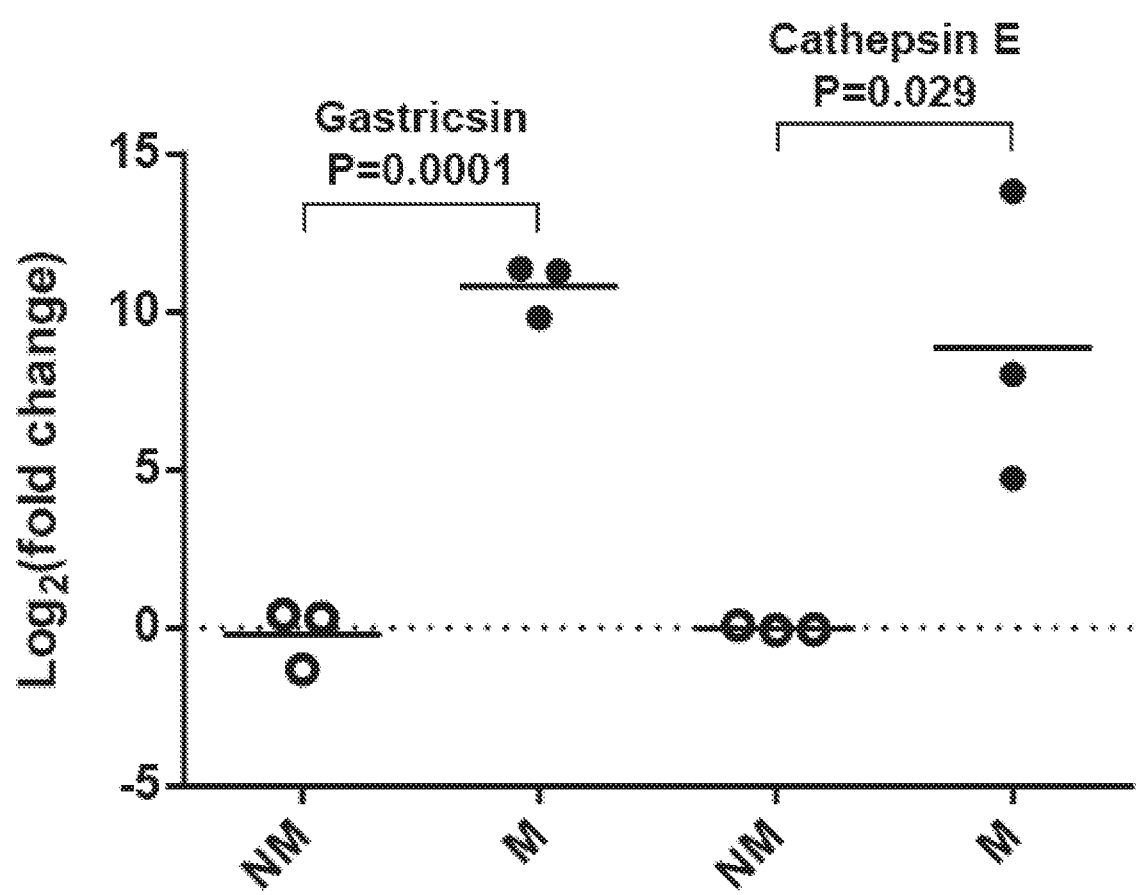

FIG. 18: Cathepsin E and gastricsin targeted proteomics. The abundance of peptides derived from cathepsin E and gastricsin were directly analyzed in patient cyst fluid using targeted proteomics. The abundance of both proteases was significantly higher in mucinous (M) relative to nonmucinous (NM) cyst fluid. Furthermore, gastricsin and cathepsin E peptides were detected in mucinous cyst fluid samples that only showed low levels of protease activity and are near the LOD of the activity-based assays.

Figure 19:
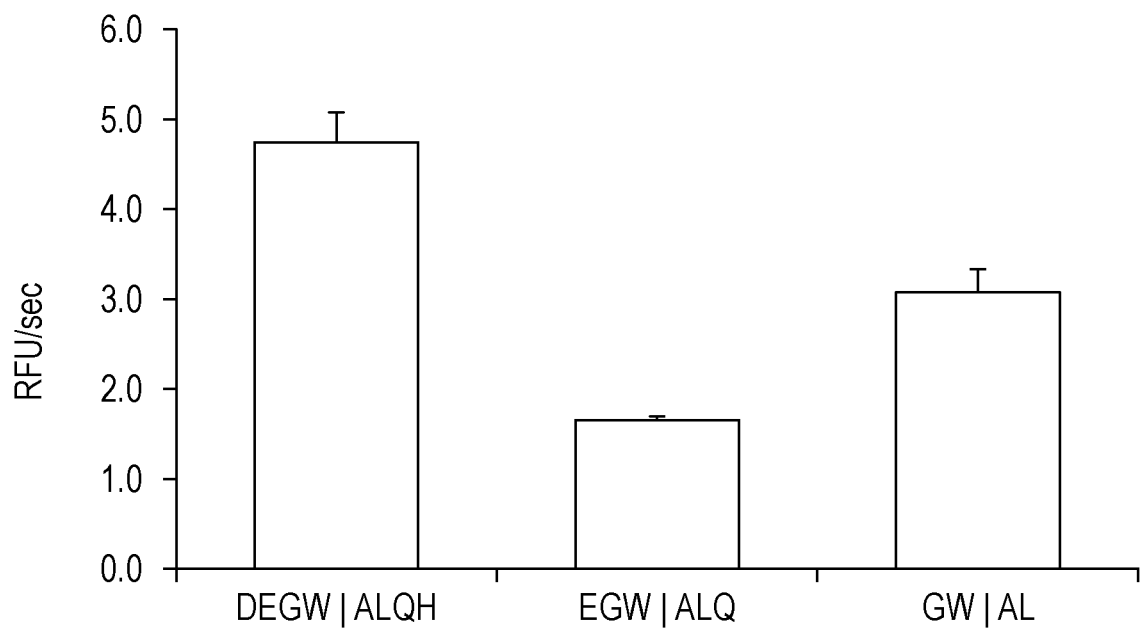

FIG. 19: Cleavage of fluorescent substrates by 10 nM of recombinant gastricsin. Site of cleavage is indicated by vertical bar (|). The original substrate used to assess gastricsin activity was DEGW|ALQH (SEQ ID NO: 1), with shorter peptides also demonstrating specificity (SEQ ID NO: 52 and SEQ ID NO: X, respectively).

DETAILED DESCRIPTION OF EMBODIMENTS

Before the present compositions and methods are described, it is to be understood that this disclosure is not limited to the particular molecules, compositions, methodologies or protocols described, as these may vary. It is also to be understood that the terminology used in the description is for the purpose of describing the particular versions or embodiments only, and is not intended to limit the scope of the present disclosure which will be limited only by the appended claims. It is understood that these embodiments are not limited to the particular methodology, protocols, cell lines, vectors, and reagents described, as these may vary. It also is to be understood that the terminology used herein is for the purpose of describing particular embodiments only, and is not intended to limit the scope of the present embodiments or claims.

Unless defined otherwise, all technical and scientific terms used herein have the same meanings as commonly understood by one of ordinary skill in the art. Although any methods and materials similar or equivalent to those described herein can be used in the practice or testing of embodiments of the present disclosure, the preferred methods, devices, and materials are now described. All publications mentioned herein are incorporated by reference. Nothing herein is to be construed as an admission that the disclosure is not entitled to antedate such disclosure by virtue of prior disclosure.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, "either," "one of," "only one of," or "exactly one of" "Consisting essentially of," when used in the claims, shall have its ordinary meaning as used in the field of patent law.

The term "about" as used herein when referring to a measurable value such as an amount, a temporal duration, and the like, is meant to encompass variations of ±20%, ±10%, ±5%, ±1%, ±0.9%, ±0.8%, ±0.7%, ±0.6%, ±0.5%, ±0.4%, ±0.3%, ±0.2% or ±0.1% from the specified value, as such variations are appropriate to perform the disclosed methods.

As used herein, the phrase "integer from X to Y" means any integer that includes the endpoints. That is, where a range is disclosed, each integer in the range including the endpoints is disclosed. For example, the phrase "integer from X to Y" discloses 1, 2, 3, 4, or 5 as well as the range 1 to 5.

As used herein, "substantially equal" means within a range known to be correlated to an abnormal or normal range at a given measured metric. For example, if a control sample is from a diseased patient, substantially equal is within an abnormal range. If a control sample is from a patient known not to have the condition being tested, substantially equal is within a normal range for that given metric. In some embodiments, the amount of expression of enzymes detected by any of the methods disclosed herein is from about 1.01 to about 2.00 times the amount of expression of the enzymes disclosed herein in order for the diagnosis of pre-malignant or malignant to be made. In some embodiments, the amount of expression of enzymes detected by any of the methods disclosed herein is from about 1.01 to about 1.50 times the amount of expression of the enzymes disclosed herein in order for the diagnosis of pre-malignant or malignant to be made.

As used herein, the term "subject," "individual" or "patient," used interchangeably, means any animal, including mammals, such as mice, rats, other rodents, rabbits, dogs, cats, swine, cattle, sheep, horses, or primates, such as humans.

The term "subject" is used throughout the specification to describe an animal from which a sample is taken. In some embodiment, the subject is a human. For diagnosis of those conditions which are specific for a specific subject, such as a human being, the term "patient" may be interchangeably used. In some instances in the description of the present invention, the term "patient" will refer to human patients suffering from a particular disease or disorder. In some embodiments, the subject may be a human suspected of having or being identified as at risk to develop a type of cancer more severe or invasive than initially diagnosed. In some embodiments, the subject may be diagnosed as having at resistance to one or a plurality of treatments to treat a disease or disorder afflicting the subject. In some embodiments, the subject is suspected of having or has been diagnosed with stage I, II, III or greater stage of cancer. In some embodiments, the subject may be a human suspected of having or being identified as at risk to a terminal condition or disorder. In some embodiments, the subject may be a mammal which functions as a source of the isolated sample of biopsy or bodily fluid. In some embodiments, the subject may be a non-human animal from which a sample of biopsy or bodily fluid is isolated or provided.

As used herein, the terms "biologically significant" refers to an amount or concentration of enzymatic reaction product or quantity of binding that is detected and is statistically significant as compared to a control when the amount or concentration is normalized for a control.

As used herein, the term "kit" refers to a set of components provided in the context of a system for delivering materials or diagnosing a subject with having a pancreatic cyst. Such delivery systems may include, for example, systems that allow for storage, transport, or delivery of various diagnostic or therapeutic reagents (e.g., oligonucleotides, enzymes, extracellular matrix components etc. in appropriate containers) and/or supporting materials (e.g., buffers, media, cells, written instructions for performing the assay etc.) from one location to another. For example, in some embodiments, kits include one or more enclosures (e.g., boxes) containing relevant reaction reagents and/or supporting materials. As used herein, the term "fragmented kit" refers to a diagnostic assay comprising two or more separate containers that each contain a subportion of total kit components. Containers may be delivered to an intended recipient together or separately. For example, a first container may contain a petri dish or polysterene plate for use in a cell culture assay, while a second container may contain cells, such as control cells. As another example, the kit may comprise a first container comprising a solid support such as a chip or slide with one or a plurality of ligands with affinities to one or a plurality of biomarkers disclosed herein and a second container comprising any one or plurality of reagents necessary for the detection and/or quantification of the amount of biomarkers in a sample. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contain a subportion of total kit components are included in the term "fragmented kit." In contrast, a "combined kit" refers to a delivery system containing all components in a single container (e.g., in a single box housing each of the desired components). The term "kit" includes both fragmented and combined kits.

As used herein, "cell culture" means growth, maintenance, transfection, or propagation of cells, tissues, or their products. As used herein, "culture medium" refers to any solution capable of sustaining the growth of the targeted cells either in vitro or in vivo, or any solution with which targeted cells or exogenous nucleic acids are mixed before being applied to cells in vitro or to a patient in vivo.

As used herein, the term "animal" includes, but is not limited to, humans and non-human vertebrates such as wild animals, rodents, such as rats, ferrets, and domesticated animals, and farm animals, such as dogs, cats, horses, pigs, cows, sheep, and goats. In some embodiments, the animal is a mammal. In some embodiments, the animal is a human. In some embodiments, the animal is a non-human mammal.

The terms "enzymatically effective amount" means any amount of the probe or substrate disclosed herein that is at a concentration capable of causing an enzymatic reaction in a detectable amount. In some embodiments, any of the disclosed methods comprise a step of contacting a probe with any disclosed aspartyl protease in an enzymatically effective amount. In some embodiments, the enzymatically effective amount As used herein, the term "mammal" means any animal in the class Mammalia such as rodent (i.e., a mouse, a rat, or a guinea pig), a monkey, a cat, a dog, a cow, a horse, a pig, or a human. In some embodiments, the mammal is a human. In some embodiments, the mammal refers to any non-human mammal. The present disclosure relates to any of the methods or compositions of matter disclosed herein wherein the sample is taken from a mammal or non-human mammal. The present disclosure relates to any of the methods or compositions of matter disclosed herein wherein the sample is taken from a human or non-human primate.

As used herein, the phrase "in need thereof" means that the animal or mammal has been identified or suspected as having a need for the particular method or treatment. In some embodiments, the identification can be by any means of diagnosis or observation. In any of the methods and treatments described herein, the animal or mammal can be in need thereof. In some embodiments, the animal or mammal is in an environment or will be traveling to an environment in which a particular disorder or condition is prevalent or more likely to occur.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the terms "hyperproliferative cell" means any cell of any subject that exhibits a disorder caused by dysfunction of its growth and/or division cycle. Hyperproliferative cells may be cancerous, benign or malignant.

As used herein, the phrase "therapeutically effective amount" means the amount of active compound or pharmaceutical agent or agent within a pharmaceutical composition that elicits the biological or medicinal response that is being sought in a tissue, system, animal, individual or human by a researcher, veterinarian, human physician or other clinician, such as a pathologist. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment.

As used herein, the terms "treat," "treated," or "treating" can refer to therapeutic treatment and/or prophylactic or preventative measures wherein the object is to prevent or slow down (lessen) an undesired physiological condition, disorder or disease, or obtain beneficial or desired clinical results. For purposes of the embodiments described herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment can also include eliciting a clinically significant response without excessive levels of side effects. Treatment also includes prolonging survival as compared to expected survival if not receiving treatment.

As used herein, the terms "diagnose," "diagnosing," or variants thereof refer to identifying the nature of a physiological condition, disorder or disease. In some embodiments, diagnosing a subject refers to identifying whether a cyst is benign, pre-malignant, or malignant. In some embodiments, diagnosing refers to distinguishing between a mucinous and non-mucinous cyst. In some embodiments, such a cyst is derived from or in the pancreas of the subject.

As used herein, a "cyst" is a membranous sac or cavity of abnormal character that may contain fluid. Mucinous cysts are a type of cyst that arise from epithelial cells, and have the potential to become malignant. Non-mucinous cysts of the pancreas are considered benign or harmless.

As used herein, "benign" is to be contrasted with "malignant". The terms "benign" and "malignant" are intended to convey their ordinary meaning. Therefore, "malignant" when modifying a growth is intended to refer to an abnormal growth or hyperproliferative state that is characterized by invasive or potentially invasive growth causing destruction of local tissues and cells, often leading to metastasis and death in the absence of treatment. In contrast, "benign" is intended to refer to an abnormal growth state wherein the growth does not result in the invasion of the local tissue, metastasis, or death. As used herein, "pre-malignant" is intended to refer to an abnormal growth state of a cell or group of cells prior to the biochemical alterations that cause the cell or group of cells within a given sample, cyst, tissue or sample to become malignant.

Any probes may be used in concert with any of the devices, kits, or methods disclosed herein. As used herein, the term "probe" refers to any molecule that may bind or associate, indirectly or directly, covalently or non-covalently, to any of the substrates and/or reaction products and/or proteases disclosed herein and whose association or binding is detectable using the methods disclosed herein. In some embodiments, the probe is a fluorogenic, fluorescent, or chemiluminescent probe, an antibody, or an absorbance-based probe. In some embodiments, an absorbance-based probe, for example the chromophore pNA (para-nitroanaline), may be used as a probe for detection and/or quantification of a protease disclosed herein. In some embodiments, the probe comprises an amino acid sequence that is a substrate of an enzyme disclosed herein and/or an analog or salt thereof, including those analogs that are at least about 70%, at least about 75%, at least about 80%, at least about 85%, at least about 87%, at least about 90%, at least about 95%, at least about 96%, at least about 97%, at least about 98%, or at least about 99% homologous to amino acids SEQ ID NOs: 1-9 below. A probe may be immobilized, adsorbed, or otherwise non-covalently bound to a solid surface, such that upon exposure to an enzyme for a time period sufficient to perform an enzymatic reaction, it can be enzymatically cleaved. In some embodiments, cleavage of the substrate causes a biological change in the nature or chemical availability of one or more probes such that cleavage enables detection of the reaction product. For instance, if the step of detecting comprises use of FRET, cleavage of the substrate disclosed herein causes one of the chromophore to emit a fluorescent light under exposure to a wavelength sufficient to activate such a fluorescent molecule. The intensity, length, or amplitude of a wavelength emitted from fluorescent marker can be measured and is, in some embodiments, proportional to the presence, absence or quantity of enzyme present in the reaction vessel, thereby the quantity of enzyme can be determined from detection of the intensity of or fluorescence at a known wavelength of light.

An "activity-based probe," as used herein, refers to a certain embodiment of probe comprising a small molecule that binds to or has affinity for a molecule such as a substrate that binds an enzyme in the presence of such an enzyme, such that its bound or unbound state confers an activity readout to the enzyme. In some embodiments, the activity-based probe covalently or non-covalently binds to an enzyme or functional fragment herein. In some embodiments, the binding of the activity-based probe modifies the physical or biological activity of the enzyme. In some embodiments, the activity-based probe can be fluorescent or chemiluminescent. In some embodiments, the activity-based probe has a measurable activity of one value if the enzyme is inactive and another measurable activity if in an activated state.

As used herein, the terms "fluorogenic" and "fluorescent" probe refer to any molecule (dye, quantum dot, peptide, or fluorescent marker) that emits a known and/or detectable wavelength of light upon exposure to a known wavelength of light. In some embodiments, the substrates or peptides with known cleavage sites recognizable by any of the enzymes expressed by one or a plurality of mucinous cysts are covalently or non-covalently attached to a fluorogenic probe. In some embodiments, the attachment of the fluorogenic probe to the substrate creates a chimeric molecule capable of a fluorescent emission or emissions upon exposure of the substrate to the enzyme and the known wavelength of light, such that exposure to the enzyme creates a reaction product which is quantifiable in the presence of a fluorimeter. In some embodiments, light from the fluorogenic probe is fully quenched upon exposure to the known wavelength of light before enzymatic cleavage of the substrate and the fluorogenic probe emits a known wavelength of light, the intensity of which is quantifiable by absorbance readings or intensity levels in the presence of a fluorimeter and after enzymatic cleavage of the substrate. In some embodiments, the fluorogenic probe is a coumarin-based dye or rhodamine-based dye with fluorescent emission spectra measurable or quantifiable in the presence of or exposure to a predetermined wavelength of light. In some embodiments, the fluorogenic probe comprises rhodamine. In some embodiments, the fluorogenic probe comprises rhodamine-100. Coumarin-based fluorogenic probes are known in the art, for example in U.S. Pat. Nos. 7,625,758 and 7,863,048, which are herein incorporated by reference in their entireties. In some embodiments, the fluorogenic probes are a component to, covalently bound to, non-covalently bound to, intercalated with one or a plurality of substrates to any of the enzymes disclosed herein. In some embodiments, the fluorogenic probes are chosen from ACC or AMC. In some embodiments, the fluorogenic probe is a fluorescein molecule. In some embodiments, the fluorogenic probe is capable of emitting a resonance wave detectable and/or quantifiable by a fluorimeter after exposure to one or a plurality of enzymes disclosed herein. "Fluorescence microscopy," which uses the fluorescence to generate an image, may be used to detect the presence, absence, or quantity of a fluorescent probe. In some embodiments, fluorescence microscopy comprises measuring fluorescence resonance energy transfer (FRET) within a FRET-based assay.

A "chemiluminescent probe" refers to any molecule (dye, peptide, or chemiluminescent marker) that emits a known and/or detectable wavelength of light as the result of a chemical reaction. Chemiluminescence differs from fluorescence or phosphorescence in that the electronic excited state is the product of a chemical reaction rather than of the absorption of a photon. Non-limiting examples of chemiluminescent probes are luciferin and aequorin molecules. In some embodiments, a chemiluminescent molecule is covalently or non-covalently attached to a substrate disclosed herein or an enzyme, such that the excited electronic state can be quantified to determine directly that an enzyme, such as an aspartyl protease, is in a reaction vessel, or, indirectly, by quantifying the amount of reaction product was produced after activation of the probe on the substrate or a portion of the substrate.

As used herein, an "enzyme" can be any partially or wholly proteinaceous molecule which carries out a chemical reaction in a catalytic manner upon exposure of a substrate. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art. Proteases of the present invention are enzymes that break down or cleave peptides.

As used herein, the term "sample" refers generally to a limited quantity of something which is intended to be similar to and represent a larger amount of that thing. In the present disclosure, a sample is a collection, fluid, blood, swab, brushing, scraping, biopsy, removed tissue, or surgical resection that is to be tested. In some embodiments, the sample is bodily fluid such as fluid from a pancreatic cyst. In some embodiments, samples are taken from a patient or subject that is believed to have a pancreatic cyst. In some embodiments, a sample believed to contain cells from a mucinous pancreatic cyst is compared to a "control sample" that is known not to contain mucinous cells. In some embodiments, a sample believed to comprise one or a plurality of cells derived from a mucinous pancreatic cyst is compared to a control sample that contains benign nonmucinous cells or is free of cells from a mucinous cyst. As used herein, "control sample" or "reference sample" refer to samples with a known presence, absence, or quantity of substance being measured, that is used for comparison against an experimental sample.

A "score" is a numerical value that may be assigned or generated after normalization of the value based upon the presence, absence, or quantity of substrates or enzymes disclosed herein. In some embodiments, the score is normalized in respect to a control score.

The disclosure relates to a system, composition, and series of methods of using the systems and compositions for the analysis of a sample from a subject to accurately diagnose, prognose, or classify the subject with a pancreatic cyst. The disclosure also relates to a system, composition, and series of methods of using the systems and compositions for the analysis of a sample from a subject to accurately diagnose, prognose, or classify the subject with a pancreatic cyst or pancreatic cancer. The disclosure relates to a system, composition, and series of methods of using the systems and compositions for the analysis of a sample from a subject to accurately diagnose, prognose, or classify the subject with a certain pancreatic cyst that is mucinous. In some embodiments, the system of the present invention comprises a means of detecting and/or quantifying morphological features, the expression of protein, or the expression of nucleic acids in a plurality of cells and correlating that data with a subject's medical history to predict clinical outcome, treatment plans, preventive medicine plans, or effective therapies. In some embodiments, the disclosure relates to methods of detecting pancreatic cancer or staging pancreatic cancer based upon the detected presence of a pancreatic ductal adenocarcinoma (PDA), an intraductal papillary mucinous neoplasm (IPMN), a mucinous cystic neoplasm (MCN), a serous cystadenoma (SCA), or a pseudocyst.

The disclosure also relates to a method of detecting the presence, absence, or quantity of mucinous cells based upon measurements of the levels of aspartyl protease in a sample. The method may comprise a step of quantifying the amount of cathepsin E, gastricsin or functional fragment in a sample by exposing a sample known to comprise or suspected of comprising the enzyme(s) or functional fragments to one or a plurality of substrates known to degrade or cleave into peptide domains or components after exposure to an aspartyl protease or functional fragment in a sample for a period sufficient to degrade or cleave the protein or peptide substrate. The pieces or domains or fragments of the substrate proteins or peptides can form a predetermined or expected number of fragments of a particular size depending upon the concentration of the aspartyl protease or proteases in a sample, the concentration of substrates in a sample, and/or the length of exposure time. In some embodiments, the amount of aspartyl protease in a sample is determined by the number and concentration of peptide fragments from an aspartyl protease substrate detected in a sample after exposure of that sample to an aspartyl protease substrate library or plurality of libraries. The data collected on the number and concentration of substrate fragments can be compiled in a cleavage signature that, when compared to cleavage signature of known mucinous cysts, can be used as evidence to correlate the signature to a diagnosis or detection of the presence of mucinous cells.

As used herein, the terms "peptide," "polypeptide" and "protein" are used interchangeably and refer to two or more amino acids covalently linked by an amide bond or non-amide equivalent. The peptides of the disclosure can be of any length. For example, the peptides can have from about two to about 100 or more residues, such as, 5 to 12, 12 to 15, 15 to 18, 18 to 25, 25 to 50, 50 to 75, 75 to 100, or more in length. Preferably, peptides are from about 2 to about 18 residues in length. The peptides of the disclosure also include l- and d-isomers, and combinations of l- and d-isomers. The peptides can include modifications typically associated with posttranslational processing of proteins, for example, cyclization (e.g., disulfide or amide bond), phosphorylation, glycosylation, carboxylation, ubiquitination, myristylation, or lipidation.

The terms "functional fragment" means any portion of a polypeptide or nucleic acid sequence from which the respective full-length polypeptide or nucleic acid relates that is of a sufficient length and has a sufficient structure to confer a biological affect that is at least similar or substantially similar to the full-length polypeptide or nucleic acid upon which the fragment is based. In some embodiments, a functional fragment is a portion of a full-length or wild-type nucleic acid sequence that encodes any one of the nucleic acid sequences disclosed herein, and said portion encodes a polypeptide of a certain length and/or structure that is less than full-length but encodes a domain that still biologically functional as compared to the full-length or wild-type protein. In some embodiments, the functional fragment may have a reduced biological activity, about equivalent biological activity, or an enhanced biological activity as compared to the wild-type or full-length polypeptide sequence upon which the fragment is based. In some embodiments, the functional fragment is derived from the sequence of an organism, such as a human. In such embodiments, the functional fragment may retain 99%, 98%, 97%, 96%, 95%, 94%, 93%, 92%, 91%, or 90% sequence identity to the wild-type human sequence upon which the sequence is derived. In some embodiments, the functional fragment may retain 87%, 85%, 80%, 75%, 70%, 65%, or 60% sequence homology to the wild-type sequence upon which the sequence is derived.

Aspartyl proteases, also known as acid proteases, are a widely distributed family of proteolytic enzymes that exist in vertebrates, fungi, plants, retroviruses and some plant viruses (Foltman (1981) *Essays Biochem* 17:52-84; Davis (1990) *Annu. Rev. Biophys. Chem.* 19: 189-215; Rao et al. (1991) *Biochemistry* 30: 4663-4671). Aspartyl proteases of eukaryotes are monomeric enzymes which consist of two domains. Each domain contains an active site centered on a catalytic aspartyl residue. The two domains most probably evolved from the duplication of an ancestral gene encoding a primordial domain. Currently known eukaryotic aspartyl proteases include, but are not limited to: vertebrate gastric pepsins A and C (also known as gastricsin), vertebrate lysosomal cathepsins D and E, vertebrate chymosin (rennin), mammalian renin, fungal proteases such as aspergillopepsin A, candidapepsin, mucoropepsin (mucor rennin), endothiapepsin, polyporopepsin, and rhizopuspepsin, yeast saccharopepsin (proteinase A), yeast barrierpepsin (gene BAR1), fission yeast sxa1.

Some embodiments include methods and systems with the use of Carcinoembryonic antigen (CEA). CEA is a set of highly related glycoproteins (including CD66a, CD66b, CD66c, CD66d, CD66e, and CD66f) involved in cell adhesion which are normally produced in gastrointestinal tissue during fetal development, but the production stops before birth. Therefore, CEA is usually present only at very low levels in the blood of healthy adults. However, the serum levels are raised in some types of cancer, which means that it can be used as a tumor marker in clinical tests. In some embodiments of the present invention, the presence, absence, and/or quantity of CEA is detected.

As used herein, the terms "substrate cleaved in the presence of" is a molecule comprising an amino acid sequence recognized by any aspartyl protease disclosed herein and cleaved at that amino acid sequence. In some embodiments, the substrate is cleaved in the presence of gastricsin and/or cathepsin E. Some embodiments of substrates cleaved in the presence of gastricsin and/or cathepsin E are shown in Table 1 below. In some embodiments, the substrates comprise a fluorophore and/or quencher with the target amino acid sequences positioned therebetween. In these embodiments, fluorescence is only observed following cleavage of the peptide sequence (such as, for example, FIG. 15). In some embodiments, the aspartyl proteases disclosed herein cut substrates between amino acids $X_4$ and $X_5$ when the following sequence features are included:

(SEQ ID NO: 47)
$$X_1-X_2-X_3-X_4-X_5-X_6-X_7-X_8$$

wherein $X_1$ is D;
$X_2$ is E, F, W, or Y;
$X_3$ is G, D, M, or R;
$X_4$ is Y, F, W, L, or M;
$X_5$ is Y, M, L, A, F, or S;
$X_6$ is L, T or R;
$X_7$ is Q or Y; and
$X_8$ is H.

In some embodiments, the aspartyl proteases disclosed herein cut substrates between amino acids $X_4$ and $X_5$ when the following sequence features are included:

(SEQ ID NO: 48)
$$X_3-X_4-X_5-X_6$$

$X_3$ is independently selected from G, K, T, D, M, I, L S or R or a modified amino acid residue thereof;
$X_4$ is independently selected from Y, F, A, W, L, Y, norleucine or M or a modified amino acid residue thereof;
$X_5$ is independently selected from Y, M, L, A, F, T, P or S or a modified amino acid residue thereof; and
$X_6$ is independently selected from L, Y, G, A, T or R or a modified amino acid residue thereof.

TABLE 1

Aspartyl protease substrates. Table 1 discloses SEQ ID NOs: 1-9, respectively, in order of appearance.

| Target Protease | Sequence (I = site of cleavage) | Total Cleavage | Relative Cleavage | kcat/Km (M-1/s-1) | Pubmed ID | Sensitivity (%) | Specificity (%) |
|---|---|---|---|---|---|---|---|
| Gastricsin | DEGW\|ALQH | 30 | 0.47 | $4.8 \times 10^5$ | | 93 | 100 |
| | VGKW\|SYRM | 22 | 0.34 | | | | |
| | NMKW\|TRVL | 21 | 0.33 | | | | |
| | PWTW\|YGVK | 64 | 1.00 | | | | |

TABLE 1-continued

Aspartyl protease substrates. Table 1 discloses SEQ ID NOs: 1-9, respectively, in order of appearance.

| Target Protease | Sequence (I = site of cleavage) | Total Cleavage | Relative Cleavage | kcat/Km (M-1/s-1) | Pubmed ID | Sensitivity (%) | Specificity (%) |
|---|---|---|---|---|---|---|---|
| Cathepsin E | FGIF\|YLNG | 22 | 0.88 | | | | |
| | HMIA\|LYWG | 10 | 0.40 | | | | |
| | IKIL\|MFYW | 17 | 0.68 | | | | |
| | GLY\|FRYE | 25 | 1.00 | | | | |
| | AGFSL\|PA | | | $1.7 \times 10^7$ | 20600629 | 70 | 92 |

In some embodiments, the aspartyl proteases disclosed herein cut substrates at the position between the amino acids identified with a line in FIGS. 2A and 8. In some embodiments, any of the probes comprise any one or combination of amino acid sequence identified in Table 1, FIG. 2A, or FIG. 8, and, in methods in which they are used, the methods comprise a step in which diagnosing occurs by detecting the presence or quantity of reaction product formed by any of the disclosed aspartyl proteases contacting one or a combination of probes in an enzymatically effective amount sufficient to cause probe to cleave into a reaction product.

In some embodiments, aspartyl proteases, specifically cathepsin E or gastricsin, can serve as specific markers useful for the discrimination between a mucinous or non-mucinous cyst. In the present disclosure, proteomic biomarkers for detecting mucinous cysts are described, as are reagents, kits, and methods designed to detect these biomarkers. The reagents, kits, and methods may be used in clinical application for testing for the presence of mucinous cysts. In some embodiments, cathepsin E is a major mucinous-specific protease. In some embodiments, gastricsin is a major mucinous-specific protease. In some embodiments, the presence of high amounts of cathepsin E and/or gastricsin is a strong indication of mucinous cyst formation. In some embodiments, samples that display high levels of peptide reaction products cathepsin E and/or gastricsin are highly likely to form, or have already formed, a mucinous cyst. In some embodiments, the presence of high amounts of cathepsin E and/or gastricsin reaction products can be used to deduce or approximate the quantity of cathepsin E and/or gastricsin (or functional fragments thereof) in a sample. In some embodiments, the step of quantifying the amount of cathepsin E, gastricsin or functional fragments thereof comprises creating a cleavage signature correlating the quantity of cathepsin E/gastricsin reaction products in a sample after exposure of that sample to a known library of one or a plurality of cathepsin E or gastricsin substrates with known amino acid sequences.

As used herein, "specific for" or "specifically binds to" means that the binding affinity of a substrate to a specified target nucleic acid sequence, such as an aspartyl protease, is statistically higher than the binding affinity of the same substrate to a generally comparable, but non-target nucleic acid sequence. Normally, the binding affinity of a substrate to a specified target nucleic acid sequence is at least 1.5 fold, and preferably 2 fold or 5 fold, of the binding affinity of the same substrate to a non-target nucleic acid sequence. It also refers to binding of a substrate to a specified nucleic acid target sequence to a detectably greater degree, e.g., at least 1.5-fold over background, than its binding to non-target nucleic acid sequences and to the substantial exclusion of non-target nucleic acids. The substrate's Kd to each nucleotide sequence can be compared to assess the binding specificity of the substrate to a particular target nucleotide sequence.

In some embodiments, cathepsin E may refer to an amino acid sequence according to SEQ ID NO: 10 below or a functional fragment thereof that is at least about 70%, 75%, 80%, 85%, 90%, 91%, 92%, 93%, 94%, 95%, 96%, 97%, 98%, or 99% homologous to such amino acid sequence. In some embodiments, gastricsin may refer to an amino acid sequence according to SEQ ID NO: 11 below or a functional fragment thereof that is at least about 70%, 75%, 80%, 85%, 90%, 91%, 92%, 93%, 94%, 95%, 96%, 97%, 98%, or 99% homologous to such amino acid sequence. In some embodiments, the systems, devices and methods disclosed herein utilize or comprise an aspartyl protease comprising any one or combination of SEQ ID NOs: 10 or 11, or a functional fragment thereof that are at least about 70%, 75%, 80%, 85%, 90%, 91%, 92%, 93%, 94%, 95%, 96%, 97%, 98%, or 99% homologous to any such amino acid sequence. In some embodiments, cathepsin E may refer to a nucleic acid sequence encoding a cathepsin E amino acid sequence, such as SEQ ID NO: 12 below, or a functional fragment thereof that is at least about 70%, 75%, 80%, 85%, 90%, 91%, 92%, 93%, 94%, 95%, 96%, 97%, 98%, or 99% homologous to such nucleic acid sequence. In some embodiments, gastricsin may refer to a nucleic acid sequence encoding a gastricsin amino acid sequence, such as SEQ ID NO: 13 below, or a functional fragment thereof that is at least about 70%, 75%, 80%, 85%, 90%, 91%, 92%, 93%, 94%, 95%, 96%, 97%, 98%, or 99% homologous to such nucleic acid sequence. In some embodiments, the systems, devices and methods disclosed herein utilize or comprise a nucleic acid sequence that encodes an aspartyl protease comprising any one or combination of SEQ ID NOs: 10 or 11, or a functional fragment thereof that are at least about 70%, 75%, 80%, 85%, 90%, 91%, 92%, 93%, 94%, 95%, 96%, 97%, 98%, or 99% homologous to any such amino acid sequence.

TABLE 2

| | Aspartyl proteases. |
|---|---|
| Name | Amino Acid Sequence (human) |
| Cathepsin E<br>SEQ ID NO: 10 | MKTLLLLLLVLLELGEAQGSLHRVPLRRHPSLKKKLRARSQLSEFWK<br>SHNLDMIQFTESCSMDQSAKEPLINYLDMEYFGTISIGSPPQNFTVIFDT<br>GSSNLWVPSVYCTSPACKTHSRFQPSQSSTYSQPGQSFSIQYGTSLSG<br>IIGADQVSVEGLTVVGQQFGESVTEPGQTFVDAEFDGILGLGYPSLAV<br>GGVTPVFDNMMAQNLVDLPMFSVYMSSNPEGGAGSELIFGGYDHSH<br>FSGSLNWVPVTKQAYWQIALDNIQVGGTVMFCSEGCQAIVDTGTSLI<br>TGPSDKIKQLQNAIGAAPVDGEYAVECANLNVMPDVTFTINGVPYTL<br>SPTAYTLLDFVDGMQFCSSGFQGLDIHPPAGPLWILGDVFIRQFYSVFD<br>RGNNRVGLAPAVP |
| Gastricsin<br>SEQ ID NO: 11 | MKWMVVVLVCLQLLEAAVVKVPLKKFKSIRETMKEKGLLGEFLRTH<br>KYDPAWKYRFGDLSVTYEPMAYMDAAYFGEISIGTPPQNFLVLFDTG<br>SSNLWVPSVYCQSQACTSHSRFNPSESSTYSTNGQTFSLQYGSGSLTG<br>FFGYDTLTVQSIQVPNQEFGLSENEPGTNFVYAQFDGIMGLAYPALSV<br>DEATTAMQGMVQEGALTSPVFSVYLSNQQGSSGGAVVFGGVDSSLY<br>TGQIYWAPVTQELYWQIGIEEFLIGGQASGWCSEGCQAIVDTGTSLLT<br>VPQQYMSALLQATGAQEDEYGQFLVNCNSIQNLPSLTFIINGVEFPLPP<br>SSYILSNNGYCTVGVEPTYLSSQNGQPLWILGDVFLRSYYSVYDLGNN<br>RVGFATAA |
| Name | Nucleic Acid Sequence (human) |
| Cathepsin E<br>SEQ ID NO: 12<br>GenBank<br>Accession No.:<br>NC_000001 | 1 atcattcggc cctcagactg ggctgggcag gtctgagagt tagggaaagt ccgttcccac<br>61 tgccctcggg gagagaagaa aggagggggc aaggagaag ctgctggtcg gactcacaat<br>121 gaaaacgctc cttcttttgc tgctggtgct cctggagctg ggagaggccc aaggatccct<br>181 tcacaggtga gaagacgtcc ccgcactgtg ttcagctggg tagtcccatg ccctgcaact<br>241 cagggctgct ctggggtagg aaagtgatg ggaggtgaa gaggaggaga agctgaggc<br>301 ttgcgtcaat gcatggaaga gactcatcca gtgaccgcct gtgtatggcc ttaatctcca<br>361 gtcctcaaca agtcatcctc ctgcctccac ctccacggag gtgccttccc aagtcccagg<br>421 ggtcttcttg tgttgcaaaa gagcaggaac ctgcagttgt ggtttgtagc tcaaagcgcc<br>481 ccaggacttc cccaggggac tgaccatcac tgtccccaag agttttttctg tccctttaaa<br>541 tcagcccttc gtgatgttca tgtaaaactg tagaccgccc cacatctccc attttcctag<br>601 atctcaaaga cctcagctcc aggaggggag ccatttccac tctaagattc taagactcta<br>661 tagggcagag atgaggccgg gcaggctgag tggcagagag gacgctgatc ccacctgtat<br>721 cctgcgtgct gtcttgcaga tccccccctc ccacccccatc ttctctagtt ggccctgag<br>781 aaaatgggac gagaatgggg ggaagaggga ggcagaagta catctcctgc ttacatgggg<br>841 gtttgtctgc agggtgcccc tcaggaggca tccgtccctc aagaagaagc tgcgggcacg<br>901 gagccagctc tctgagttct ggaaatccca taatttggac atgatccagt tcaccgagtc<br>961 ctgctcaatg gaccagagtg ccaaggaacc cctcatcaac tacttggatg tgaggcctcc<br>1021 tggggtcagg gctggggaga ggtgggagcg ggaggaaggc ccagcattag gcatggcca<br>1081 gtgccacatc agtagcaccg aaggccattg tggatttctt cacttggatg atgatccatg<br>1141 gggactgatt ccctgggtcc ccatgccatg ggctaagcag gccccccatg acccaaatgt<br>1201 cagagttctc tgcagaagga aagggctggg agtgaaagca tcatcccaca ctgaaggccc<br>1261 ctgcttctgc tctcagctgg gcagcttact ggctgtgtac ccttaggcaa gttacttaac<br>1321 ctctcccagc cccagttccc tggtctgtaa acagatggt tcttcctcca ctgcctctcc<br>1381 tacaatgtat ttataagaat caggttagtg caagtaaaat caaatgaagt agccagaggc<br>1441 ttggtttgat ttcctccttc atggccattt ctctgctcct tttaccttt attttccagc<br>1501 gttgccactt cctaggctct gtaaaactcca gtctgtatta ccccaggctc tggccctgg<br>1561 gagctttccc ctgcttcct ggtgagcacc cttgtccctc ccaccaccc acaccctctt<br>1621 tccttctcac tcttccttgc agatgaata cttcggcact atctccattg gctccccacc<br>1681 acagaacttc actgtcatct tcgacactgg ctcctccaac ctctgggtcc cctctgtgta<br>1741 ctgcactagc ccagcctgca gtaagtggg ccaggagcac cagcagagaa tgtctggggg<br>1801 ctagtcctgg gaggccaagc ctggtactct ggggaagggg ggcttaggtt ccagaaactg<br>1861 gccatccctc ccacaccagc ttccactctc catctttgag tcagccgtgg aactgcttat<br>1921 agcagagata gagcaaagcc aaggaagaac taaaatgtgg ctgctgtcca agagagtaac<br>1981 tttcatactg atcagaatta atagaaagaa agccattgaa aagagaaatc tttgacataa<br>2041 tgactcactt cctttggaac acccaaagga atgtagggga agtttaattt aattggttat<br>2101 ttctgagcag ggaggtgagt cgggttctag tgtagatagt ctgcttgttt caaggaggct<br>2161 tggtagcctt atctcctggt gcacacaggt ggggctggtg gggcacaatg gcatgggtgg<br>2221 gtccatttgt ccagaggtaa ctcagaagtt tcagtgagga ttggaaaaga agagctacag<br>2281 aaagatgtct tgttcgatac aggacaagtc ccagagacag aatgtctctg gaaaccccaa<br>2341 ggctagagat gtccatcggt tgggagaaaa gttgggagta atttcctggg gcaattgttt<br>2401 atccctgagt ttcttttgaa gccaacctct gacccacaat gggtggcagg gactgtggct<br>2461 ggcgcctgat aaatgacact tatcttggtg tgcctcatga ggtcattgtg gacaatcagg<br>2521 tttgctcagg gatagctatt tggtcccccag ttaggccaca tctgtagcta gagggaaatg<br>2581 tagttgttca ttagggaggg gcatcaccag gcttctaggg gccccactc agtgttgaga<br>2641 gctgagggaa gagaccctgc cgctgtgggg ctgggtggca ttagggcagg gatgcagcca<br>2701 gtgagccgat ggcataagca agagcagtgc acttcttcc agagacgcac agcaggttcc<br>2761 agccttccca gtccagcaca tacagccagc caggtcaatc tttctccatt cagtatggaa<br>2821 ccgggagctt gtccgggatc attggagccg accagtctc tgtgagtgca agtccttcat<br>2881 ttttctctc ttggacagaa acttgggaga cttattcaga ggtcttacat ttcaaatctg<br>2941 cctcaggaat gggtggaaac aggggttagc actaacttct aggagaaagg gcaagcaaca<br>3001 ctcccccacct gagatggtgg cagtgggtca gtctccacag cacgctgggc cctgggggag<br>3061 agcagcacag ggggactctg gcaggaagca gtgcccagtg cacaaagcct ggtggcaggg<br>3121 tgcacagctg gatctccagt tctagggca ttgaggagat aaaaccacgt ctccgtcttg<br>3181 aaggataaag aagtccacac caggggggaga gatttggact cagtaacata aggggggcaag |

TABLE 2-continued

Aspartyl proteases.

```
3241  gtctgaaatg ggagtccaat cacagaggca aggcagaagc ccagttgtcc aaaggccaag
3301  gtccaaactg aactcagtgc tgagctcatg agctgttcct caaactccct ctgacctctg
3361  accctctgac tccctctgaa gtcctatggg tcctagaact atgggaatca gacaaatgtg
3421  gggacagaga gccaggtact ttttcaggct tatagacagc aatatatgcc tgggccttgg
3481  gagaaagaga ggttgaccta ctcctggtga acgttggtcc ctggggtatt cccgaggcca
3541  gcagggcaca gccttcatca acatccctta gagtgggtgg agtaggacat attatcaact
3601  gaaagaatgc cagaagcaga aaaacaccat ctatgtaaaa atatcataca gataaaacaa
3661  tgtactgtat tttctattgg aactatgtat gcgtgtgtat acacacatta catatataat
3721  atataatata taatatccat atatgaatat atgtaatata cagtatattt gtatatataa
3781  tatatatcca tctgtatata ttatatagat acaaatatgta acatattaaa gtatataata
3841  attgcataat tatatcatat aatacatgtt atatattata taattaatat aaatatgtaat
3901  acattacatt aatatatgtt ataatatata taatatatta tagaatataa ttgatataat
3961  gtattacatt aataatatag tatgtgttat ataatatatt aatatgttgt atgtaataat
4021  atattacata atatatattatg ttaatctatt ataataga ttaacctatt ataataga
4081  ttaacataat atattacata atattaat ctattatata atagattaac acaatatata
4141  tgtaatgtgt atatattatg ttatatataa gattctatat atattatgac atatacatat
4201  atattatata tctaattaca tataatatat atataaaagt taaaatgact attttgaagg
4261  ctacatccct aactgatcat cacagtaacc tctgagatgc agggaaggga ctgaaattag
4321  catagaaagg ggaattcaag cctatagctt gtcacgtatc tgttggctca cctggctggt
4381  gtagggcagc agccaagccc acagcaatgt cagctgcatt gctccttccc tcagttttc
4441  tggctccagg accaggtgtg cacttaccta taacaaatca tcagcttttg ctgcataaca
4501  tccccatcat tgaggctgga gacttgggga cagtgagaga acaatgtggg ttccagtcca
4561  ccctcaccct catgggttcc aactgggcct ttttctccca cttgacatct atcttccctt
4621  tctgctgtgc aaactgtaga ctgctgctgc agcatcagga cagaaacagt atcctaaagt
4681  acactgttta actagcaccc acagttgcat ataatcaata tctatatcca catcattata
4741  gctatatcta taatctatag tacctcctaa tggttctgct tctcttatca aaccctgact
4801  gacataataa agatatgaca tgtgaaaaat tgtagatgaa gctgatgcag ccctttaaagg
4861  gaccatttag cctaaaatgc atgcgttgtt aatagaaatg ctaatgatca attatctaag
4921  ctcctatttc aagaaatgaa taacaagaaa atgagcaaac cgtaaacaaa caatagcaaa
4981  tcaacccaa agaaatcaaa aggaaggaaa taataaagag tagaatggga cacaaatgaa
5041  atagagaaat cacacagtac agaaaattaa caaagccaag aatgaactct ttgcaaagag
5101  taataaaatt ggttagcctc tcacatgact aaataagaaa aaagaaagaa aatacaactt
5161  aacaatgtta gaaatgagaa agagaacatt agtaaagtta tcaagaataa ttttatattg
5221  ataaattta caattttcag aaaatcaaca aatgccttga gaaatacagc ataccaaaac
5281  tgatgcaaaa acaaaaaata gaaaatgtga atcttttaaa gatatactct gttattaaaa
5341  aatctttcca caaagaaaac tccacgaaga aaagcctcac tgataaattc tctcaacact
5401  aaaaaaaatc agtctttcac aaactcttcc agatatttga caaagtaaaa acactttata
5461  actcatttta tgaaaccagc ataacttaaa taatgaaact tgaaaaggac attataacaa
5521  aagaaaatat aaaattacag accaatctct tctctcatga atatagatgc aaaagttcta
5581  aatgaaatac tagcaaataa aatcttttg tatataaaaa gatcatacca agggtcatct
5641  ttccaggaat ttatcattta acagaataaa aggagaaaaa tcatatgacc aatatgatta
5701  tattagtagg ttaataacat tcaatatcta ttcatgactt caagaaaaac tcttagcaaa
5761  ctaggagtag aaagtaactc ccttaatctg ataaaaatga aggacttcat ctaaaagaag
5821  cccacagcaa actttatact taatggtgaa ttgtcgagag acttctccat aagatcaaga
5881  atgagacaag gacactcaat ctcaccactt ctattcaaca ttgtactgaa aatcctagcc
5941  agtgcaacaa ggcaagaaaa aagaaataaa gaacattaag atggaaaagg aagaaataac
6001  tctgtcaata ttaatgtatg acaagattcc ataagtagaa aatccaaaaa tatctacaga
6061  aaggatattg ggattaatat gtgaacttag cgaagttgct ggatatgagg tcaacataaa
6121  aaaaatcatc tggggccagg cacagtggct cacgcctgta atcccagcac tttgggaggc
6181  cgaggcaggt ggatcatgag gtcaggagtt tgagaccagc ctgaccaaca tttctctact
6241  aaaaatacaa aaattagcca ggcgtggtgg cacacgcctg tagtcccagc tactcaggag
6301  gctgaggcag aagaactgct tgaacccagg aggtggaggt tgcagtgagc caagatcatg
6361  ccatggcact ccagcctgag tgacagagtg agactctgtc tcaaaaaaaa tcatttggat
6421  ttatatatac aggttatgga tccttatccc aaatgcttgg gaccggaagc cttttagatt
6481  tcaaattttt tcagattttg aaatatttgc attatactta ccagtttagt atcccaaatc
6541  tgaaaatcca taatctgtaa tgctccaatg agcattttct ttgagcctca tgttggcact
6601  caaaaagttt tggattttga agcacttcag tttcagattt tcagatttgt gatgctcaac
6661  ctgtagcaag taaaacaaat ggcaaataga tttttaatga cactatttat aatactatca
6721  aaccatcag ctactttgat gtaaatttaa caaaaaatgt gcgagaactc tactctgata
6781  atagcaaaca ttactaaata aaagtaaaag acttgcataa aaatcacaaa cattaatgaa
6841  taaaattaaa agaagacctg tattgaaaac taaaccatgc tcatagattg aatgactctg
6901  tttcattaaa aagtcaaatt ttttcaaatt ggtctataca accaattta ttccaatcaa
6961  aacaacagca tttttttctta gacattagca aactgattct aacatttata tggatatgta
7021  atacaccaat acaatcttgc tgaagaaaaa cactggtaaa tattaagatt tattataaag
7081  ttacagtaat gtagacgtgt ggtgttggca cagaatttaa aaaataaaca aatgtaacag
7141  aacagaaaat acaaaactat caacacagtc atctgacttg cgttgaacaa gatactgcag
7201  tatgtggagg aaatgatggt atatttatta aatagtgcca ggtcatatga atatccagat
7261  agaaaaaat aaatcttaat tcctaccttta cacattatca catttcatat aggttccaga
7321  tcgcaatgtg aaaagtaaac aataaagctt ttagaagaaa acatgagaaa atgttttcat
7381  gaccttaagg taggcaaaat ttctgaaac aagttacaaa aaaacagtgt acaataagca
7441  catgatgagt gacagaagcc agataccaaa gagttcatat gggatgattc catttatata
7501  aaatccaaaa aataggcaaa accaatatat gttattagaa gtcaggagac tggctcttct
7561  tgaggagggg cgcaatgatt ggcaggtgca tgaggcttc tgaggtttgg aatgtcctgt
7621  ttttgggaa tatagcaagc atctttgtgc tcatttagtc aaggaaagtt gggaaggaga
7681  ggcattagct tcaagacaga ggaaaatcca ggagtcaaac cctttgccag caatcccctg
7741  tgccattctc ctgttctcct gtgggctttc tcctaccagg tggaaggact aaccgtggtt
7801  ggccagcagt ttggagaaag tgtcacagag ccaggccaga ccttttgtgga tgcagagttt
7861  gatggaattc tgggcctggg ataccctcc ttggctgtgg gaggagtgac tccagtattt
```

TABLE 2-continued

Aspartyl proteases.

```
7921  gacaacatga tggctcagaa cctggtggac ttgccgatgt tttctgtcta catgagcagg
7981  taaggcccat caagtctgtg aggttaaagt cagttataac tacagggaga caacacatac
8041  acttgactta gcagtcaaaa gacctggttt aggtagcttg gtccattacc agctgtgtga
8101  tcttagtcaa aacatttaac ctctctgaat attgaggaaa tgggatttgc ttcatcaagt
8161  agctgtaaaa acactttgta aactctacca cactggctta aatttaagga atctctggga
8221  ttggttcttc attgatgctg tcactaaata tcaagctcct attatatgct gattatgatg
8281  ctcacactgg ggacccagtg aaacaagaaa gacagtacct gcaggaggag gaggcagaaa
8341  aaaatgaaaa gctgacaata aaataattgc atgctgatgg atgaataaac aaaatgtggc
8401  atatccaaat aatcaaatat tattcagcct taaaaaggaa gaaaattctg agacatgcta
8461  caacatagaa gaaacttgag gacataatgc taagtgaaat aagctagtca caaaaagaca
8521  aatactgtat gattccactt aggtgaggta cctagactag tcaaattcat aggcagaaag
8581  tagactgcca gttgccagag cctggggagg ggaagtgagg aattcttaaa ccgttgttga
8641  tggcctaatg ggtataaagt tccagttctg taaaatgaaa ggtctggatt ttacaacagt
8701  gtgaacatac ttaacactac tgaattgtag actcaaaaat gggtaagata gtacattta
8761  tgtgacatat ttttacaaca attttaaaa ttgcacattg tttttggaaa aggtcatgag
8821  gctcacctgt ttctaggcac tcttgcccgg catccttgga gggtcatctc ctcttcctcc
8881  ttacacagga aggtgatttc tgaccttgct gactttttcc agctcagacc tggcctgcgt
8941  tcacactgtt tcagcataag cccattcctc tcattcccct ctcccacatg gagggtcctg
9001  gattttccct atcaagctat gtttcctctc cagcatgaca gcactcagga ccaggcctag
9061  gaagagctgt gagtaagaga ggcaagttgt ctagacacct ctgcttcccc ttgcagaact
9121  tccttctccc gtcgcctggg aaaagtgggc tgtaatggag aatatcaagg cttggcagtc
9181  agactggcct ggatttgaat cctgccactt acattgcttc atctcactga ggctcagttt
9241  cttccacgga ccactaggtt gatgtgagtt aaataagttt agacagataa aatccccact
9301  acacggcctt gcaccaaggt aatcaacaaa tgtgagttcc tttccccact ccctctgtaa
9361  aaccactgtc ctaaaattcc tacaggtatt cactcctctc cctctttacc accctgattt
9421  cagttttgta tctttctgat ccttttcctc ctcaaaatga atctgtctta ggtcctattt
9481  ctccagagtc ctgctaggtt ccagaacata atctgagaaa tcaataccaa tgaaaataag
9541  ttttcaggct ctagtaagtc atgatacatt catattagcc tctttgcctt aacataagga
9601  gtgaataaca caaaaacgcc aggcactgtc acaaccatag tggggaagat actttgggaa
9661  aaggtgtctt tggggggttgc ttcaagccac acagtgtata cccacccagg atggtcctgg
9721  ccttggttct gaatgacaga cctgctggcc ccatttccca cctccttaac cttttttatcc
9781  aagaagcaga aacacattca caaatggtca aggggagttg tttctaacct tgtgtcaaaa
9841  aggcccagac caattcactt gcagtagtca gagtcccggt ctcaaagccc agactgatgt
9901  ttctgcctac ctgtgtgctt ggcatgagac caagaagcaa agggtcctag ctgaggctca
9961  cccctagagt tttgcagtgg cccttcctgg acagtttgtc tttctctcca tgtagtaacc
10021 cagaaggtgg tgcggggagc gagctgattt ttggaggcta cgaccactcc catttctctg
10081 ggagcctgaa ttgggtccca gtcaccaagc aagcttactg gcagattgca ctggataagt
10141 gagtattccc catgaagtag tgacagtact aggggtaaac tgaaaagagg cacaactcaa
10201 accgatttaa ctgaaaaacc actggtcact agcagaggat gccagaagct tactgtggtt
10261 ggaggtatgg aggtgctgag caagtgtgca ggaagggacc tctgtaacca gggcagcaga
10321 cacagcttcc ttccttgtac acatggcgtg ctttttaactc aacatacagt caataccagt
10381 gcacagcctg ctccccttg ttcttttaac attaacacac aaggcaaggg atgagtaaca
10441 tggggggttg cacaggtgaa ttgggctcag atcttgtcct caaaaaactt gtacagaaga
10501 tgagatgcac ccaaaccact atcctgtaaa atggaaggtg gtcagtgctc caagagaggt
10561 gccaccaatg tggtccagca gacaggcatg accgcttcta tctgaatgct ccagtgcatc
10621 atggaggggg ttacattgaa actgagccag gaaatatata caatatctgg gcacgaagca
10681 attggggaag tgggactaca tgcctgcctc ataccctagcg ccgtgctaga caatgcagga
10741 attggaaaag tgtagttcaa gtttcaattc agctaggatt gagttcctgc aaggtaccag
10801 gcattaggaa tgcaaaaaat aaaaggcctc aatgctcact gtctattcag agttttcaa
10861 actgtaggaa ttcacctatt tatgggtcat gacatcattt tagaagatcc tgacctgacc
10921 aggtgtggtg gctcacacct gtaatcccag gactttggga ggccgaggca ggtggatcac
10981 aaggtcaaga gattgagaca cctacatttt ttagacgaat tggaatacag tagaaaatac
11041 cagagtgcac ttcaattgca tgaatgtgtg tgtgtgtgca ctgggtcaag aagtaaacag
11101 atttcttcct atggatctca gtagaaaaca attgaggaac actcatatgg tgggtggaaa
11161 tcattgatgt gctccaggca tttgagaggc caaaaaagag tgggagtttc ctaggagccg
11221 ggggagggaa ggtgggccga ccacaaccct gtcccctcag catccaggtg ggaggcactg
11281 ttatgttctg ctccgagggc tgccaggcca ttgtggacac agggacttcc ctcatcactg
11341 gcccttccga caagattaag cagctgcaaa acgccattgg ggcagccccc gtggatggag
11401 aagtgagtgc ctgcctgcgc aagggagtgg tggggacagg agagccaggc cttctcttgg
11461 gaggtggcaa ggctctaaac ggatcctccg tattgggttt tagtatgctg tggagtgtgc
11521 caaccttaac gtcatgccgg atgtcacctt caccattaac ggagtccctt atacccctcag
11581 cccaactgcc tacaccctac tggtaagaac tgtttcctta ttctgcaggc cacagggccc
11641 tccccacatg cctgccactt ccccttttca atcgcctgca ctttgcccgc ctttacccta
11701 agccccgccc cacgttgttc tgctctcatg tggcattccc tctgggaggg acacagctgc
11761 ctgtggtgga aagaccacgg ggcttgctct aatttccagt tctgccatga agcagtagtg
11821 aacttcaggc aagccattta aggaagtctt ctgatattgc catgtagggc ttttccactg
11881 acaaagtttta atctcctcaa ccaccaggtc agactggagc tattactatc tcattttata
11941 ggtgagaata tcaagactca gagagtcaaa taaatggttc aagatatgag ctgtttgcag
12001 ggaggagtgg agaataagat tatattttgtt ctaacttcaa attaacattc ctcctctagc
12061 aagaaaatgt cttttgttgc agtaaattct caagtttgta gggtgaagta gaaagggaac
12121 tcccagacct tttggacacc tatgagcacc tcacaccaca gttggtctga attttcagca
12181 ttctaggtat tcggcaccac acttcaacac actaatttt ccaagagtca ctcacagcat
12241 cagggtgact gcatcagaag agggggtcta aggtatagac tgagggcttc agccctaccc
12301 ctaagcctct attaactcct tcccaaagcc accaacagac aatccaaata aaaacaaatg
12361 tttgctttaa aacacagctt catggtaagt ccctaagct cctgccacat agggattatg
12421 gagctgccac tctgaacacc acactgagga ccagtgagac atttagactg agccctgttc
12481 atcagtccac atgcccatca acaccccagc acacccacac tctcaccttc ccccacgtga
12541 gttgagtccc tgcccaggtg gaaatcactg atgtgctcca ggcgctggag agcccaaaaa
```

TABLE 2-continued

Aspartyl proteases.

|  |  |  |  |  |  |  |
|---|---|---|---|---|---|---|
|  | 12601 | agagtgggag | tttcctagaa | gccaggggag | gggaggtgcg | tggttctttc ccggtatggt |
|  | 12661 | gagtggttct | tttagaagat | cattttagaa | gatcatgacc | tgaccgggca tggtgactca |
|  | 12721 | cacctgtaat | cccaggactt | tgggaggccg | aggcgggtgg | atcacaaggt cttgtgctgg |
|  | 12781 | ttctttcgca | gtacagtgag | tggttctttc | ccaccagcag | atttcaatca gagccacctt |
|  | 12841 | gatccatcaa | aactgctgta | aaaattttga | cttttcacgt | ccttcctctc aagaagtctc |
|  | 12901 | cctgagccct | ctgcaaattt | tcccacaccc | tcatcagcaa | cttcacattt caaatcattg |
|  | 12961 | ttggaaagac | cacacttgcc | tggtagagca | cgtctttgcc | aaactaaaaa ttagattgga |
|  | 13021 | gaaggtgaca | ctcttctctt | gaacaaggaa | tgcctacttg | cctcatctaa aggggggtcac |
|  | 13081 | tcaaatgttt | gtttccagaa | catcaacaag | aaaatagcag | tggatagcca ctaacacagt |
|  | 13141 | tctttctctc | ccttaacaaa | aactaagctg | agcttcacta | gaaactaaag aaaccagaat |
|  | 13201 | ttaaaccaag | gtcttccggt | gccaaccctt | ttgctctttct | agccatgcag caagggtttc |
|  | 13261 | ccagttgtaa | aatgatggtg | acaggggtag | gtgggagtat | ataacagatg aacagttctc |
|  | 13321 | aaaattgtag | aacatagacc | ccaggcccat | aagaatggac | ttgtgcagac aaacacttta |
|  | 13381 | ttaagcaacc | tagggtaggg | acatatgaag | caggaggaag | aacccaccga ccaaaatggt |
|  | 13441 | ggaacccacc | agctgtccaa | ggccacccag | tgccagccac | caccaccaca caggcagcct |
|  | 13501 | ccagcagta | ctactacctt | cttcccccgt | ttgtcatttg | catccttctt tccaacccac |
|  | 13561 | aggacttcgt | ggatggaatg | cagttctgca | gcagtggctt | tcaaggactt gacatccacc |
|  | 13621 | ctccagctgg | gcccctctgg | atcctggggg | atgtcttcat | tcgacagttt tactcagtct |
|  | 13681 | ttgaccgtgg | gaataaccgt | gtgggactgg | cccccagcagt | ccctaaggga ggggccttgt |
|  | 13741 | gtctgtgcct | gcctgtctga | cagaccttga | atatgttagg | ctggggcatt ctttacacct |
|  | 13801 | acaaaaagtt | attttccaga | gaatgtagct | gtttccaggg | ttgcaacttg aattaagacc |
|  | 13861 | aaacagaaca | tgagaataca | cacacacaca | cacatataca | cacacacaca cttcacacat |
|  | 13921 | acacaccact | cccaccaccg | tcatgatgga | ggaattacgt | tatacattca tattttgtat |
|  | 13981 | tgatttttga | ttatgaaaat | caaaaatttt | cacatttgat | tatgaaaatc tccaaacata |
|  | 14041 | tgcacaagca | gagatcatgg | tataataaat | cccttcgcaa | ctccactcag ccctgacaac |
|  | 14101 | ccatccacac | acgccaggc | ctgtttatct | acactgctgc | ccactcctct ctccagctcc |
|  | 14161 | acatgctgta | cctggatcat | tctgaagcaa | aattccgagca | ttacatcatt ttgtccataa |
|  | 14221 | atatttctaa | catccttaaa | tatacaatcg | gaattcaagc | atctcccatt gtcccacaaa |
|  | 14281 | tgtttggctg | tttttgtagt | tggattgttt | gtattaggat | tcaagcaagg cccatatatt |
|  | 14341 | gcatttattt | gaaatgtctg | taagtctctt | tccatctaca | gagtttagca catttgaacg |
|  | 14401 | ttgctggttg | aaatcccgag | gtgtcatttg | acatggttct | ctgaacttat cttcctata |
|  | 14461 | aaatggtagt | tagatctgga | ggtctgattt | tgtggcaaaa | atacttccta ggtggtgctg |
|  | 14521 | ggtacttctt | gttgcatcct | gtcaggaggc | agataatgct | ggtgcctctc tattggtaat |
|  | 14581 | gttaagactg | ctgggtgggt | ttggagttct | tggctttaat | cattcattac aaagttcagc |
|  | 14641 | atttta |  |  |  |  |

| Gastricsin SEQ ID NO: 13 GenBank Accession No.: NC_000006 | 1 | cttcactcca | ctgcgactgc | agaactcaga | gctgctcttc | ctctgtggcc agttggggac |
|---|---|---|---|---|---|---|
|  | 61 | cagcatcatg | aagtggatgg | tggtggtctt | ggtctgcctc | cagctcttgg aggcagcagt |
|  | 121 | ggtcaagtga | gtctgggatc | tggctgctgg | tgcaggggagc | ctggatggga gcctaaagcc |
|  | 181 | ctgcaaaggg | caactggcc | aggggacacc | ctgcctgtct | ctactctgca acttctgcta |
|  | 241 | ggggaaggga | agtctccctt | tgctgatgtt | agacaggaca | catggtggga aggagacaca |
|  | 301 | gcccctgcct | tcaggaaact | tcctatcaaa | gggaaaagca | cgatcccttc ccccatctga |
|  | 361 | tgaggaaaga | tggacctgaa | acagaggtgg | taagggtgac | tactgcccaa gcagcccttg |
|  | 421 | aatggcaggt | gtggattctt | ctcacagaag | ggagcaatcc | tttttggata agggatatct |
|  | 481 | tatccactat | cctctctaaa | agttgcttta | aggctgaaaa | tttactggca gatgccaaaa |
|  | 541 | tcatctaagc | agaaacacca | gtaaatgtaa | atctctacac | ctgaggggtc aggagaaaac |
|  | 601 | tctggagtag | atggcatggc | tcacaggcca | tcaggaaggc | gcccagcctg ccatcctgcc |
|  | 661 | tgttatttct | ctacccaaga | gtacttcctg | aggccaagag | ctggctcctc tcagaaactc |
|  | 721 | ctatcaatat | gcatatttgg | tagaggtggt | taattagtct | tcatagctca gggtgaaggg |
|  | 781 | gtttagcaga | gaatttctgg | agaatgcaga | gtccccaggg | aatggggatt aagcagaatt |
|  | 841 | ctggagccta | gagcaaggcc | agagtggacc | cctagagact | cccaagcaat ggcagcaagc |
|  | 901 | aagtctggga | aggagagtgc | cgagggtgtg | actgagccca | taggatggga cagaaacggt |
|  | 961 | gatttataag | ttccaactcc | agagctgatc | tgtgctccag | accacccagg ccaacttccc |
|  | 1021 | gtggtcctgg | tgtcctgaga | ggagcagtga | tggggcctag | gccatgcgat tagcagctgg |
|  | 1081 | gacagaacta | ggactctgtg | tcctgagtcc | cagctagtgc | tgttgccgtt gctccatgct |
|  | 1141 | ctgtcacatc | cagctggtgc | caggtgcctg | agggctgccg | tagaaaggaa ctctggggtg |
|  | 1201 | aactttgcca | tctctgaaat | cttcttttgtt | ttttttttg | aaacagaact tcgctcttgt |
|  | 1261 | tgcccaggct | gcagtgcaat | ggcgcgatct | cggctcactg | aaacctctgc ctcccaggtt |
|  | 1321 | caagcgattc | tcccacctca | gcctcccgag | tagctaggat | tacaggcatg cgccaccatg |
|  | 1381 | cccggctaat | tttgtaattt | tagtagagat | gggttttcac | catcttggcc agtctggtct |
|  | 1441 | cgaactcctg | acctcaagtg | atccaccgc | ctcggcctcc | caaagtgctg aggattacagg |
|  | 1501 | cgtgagctac | cgtgcctggc | ctgaaatctt | ctgttaaaaa | tgtgcatttc ctgggctggg |
|  | 1561 | cgcagtggct | cacgcctgta | atcctagcac | tttaggaggc | caaggcgggc ggatcatttg |
|  | 1621 | aggtcggag | tttgagacca | gcctgaccaa | catagagaaa | ccctatctct actaaaaata |
|  | 1681 | caaaattagc | tgggcatggt | ggcccttgcc | tgtaatccca | gctactcagg aggctgaggc |
|  | 1741 | agaagaatg | cttgaactcg | ggaggtggaa | gttgaggtga | gccgagatca agccattgca |
|  | 1801 | ctccagcctg | ggcaacaaga | gcgaaactct | gtctcaaaaa | aaaaaaaaaa aactacatat |
|  | 1861 | cctgggccag | gtgcggtggc | tcacacctgt | aatgccagca | ctttgggagg cctaggcagg |
|  | 1921 | cgagtcacga | ggtcaggaga | tcaagaccag | cctggccaac | atagtgaaac cctgtctctg |
|  | 1981 | ctaaagatac | aaaaaattag | ccaggccatg | tgacaggcgc | ctgtaattcc agctactcgg |
|  | 2041 | gaggctgagc | aggagaatt | ttctgaaccc | aggaggtaga | ggttgcagtg agcggagatt |
|  | 2101 | gtgccattgc | actctagcct | gggtgacaaa | agtgaaactc | cgtctcaaaa aaaaaaagt |
|  | 2161 | acatatcctg | aaaagggtaa | agaactaaag | ccctccttcct | ttcctggtgg ggaatctatg |
|  | 2221 | ggatatttga | cagcaaaggg | ccagggagat | aggagggacc | ttgagatgag gtgaggagtg |
|  | 2281 | catgcatggt | gaaatgaatg | gttttctgaa | tcttagagca | agtgctgaga agagctttgt |
|  | 2341 | aagaaagagg | ggaagaggca | aagggaggaa | gaaacacgcg | cgcgcgcaca cacacacaca |
|  | 2401 | cacacagaga | gacagacaga | cagagacaga | gagcaaaagg | ctgagagaga gaaaaagaca |
|  | 2461 | cacacagaca | aggggggaaca | aacagagtgg | cagggaggtt | gaagcatgca gttaagagaa |

TABLE 2-continued

Aspartyl proteases.

```
2521  ggagagagag aaagagagga gtgggaagag aggaaggagg gagggccttg cctcatatgc
2581  aacctttctg tagagtgccc ctgaagaaat ttaagtctat ccgtgagacc atgaaggaga
2641  agggcttgct gggggagttc ctgaggaccc acaagtatga tcctgcttgg aagtaccgct
2701  ttggtgacct cagcgtgacc tacgagccca tggcctacat ggatgtgagt cctgaccctt
2761  tctggcggta gccttctctc tggtgtgggc tggagggaag gggcaggtcc cttcactcct
2821  ctgcccatgg aggagcctgg ggcccctgga tccctctgga actaacagct tgctccatgg
2881  cccccaggct gcctactttg gtgagatcag catcgggact ccaccccaga acttcctggt
2941  ccttttttgac accggctcct ccaacttgtg ggtgccctct gtctactgcc agagccaggc
3001  ctgcagtgag tgctgggctg gcagagagg ggtggttggc agggcaaggc actgataccc
3061  tctggggagg gccaaacttc cagagggagc tcaggactga ggggagctca gtcctgggga
3121  ggaccaggga catgtgcagg gccacacagc atgcccaagc cagaggaaag atgctggtcc
3181  tgcagctgga tggccccttt gccttccctg ccaatatgta tccctttgct tatgccagcc
3241  cctaactccc cactcccttt tattccactc tccccattct gtttactctg ggcagtgcca
3301  ttccattcca tgtgactaat ttccagtcca ttccatccca ctccatccca ctccattcta
3361  ctccattcta ttctgctcca cctcagtatt tactaagttc tcactgagtg tctccaagag
3421  acacaacaga acaatatagg atgtgggctc cgtactatag tggttttggg agacaggcag
3481  tgtttgcttt cttaaggttg ccttggtccc tgctgaagcc ttggtgtttg ggtcctgata
3541  cctttggccc aaggggtccc ttgatgtccc caccctatgt tatgactggc ttcttgatga
3601  gtgaaggtgg ggagtacttg gggatgccct ggagggctgg ggggaatgct gggatgtggt
3661  gcaggcccat tcacttcttc atctgatgag taattactca gcactgctgt gagccacgtg
3721  ctttgctggg gaccagggac tcagggctgg gttctctgca aacctgtcca cagggaggcc
3781  acagtcctga ggcatcccaa gattctgtaa gtcagaaggg gctttgggga caaggctggc
3841  cagctcccat gggccttcca atgccaccct ttgacttggc aaccagggat gctgaggtcc
3901  caggatgtga gcgcagcctg agcgagaggc tgaggtggga acccggcagg cctgagagct
3961  gagcagccct gccccagccg gcctgactcc ccatgccctg actccctgc agccagtcac
4021  tcccgcttca accccagcga gtcgtccacc tactccacca atgggcagac cttctccctg
4081  cagtatggca gtggcagcct caccggcttc ttttggctatg acaccctgac tgtgagtggg
4141  catgggagt ggaggctggg gctgtgagct ataagctgga ggggacagtt agatggactc
4201  tcctgaaaca cggtggaatg ctagtgttct ggtgtgcagg acaggaaggc aggacaagac
4261  aggtccattc agtcactccc ccaacactca ctggtggcca ccatgtgcta ggcactgggg
4321  caccatactg aacaagaggg acatggtcct tttccttaag aagcataagg cctggggagc
4381  tcagagaaga aggagacggg tgaggaagtg agctgtggca gtcaaggaag gctacgcagg
4441  agaggtggct cctgcaacac ctgtcaagag gcagaggtgg ctggctacgg tggctcacgc
4501  ctgtaatccc agcactttgg aaggccaagg cgggcagatc atgaggtcaa gagatagaga
4561  ccatcctggc caacatggtg aaaccctgtc tctattaaaa gtacaaaaaa ttagctgagc
4621  gtggtggcac gcgcctgcac tcccagctac tcgggaggct gaggcaggag aatcgctaga
4681  accaggggag cagaggttgc tgtgagctga gattgcgcca ctgcattcca gcctggtgac
4741  agggcgagac tctgtctcaa acaagcaaac aaacaaacaa gaaaaccaaa acaaaaaaga
4801  aggggcagaa ggtgaggaag ggatgaacag aggcttgagg agtctctagg ggaacctgga
4861  ggaggtgagt ggagtcagac tggtccattc ccctcgtttg tgtctccatt aggtccagag
4921  catccaggtc cccaaccagg agttcggctt gagtgagaat gagcctggta ccaacttcgt
4981  ctatgcgcag tttgatggca tcatgggcct ggcctaccct gctctgtccg tggatgaggc
5041  caccacagct atgcagggca tggtgcagga gggcgccctc accagcccgg tcttcagcgt
5101  ctacctcagc aagtgagcaa ccagctggcc agtcccacc tcccgggatg ctccccgag
5161  cgccctggac gactgaggct cagtgctcaa tgctttgggg tttggaggca tcccagcggg
5221  catctggctc cagtcagtct tgctccaggg ccttccttcc tgggcttcct ctcgaatcct
5281  ctcccagcca cccgaccaca ccccatccct gcacctgtcc ccagtcccct ccgacttgtc
5341  tttgcattcc atggccacga tggaatgaat tcttccaca gcagctgaac tttgccctga
5401  gttttgctgc tctgattctc agcacccctt ggacaggctt cctggtggag aagcgggtgg
5461  ggcagttcgc tcacttcctt ctgaccgaat gttttctacc tgtatccctc ttttgcatag
5521  taatgtattg cttcatctcc ttttatctat tgttctagcc tggtcctgga gtcttctggt
5581  ctaggtccac tgctgacccc tagcaggttg ttatccttgc cagtcaacac aagcatgtgc
5641  aggcatttag tgagacaggc agtgggtggg ggtgagcggc ctggggcctg cttttctttg
5701  ttcttcttca gaattaacca gcaacttgct tttgtttttgt tttgtttttgt tttttttgaga
5761  tggggtctca ctctgtcacc cggtctggag tgcagtggcg caatctcggc tcactgctac
5821  ttctgcctcc cggattcaag ctatttttcca gcctcagcct cccaagtagc tgggattaca
5881  ggcatgcgcc actgtgttcg ctaattttt gtgttttag tagagacggg gtttcaccat
5941  gttggccagg ctggtctcaa actcctgacc tcaggtgatc cacccgcctc ggccttccaa
6001  agtgttggga ttacaggtgt gagccactgc gcccggcctt aggcagccac tttctagaga
6061  cagttagctt cattggacta atctgggaa tctgaagttc aaggacctca ccctgttact
6121  aatgttgcta acttcctctc cacctctgtt tatgattcct ctgcgtgtaa acagagcagc
6181  tccacccagc tccacactcc agctaccaga gaagcctctg gaacaaacat ggaatatcct
6241  tacccccttc accaagaccc tacctgtctc caatctcagc agaaaagtaa caagctgggc
6301  cggggtgggg atcccggtga catgtctacc agaggcagga agcggagggg agaggagagc
6361  agagtgtggg ctgggggtca caaccactag gggaccccc agaagtcagc atcattcggg
6421  agcctgaggc gctgggaatt ccaaggcctg gccagaaagc cccagtctaa gggacgcatc
6481  ccagtcccca gggagcccca atctaaggga tacagcccca tcctcaggga gcccagtct
6541  gagggagaca cagactcgtc ctcagggagg cccagtctaa gggacacagc cccatcctca
6601  gggagctcca atctaaggga tacagccctg tcctcaggga gcccagtct gaagggagac
6661  tcagtgctct cctcagggag ccccgtctg gatcagggaa ggagctctgt ttccctgtgg
6721  aggtgactgc tcaggaggaa agtccttttc catggcactc cctgacttcc ccttcccttt
6781  ctctcctgca gccagcaggg ctcagcgggg ggagcggttg tctttggggg tgtggatagc
6841  agcctgtaca cgggcagat ctactgggcg cctgtccacc aggaactcta ctggcagatt
6901  ggcattgaag agtgagtctg ccgttgggcc ctggggatgt ggcacttcct tggagtgggt
6961  ttccaggcca tgtcacacac acacacagtc tggcactgct ctgggatggg gcagaggacc
7021  cctgaggctt actcctacaa agccacaact gtcctctgca ggggtgacaa gcccagctc
7081  agcctggaga agagagtgga tgtggacaac atagggaggg gcaggacctg gactcccgaa
7141  cattagggac cctgcagtcc agccccatca tgggctcaca gattagaaac gaaggtgtgt
```

TABLE 2-continued

Aspartyl proteases.

```
7201  tagcaactaa tttgctcaaa gtccttacaa tgaatcagtg gacctggttt tcagtgtttt
7261  tagaaacttc cttgacactt ttaaggacta ggtcccatgg catgatgcag gggaatagcc
7321  ggattgatct ttgcagggtc ctcactttcc tcaagaaagt agctgtagct ctttgtccca
7381  cagtggtggg gaaagcccgc cccagctgcc ctgaactggg ggagtcctga ggctgcctgt
7441  cttctcccca tacaggttcc tcatcggcgg ccaggcctcc ggctggtgtt ctgagggttg
7501  ccaggccatc gtggacacag gcacctctct gctcactgtg cccagcagt acatgagtgc
7561  tcttctgcag gccacagggg cccaggagga tgagtatgga caggtgtgac tggtgagggt
7621  gtctctcttc cccaggaggc tactccagag gcattcatga tttctcctgg gaacacaata
7681  gccagctggg cgccgtggct catgcctgta atcccaacac tttgggaggc caaggcaggc
7741  agatcttttg agcccaggag tttgagacca gcctgggcaa catggcgaga ctctgtctct
7801  acaagaaata caaaaattag ctgggtgcgg tggcatgcgc ctgtagttcc agctacttgg
7861  taggctgagg tgagaggatt gtttgagccc aggaggtgga ggctgcagtg agccgtgatc
7921  tcactattgc actccagcct gggtgacaaa gcaagaccct gtctcaaaaa aaaaaaaaag
7981  cctaactctt gacctccaag cctctatctg cccaaggcgc tggaggcagg gggacctggg
8041  acgactgggg ctgtgtgcag gatggggggcc tggaggcttg ttcaggcggg gccagttgct
8101  tgtgctgaag gggagaagga ggttactatt aggcaggaat ttcttctgag ctgcagtcac
8161  tcagcagaaa cagaggaaat gcttgctgga ctttgggata agacaaaat gactggaatg
8221  tggggctgag tatgtgagca accagggctg accctttatc cccacctctc tcacctccac
8281  agggccatgc tcccctgcgc ttgtctgtct tgagtccagc caagggtttg tttaattaac
8341  ccaagcccac taccactaat tttaattttg ggagaccagt ggggtactca ttatgcagat
8401  ctgtgttttt cttttttttt tgttttttgt ttttgttttt ttgagacgga gtctctctct
8461  gtcgcccagg ctggagtgca atggcgtgat cttggctcac tgcaacctcc actttcctgg
8521  gttcaagcaa ttctctggct tcagcttcct gagtagctgg gactacaggt gtatgtcacc
8581  acgcctggct aatttttttg tattttaaat agagatgagg tttcaccata ttggccaggc
8641  tggtctcgaa ctcctgacct caagtaatct gcctgccttg gcctcccaaa gtgctgggat
8701  tacagatgtg agccaccacg cccagccatc tgtgttgttt ttgtcgttgt tgttgttgtt
8761  gttattgttg ttttgagaca gagtctcact ctgtcaccca ggctggagtg cagtgacaca
8821  atctcagctc actgcaagct ccgcctcctg ggctcaagca atcctcccac ctcagcctcc
8881  tgagtagctg ggactacacg tgtgtgccat catgcccagc taatttttgt attttttggtg
8941  gaggcggggt ttcatcatgt cactcaggct ggtctcgaac ttctggactc aagcaatctg
9001  cctacctcgg cctcccaaag tattgggatt acaggcacga gccaccatgc ccggccagat
9061  ctgcgtgttt taaaatgcca cttgcaagct gggcatcatg gctcatgcct gtgtatgtgt
9121  gtgtgtgtgt gtgtgtgcat atatatatat gcatatatat atacatatat atatgcatat
9181  atatatgcat atatatatgc atatatatat gcatatatat atgtatatat atatgcatat
9241  atatgtatat atatatgcat atatatatgc atatatatgt ataiaggcac ttgcagagaa
9301  agagcagagg ttcgatcttt aatatgggaa atcgaggcaa gaggagttag gaggctctgg
9361  gatcactcca aatcacaccc attctatgag tccatgggat aatgccagca ttacctacac
9421  aggactttcc cttggagctg cattctctag tccaaaaaca ggcttagggc ttgggcccgg
9481  agctcaggcc tgggatccag gggctgagat gatgggggctg gtgggtgcta tcagggggag
9541  gatgagttaa ccagggacct attcctcttg cagtttctcg tgaactgtaa cagcattcag
9601  aatctgccca gcttgacctt catcatcaat ggtgtggagt tccctctgcc accttcctcc
9661  tatatcctca gtgtaagtcc tggtccctgc aggctgagcc accatgattg gggttgggag
9721  gaagggctgg ggagccagaa atgctgggtc tcctgccttg tgccattttc cgactccacg
9781  cttgtactca tttatcttcc ccactcattg attctaaacc cccttctctg gaacaaggct
9841  atgaaataga agattgtcat ctatgatcaa ttattattaa ttagtgggga gaggcactgg
9901  gctctttgtt gagcacttac tagggcagac cactgtgcaa agcactttgc ttcatgatcc
9961  catttaattg tcacagtatt taatgaggga gatactcatt tctgttttac aaatgaaaac
10021 ttggaggttc agagaggttg agtaactgac tcaaggcgac acagctaagg tttgaattca
10081 agttggtttg gctccaaggt ttaaccacca ggctgatctg ctccaaattg ggagcaggag
10141 ggaggtctgt gggaagagaa gtttcccatc atggggagag gagaccctgc tgaggaccac
10201 ggcagcctga atgtacctgt tccagaaatc ctcccacccg ctctgctctg gtggctcagt
10261 tggcctatga gccctcaagg cagagaccct ggctccctca gctctgcact tgtgctccca
10321 gcccagggct cagagctgag cagggcccag ctcatgtgtg gacaaatgaa tgagtgctgc
10381 cttttctttgt tgagcagaac aacggctact gcaccgtggg agtcgagccc acctacctgt
10441 cctcccagaa cggccagccc ctgtggatcc tcggggatgt cttcctcagg tcctactatt
10501 ccgtctacga cttgggcaac aacagagtag gctttgccac tgccgcctag acttgctgcc
10561 tcgacacgtg ggctccctc ttcctcttga ccctgcaccc tcctagggca ttgtatctgt
10621 ctttccactc tggattcagc cttctttttc tggactctgg actttctcta ataataaata
10681 gttcttcttt a
```

Human or non-human variants of the enzymes above are contemplated by the methods, systems, and devices disclosed herein. Variants of these enzymes include sequences that are at least 70% homologous to the human sequences above. As used herein, the term "variants" is intended to mean substantially similar sequences. For nucleic acid molecules, a variant comprises a nucleic acid molecule having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" nucleic acid molecule or polypeptide comprises a naturally occurring nucleotide sequence or amino acid sequence, respectively. For nucleic acid molecules, conservative variants include those sequences that, because of the degeneracy of the genetic code, encode the amino acid sequence of one of the polypeptides of the disclosure. Variant nucleic acid molecules also include synthetically derived nucleic acid molecules, such as those generated, for example, by using site-directed mutagenesis but which still encode a protein of the disclosure. Generally, variants of a particular nucleic acid molecule of the disclosure will have at least about 70%, 75%, 80%, 85%, 87%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular nucleic acid molecule of the disclosure (i.e., the reference DNA sequence) can also be evaluated by comparison of the percent sequence identity between the polypeptide encoded by a variant nucleic acid molecule and the polypeptide encoded by the reference nucleic acid molecule. Percent sequence identity between any two polypeptides can be calculated using sequence alignment programs and parameters described elsewhere herein. Where any given pair of nucleic acid molecule of the disclosure is evaluated by comparison of the percent sequence identity shared by the two polypeptides that they encode, the percent sequence identity between the two encoded polypeptides is at least about 70%, 75%, 80%, 85%, 87%, 90%, 91%, 92%, 93%, 94%, 95%, 96%, 97%, 98%, 99% or more sequence identity. In some embodiments, the term "variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present disclosure are biologically active, that is they continue to possess the desired biological activity of the native protein as described herein. Such variants may result from, for example, genetic polymorphism or from human manipulation. Biologically active variants of a protein of the disclosure will have at least about 70%, 75%, 80%, 85%, 87%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the disclosure may differ from that protein by as few as 1-15 amino acid residues, as few as 1-10, such as 6-10, as few as 20, 15, 10, 9, 8, 7, 6, 5, as few as 4, 3, 2, or even 1 amino acid residue. The proteins or polypeptides of the disclosure may be altered in various ways including amino acid substitutions, deletions, truncations, and insertions. Methods for such manipulations are generally known in the art. For example, amino acid sequence variants and fragments of the proteins can be prepared by mutations in the nucleic acid sequence that encode the amino acid sequence recombinantly.

In some embodiments, samples comprising cyst fluid may be screened using in vitro diagnostic methods to determine whether the samples comprise one or a plurality of mucinous cyst biomarkers. In some embodiments, samples from a subject may be screened using in vitro diagnostic methods to determine whether the samples comprise one or a plurality of mucinous cyst biomarkers that are cathepsin E, gastricsin, fragments thereof, or combinations thereof. In some embodiments, patients who are suspected of having a mucinous cyst may be screened using in vitro diagnostic methods to determine whether they have a mucinous cyst or potential to acquire a pancreatic cyst. In performing such methods, the methods comprise displaying high levels of the aspartyl protease or proteases as compared to levels of the same aspartyl protease or proteases measured from a control sample, such as a sample in which it is known that the sample does not comprise aspartyl protease or proteases or a sample that is known to be from a subject without a pre-malignant or malignant pancreatic growth.

In some embodiments, the disclosure relates to a method of detecting the presence, absence or quantity of aspartyl protease in a sample where the amount of enzyme in a sample is determined by calculating the amount of fluorescence of a cleaved substrate in a reaction vessel and is calculated by the expression: $(F_{final}-F_{initial})/F_{initial}$, wherein F stands for relative fluorescence units (RFU) and is a standard plate reader unit, where the amount of fluorescent signal detected is linearly or substantially linearly related to the amount of enzyme in a sample. For both gastricsin and cathepsin E, a threshold amount of for the amount in a sample which may indicate a mucinous versus non-mucinous cysts is about a 1.19, 1.20, 1.21, 1.22, 1.23, 1.24, 1.25, 1.26, 1.27, 1.28, 1.29 fold-change in fluorescence. In some embodiments, the sensitivity of the assay is about any of the sensitivities disclosed in the Examples or Figures section of the disclosure. In some embodiments, the sensitivity can be equal to detection of enzyme at a level of about 0.125 nM within the sample. In some embodiments, the sensitivity can be equal to detection of enzyme at a level of about 0.120 nM within the sample. In some embodiments, the sensitivity can be equal to detection of enzyme at a level of about 0.110 nM within the sample. In some embodiments, the sensitivity can be equal to detection of enzyme at a level of about 0.140 nM within the sample. In some embodiments, the sensitivity can be equal to detection of enzyme at a level of about 0.130 nM within the sample. In some embodiments, the sensitivity can be equal to detection of enzyme at a level of about 0.150 nM within the sample. In some embodiments, the sensitivity can be equal to detection of enzyme at a level of about 0.225 nM within the sample. In some embodiments, the sensitivity can be equal to detection of enzyme at a level of about 0.175 nM within the sample. In some embodiments, the sensitivity can be equal to detection of enzyme at a level of about 0.125 µM within the sample. In some embodiments, the sensitivity can be equal to detection of enzyme at a level of about 0.200 µM within the sample. In some embodiments, the sensitivity of the assay is about any of the sensitivities disclosed in the Examples or Figures section of the disclosure. In some embodiments, the sensitivity can be equal to detection of enzyme at a level of about 0.125 µM within the sample. In some embodiments, the sensitivity can be equal to detection of enzyme at a level of about 0.120 µM within the sample. In some embodiments, the sensitivity can be equal to detection of enzyme at a level of about 0.110 µM within the sample. In some embodiments, the sensitivity can be equal to detection of enzyme at a level of about 0.140 µM within the sample. In some embodiments, the sensitivity can be equal to detection of enzyme at a level of about 0.130 µM within the sample. In some embodiments, the sensitivity can be equal to detection of enzyme at a level of about 0.150 µM within the sample. In some embodiments, the sensitivity can be equal to detection of enzyme at a level of about 0.225 µM within the sample. In some embodiments, the sensitivity can be equal to detection of enzyme at a level of about 0.175 µM within the sample. In some embodiments, the sensitivity can be equal to detection of enzyme at a level of about 0.125 µM within the sample. In some embodiments, the sensitivity can be equal to detection of enzyme at a level of about 0.200 µM within the sample. In some embodiments, the sensitivity can be equal to detection of enzyme at a level of about 0.090, 0.091, 0.92, 0.093, 0.094, 0.095 µM within the sample. In some embodiments, the sensitivity can be equal to detection of enzyme at a level of from about 10, 11, 12, 13, 14, or 15 nM to about 100 nM within the sample.

In some embodiments, the disclosure relates to a method of detecting the presence, absence or quantity of aspartyl protease wherein the amount of aspartyl protease in a sample is determined by calculating the amount of intensity or presence of color caused by a colorimetric substance that forms in proportion to the amount of cleaved substrate and/or aspartyl protease in a reaction vessel. Colorimetric assays may be used in vitro when a probe comprises a substrate specific for the aspartyl protease is bound, noncovalently of covalently, to a colorimetric substrate. Example 8 provides an example.

In some embodiments, any tissue or body fluid sample may be used to detect the absence or presence of a mucinous cyst. Cystic fluid, saliva, cheek swabs (buccal swabs), hair bulb, blood serum and whole blood samples are among the common forms of samples used to obtain such samples. Examples of other samples can include semen, vaginal fluid, urine, lymph fluid, cerebral spinal fluid, amniotic fluid, skin and surgically excised tissue. Preferably, the sample is cystic fluid. One skilled in the art would readily recognize other types of samples of methods of obtaining them. In some embodiments of the methods disclosed herein, any of the methods disclosed herein comprise a step of obtaining a sample from a subject such as a human patient.

Any probe disclosed herein may be an antibody. The term "antibody" as used herein refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. As used herein, a "targeted binding agent" is an antibody, or binding fragment thereof, that preferentially binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. "Epitope" refers to that portion of an antigen or other macromolecule capable of forming a binding interaction that interacts with the variable region binding pocket of an antibody. "Binding fragments" of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay). An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and di-sulphide stabilized variable region (dsFv). As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known See, for example, Bowie et al. *Science* 253:164 (1991), which is incorporated by reference in its entirety.

In some instances, it may be desired to modify the detection probes so that they are more readily able to bind to the analyte. In such instances, the detection probes may be modified with certain specific binding members that are adhered thereto to form conjugated probes. For instance, the detection probe may be conjugated with antibodies as are further described below that are specific to aspartyl proteases. The detection probe antibody may be a monoclonal or polyclonal antibody or a mixture(s) fragment(s) thereof.

The antibodies may generally be attached to the detection probes using any of a variety of well-known techniques. For instance, covalent attachment of the antibodies to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may, be accomplished. A surface functional group may also be incorporated as a functionalized co-monomer as the surface of the detection probe may contain a relatively high surface concentration of polar groups. In addition, although detection probes are often functionalized after synthesis, such as with poly(thiophenol), the detection probes may be capable of direct covalent linking with an antibody without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting detection probes may then be contacted with ethanolamine, for instance, to block any, remaining activated sites. Overall, this process forms a conjugated detection probe, where the antibody is covalently attached to the probe. Besides covalent bonding, other attachment techniques, such as physical adsorption, may also be utilized in the present invention.

In one embodiment, the antibody may be detectably labeled by linking to an enzyme. The enzyme, in turn, when later exposed to a substrate or reaction product or enzyme disclosed herein, will react with a substrate or reaction product or enzyme disclosed herein in such a manner as to produce a chemical moiety which may be detected as, for example, by spectrophotometric or fluorometric means. Examples of enzymes which may be used to detectably label the antibodies as herein described include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

In some embodiments, in vivo or in vitro methods are performed to detect the presence, absence or quantity of one or a plurality of biomarkers corresponding to the likelihood of acquiring or having a pancreatic or mucinous cyst. In some embodiments, any of the disclosed methods or series of methods comprise exposing a sample or tissue in situ with one or a plurality of antibodies, optionally tagged with a visual detection agent such as a probe or fluorophore, which has binding affinity for one or a plurality of the biomarkers disclosed herein. Antibodies suitable for practicing the methods of the invention may be monoclonal and multivalent, and may be human, humanized or chimeric antibodies, comprising single chain antibodies, Fab fragments, F(ab') fragments, fragments produced by a Fab expression library, and/or binding fragments of any of the above. In certain embodiments of the invention, the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, CH3 and CL domains. Also included in the invention are antigen-binding fragments comprising any combination of variable region(s) with a hinge region, CH1, CH2, CH3 and CL domains. Preferably, the antibodies are human, murine (e.g., mouse and rat), donkey, sheep, rabbit, goal, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulins.

The antibodies suitable for practicing the methods of the present invention may be bispecific, trispecific or of greater multispecificity. Further, the antibodies of the present invention may have low risk of toxicity against granulocyte (neutrophil), NK cells, and CD4+ cells as bystander cells.

In accordance with one embodiment of the present invention, isolated and/or purified antibodies that recognized and bind an aspartyl protease may be generated for inclusion in a diagnostic device as disclosed herein. For instance, according to one embodiment, substantially pure recombinant polypeptide suitable for use as an immunogen may be isolated from cells in which it is produced and then polyclonal antiserum containing antibodies to heterogeneous epitopes of an aspartyl protease may be prepared by immunizing suitable hosts with the expressed polypeptide, which may be unmodified or modified to enhance immunogenicity. As is generally known in the art, effective polyclonal antibody production may be affected by many factors related both to the antigen and the host species. For example, small molecules tend to be less immunogenic than others and may require the use of carriers and adjuvant. Also, hosts may vary in response to site of inoculations and dose, with both inadequate and excessive doses of antigen resulting in low titer antisera.

Booster injections may be given at regular intervals, and antiserum harvested when antibody titer thereof, as determined semi-quantitatively, for example, by double immunodiffusion in agar against known concentrations of the antigen, begins to fall. See, for example, Ouchterlony et al. (Handbook of Experimental Immunology, Wier, D. (ed.) chapter 19. Blackwell (1973)). In general, plateau concentration of antibody may usually be in the range of 0.1 to 0.2 mg/ml of serum. Affinity of the antisera for the antigen is determined by preparing competitive binding curves, as described, for example, by Fisher (Manual of Clinical Immunology, Ch. 42. (1980)).

Another possible approach to raising antibodies against the aspartyl protease or substrates thereof may utilize synthetic peptides synthesized on a commercially available peptide synthesizer based upon the amino acid sequence correlating to the known aspartyl protease.

Antibodies may optionally be raised against the aspartyl protease or fragments thereof by subcutaneous injection of a DNA vector that expresses the polypeptide into laboratory animals, such as mice. Delivery of the recombinant vector into the animals may be achieved according to methods as are generally known in the art.

In another embodiment, monoclonal antibodies may be raised by hybridoma cells, phage display libraries, or other methodology. Monoclonal antibodies may be e.g., human, rat, or mouse derived. For the production of human monoclonal antibodies, hybridoma cells may be prepared by fusing spleen cells from an immunized host, e.g., a mouse, with a tumour cell. Appropriately secreting hybridoma cells may thereafter be selected according to, for example, the method of Kohler and Milstein (Nature 256:495 (1975)), or derivative methods thereof. (Procedures for monoclonal antibody production are also described in Harlow and Lane (1988). Antibodies, A Laboratory Manual, Cold Spring Harbor Laboratory, New York; Cole, et al., "Monoclonal antibodies and Cancer Therapy, Alan R. Liss, Inc., pp. 77-96.). Rodent antibodies may be humanized using recombinant DNA technology according to techniques known in the art. Alternatively, chimeric antibodies, single chain antibodies, Fab fragments, and so forth may also be developed against the aspartyl protease using skills known in the art.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, EMBO J., 10:3655-3659 (1991).

According to another approach described in WO96/27011, the interface between a pair of antibody molecules can be engineered to maximize the percentage of heterodimers which are recovered from recombinant cell culture. Such interfaces may comprise at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. An alternative method links two different single chain variable regions to heat stable antigen (HSA). Using HSA as linker increases serum half-life, and has the benefit of low immunogenicity.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kos-telny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments (VH-CH1-VH-CH1) which form a pair of antigen binding regions. Linear antibodies can be bispecific or monospecific.

Within the context of the present disclosure, antibodies are understood to include monoclonal antibodies and polyclonal antibodies, antibody fragments (e.g., Fab and F(ab') 2), chimeric antibodies bifunctional or bispecific antibodies and tetrameric antibody complexes. Antibodies are understood to be reactive against a selected antigen on the surface of a T cell if they bind with an appropriate affinity (association constant), e.g. greater than or equal to $10^{-7}$M. Additionally, antibodies that may be used in the methods of the present invention may also be described or specified in terms of their binding affinities include those with a dissociation constant or Kd less than about $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-9}$ M, $5\times10^{-11}$ M, $10^{-11}$ M, $5\times10^{-12}$ M, $10^{-12}$ M, $5\times10^{-13}$M, $10^{-13}$ M, $5\times10^{-14}$ M, $10^{-14}$ M, $5\times10^{-15}$ M, $10^{-15}$ M. In some embodiments, the antibodies may have any one of the above disassociation constants in relation to its affinity for biomarkers disclosed herein. In some embodiments, the antibody may be covalently bound to gastricsin, cathepsin E, analogs thereof, or functional fragments thereof. In some embodiments, the antibodies may have any one of the above disassociation constants in relation to its affinity for gastricsin, cathepsin E, analogs thereof, or functional fragments thereof. In some embodiments, the antibody may be covalently bound to any one or plurality of gastricsin, cathepsin E, cathepsin D, analogs thereof, substrates thereof, or functional fragments thereof.

Antibodies can be fragmented using conventional techniques and the fragments screened for utility in the same manner as described above for the whole antibodies. For example, F(ab')2 fragments can be generated by treating antibody with pepsin. The resulting F(ab')2 fragment can be treated to reduce disulfide bridges to produce Fab' fragments.

The invention also contemplates using one or a plurality of chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the selected antigens on the surface of differentiated cells or tumor cells. See, for example, Morrison et al., 1985; Proc. Natl. Acad. Sci. U.S.A. 81, 6851; Takeda et al., 1985, Nature 314:452;

Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B. In any of the disclosed methods, the methods may comprise exposing any antibody that have an affinity for any of the reaction products created by cleavage of a known substrate after exposure of the substrate to any one or plurality of aspartyl proteases.

Chemical conjugation is based on the use of homo- and heterobifunctional reagents with E-amino groups or hinge region thiol groups. Homobifunctional reagents such as 5,5'-Dithiobis(2-nitrobenzoic acid) (DNTB) generate disulfide bonds between the two Fabs, and O-phenylenedimaleimide (O-PDM) generate thioether bonds between the two Fabs (Brenner et al., 1985, Glennie et al., 1987). Heterobifunctional reagents such as N-succinimidyl-3-(2-pyridylditio)propionate (SPDP) combine exposed amino groups of antibodies and Fab fragments, regardless of class or isotype (Van Dijk et al., 1989).

Various formats may be used to test for the presence or absence of an aspartyl protease or functional fragment thereof using the assay devices of the present disclosure. For instance, a "sandwich" format typically involves mixing the test sample with probes conjugated with a specific binding member (e.g., antibody) for the analyte to form complexes between the analyte and the conjugated probes. These complexes are then allowed to contact a receptive material (e.g., antibodies) immobilized within the detection zone. Binding occurs between the analyte/probe conjugate complexes and the immobilized receptive material, thereby localizing "sandwich" complexes that are detectable to indicate the presence of the analyte. This technique may be used to obtain quantitative or semi-quantitative results. Some examples of such sandwich-type assays are described by U.S. Pat. No. 4,168,146 to Grubb, et al. and U.S. Pat. No. 4,366,241 to Tom, et al., which are incorporated herein in their entirety by reference thereto for all purposes. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601 to Deutsch, et al., U.S. Pat. No. 4,442,204 to Liotta, and U.S. Pat. No. 5,208,535 to Buechler, et al., which are incorporated herein in their entirety by reference thereto for all purposes. Various other device configurations and/or assay formats are also described in U.S. Pat. No. 5,395,754 to Lambotte, et al.; U.S. Pat. No. 5,670,381 to Jou, et al.; and U.S. Pat. No. 6,194,220 to Malick, et al., which are incorporated herein in their entirety by reference thereto for all purposes.

Although various assay device configuration have been described herein, it should be understood that any known assay device may be utilized that is capable of incorporating an antibody in accordance with the present invention. For example, electrochemical affinity assay devices may also be utilized, which detect an electrochemical reaction between an aspartyl protease (or complex thereof) and a capture ligand on an electrode strip. For example, various electrochemical assays and assay devices are described in U.S. Pat. No. 5,508,171 to Walling, et al.; U.S. Pat. No. 5,534,132 to Vreeke, et al.; U.S. Pat. No. 6,241,863 to Monbouquette; U.S. Pat. No. 6,270,637 to Crismore, et al.; U.S. Pat. No. 6,281,006 to Heller, et al.; and U.S. Pat. No. 6,461,496 to Feldman, et al., which are incorporated herein in their entirety by reference thereto for all purposes.

One skilled in the art will readily appreciate the wide range of methods and techniques used for detecting the presence and/or quantity of proteins, enzymes and/or cleavage products in a complex sample. Techniques for detecting proteins or cleavage products include, but are not limited to, microscopy, immunostaining, immunoprecipitation, immunoelectrophoresis, Western blot, BCA assays, spectrophotometry, enzymatic assays, microchip assays, and mass spectrometry. In some embodiments, purification of proteins are necessary before detection of quantification techniques are employed. Techniques for purifying proteins include, but are not limited to, chromatography methods, including ion exchange, size-exclusion, and affinity chromatography, gel electrophoresis, magnetic beads comprising any antibody, antibody-like protein or antibody fragment or variant, Bradford protein assays. In some embodiments, methods of measuring the presence, absence, or quantity of aspartyl protease or functional fragments thereof comprise antibodies or antibody fragments specific to aspartyl protease or functional fragments thereof.

As used herein, the term "score" refers to a single value that can be used as a component in a predictive model for the diagnosis, prognosis, and/or clinical treatment plan for a subject, wherein the single value is calculated by combining and/or normalizing raw data values with or against a control value based upon features or metrics measured in the system. In some embodiments, the score is calculated by through an interpretation function or algorithm. In some embodiments, the subject is suspected of having, is at risk of developing, or has a pancreatic cyst. In some embodiments, the score is calculated through an interpretation function or algorithm that normalizes the amount of an experimental value obtained through a test disclosed herein as compared to a control value obtained through a test disclosed herein or by a predetermined value conducted prior to conducting a test disclosed herein but corresponding to a control or normal (e.g. uninfected) value.

To facilitate the detection of a protease disclosed herein, such as an aspartyl protease, within a sample, a detectable substance may be pre-applied to a surface, for example a plate, well, bead, nanodroplet, or other solid support comprising one or a plurality of reaction vessels. In some embodiments, a sample may be pre-mixed with a diluent or reagent before it is applied to a surface. The detectable substance may function as a detection probe that is detectable either visually or by an instrumental device. Any substance generally capable of producing a signal that is detectable visually or by an instrumental device may be used as detection probes. Suitable detectable substances may include, for instance, luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and so forth. Other suitable detectable substances may be described in U.S. Pat. No. 5,670,381 to Jou, et al. and U.S. Pat. No. 5,252,459 to Tarcha, et al., which are incorporated herein in their entirety by reference thereto for all purposes. If the detectable substance is colored, the ideal electromagnetic radiation is light of a complementary wavelength. For instance, blue detection probes strongly absorb red light.

In some embodiments, the detectable substance may be a luminescent compound that produces an optically detectable signal that corresponds to the level or quantity of protease in the sample. For example, suitable fluorescent molecules may include, but are not limited to, fluorescein, europium chelates, phycobiliprotein, phycoerythrin, phycocyanin, allophycocyanin, o-phthaldehyde, fluorescamine, rhodamine, and their derivatives and analogs. Other suitable fluorescent compounds are semiconductor nanocrystals commonly referred to as "quantum dots." For example, such nanocrystals may contain a core of the formula CdX, wherein X is Se, Te, S, and so forth. The nanocrystals may also be passivated with an overlying shell of the formula YZ, wherein Y is Cd or Zn, and Z is S or Se. Other examples of suitable semiconductor nanocrystals may also be described in U.S. Pat. No. 6,261,779 to Barbera-Guillem, et al. and U.S. Pat. No. 6,585,939 to Dapprich, which are incorporated herein in their entirety by reference thereto for all purposes.

Further, suitable phosphorescent compounds may include metal complexes of one or more metals, such as ruthenium, osmium, rhenium, iridium, rhodium, platinum, indium, palladium, molybdenum, technetium, copper, iron, chromium, tungsten, zinc, and so forth. Especially preferred are ruthenium, rhenium, osmium, platinum, and palladium. The metal complex may contain one or more ligands that facilitate the solubility of the complex in an aqueous or non-aqueous environment. For example, some suitable examples of ligands include, but are not limited to, pyridine; pyrazine; isonicotinamide; imidazole; bipyridine; terpyridine; phenanthroline; dipyridophenazine; porphyrin; porphine; and derivatives thereof. Such ligands may be, for instance, substituted with alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxy-succinimide.

Porphyrins and porphine metal complexes possess pyrrole groups coupled together with methylene bridges to form cyclic structures with metal chelating inner cavities. Many of these molecules exhibit strong phosphorescence properties at room temperature in suitable solvents (e.g., water) and an oxygen-free environment. Some suitable porphyrin complexes that are capable of exhibiting phosphorescent properties include, but are not limited to, platinum (II) coproporphyrin-I and III, palladium (II) coproporphyrin, ruthenium coproporphyrin, zinc(II)-coproporphyrin-I, derivatives thereof, and so forth. Similarly, some suitable porphine complexes that are capable of exhibiting phosphorescent properties include, but not limited to, platinum(II) tetra-meso-fluorophenylporphine and palladium(II) tetra-meso-fluorophenylporphine. Still other suitable porphyrin and/or porphine complexes are described in U.S. Pat. No. 4,614,723 to Schmidt, et al.; U.S. Pat. No. 5,464,741 to Hendrix; U.S. Pat. No. 5,518,883 to Soini; U.S. Pat. No. 5,922,537 to Ewart. et al.; U.S. Pat. No. 6,004,530 to Sagner, et al.; and U.S. Pat. No. 6,582,930 to Ponomarev, et al., which are incorporated herein in their entirety by reference thereto for all purposes.

Bipyridine metal complexes may also be utilized as phosphorescent compounds. Some examples of suitable bipyridine complexes include, but are not limited to, bis [(4,4'-carbomethoxy)-2,2'-bipyridine]2-[3-(4-methyl-2,2'-bipyridine-4-yl)propyl]-1,3-dioxolane ruthenium (II); bis(2,2'-bipyridine)[4-(butan-1-al)-4'-methyl-2,2'-bipyridine]ruthenium (II); bis(2,2'-bipyridine)[4-(4'-methyl-2,2'-bipyridine-4'-yl)-butyric acid]ruthenium (II); tris(2,2'-bipyridine)ruthenium (II); (2,2'-bipyridine) [bis-bis(1,2-diphenylphosphino)ethylene]2-[3-(4-methyl-2,2'-bipyridine-4'--yl)propyl]-1,3-dioxolane osmium (II); bis(2,2'-bipyridine) [4-(4'-methyl-2,2'-bipyridine)-butylamine] ruthenium (II); bis(2,2'-bipyridine) [1-bromo-4(4'-methyl-2,2'-bipyridine-4-yl)butan-e]ruthenium (II); bis(2,2'-bipyridine)maleimidohexanoic acid, 4-methyl-2,2'-bipyridine-4'-butylamide ruthenium (II), and so forth. Still other suitable metal complexes that may exhibit phosphorescent properties may be described in U.S. Pat. No. 6,613,583 to Richter, et al.; U.S. Pat. No. 6,468,741 to Massey, et al.; U.S. Pat. No. 6,444,423 to Meade, et al.; U.S. Pat. No. 6,362,011 to Massey, et al.; U.S. Pat. No. 5,731,147 to Bard, et al.; and U.S. Pat. No. 5,591,581 to Massey, et al., which are incorporated herein by reference in their entireties.

In some cases, luminescent compounds may have a relatively long emission lifetime and/or may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of a luminescent compound to remain far apart from its emission wavelengths and is desirable because a large difference between excitation and emission wavelengths makes it easier to eliminate the reflected excitation radiation from the emitted signal. Further, a large Stokes shift also minimizes interference from luminescent molecules in the sample and/or light scattering due to proteins or colloids, which are present with some body fluids (e.g., blood). In addition, a large Stokes shift also minimizes the requirement for expensive, high-precision filters to eliminate background interference. For example, in some embodiments, the luminescent compounds have a Stokes shift of greater than about 50 nanometers, in some embodiments greater than about 100 nanometers, and in some embodiments, from about 100 to about 350 nanometers.

For example, exemplary fluorescent compounds having a large Stokes shift include lanthanide chelates of samarium (Sm (III)), dysprosium (Dy (III)), europium (Eu (III)), and terbium (Tb (I)). Such chelates may exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy may be transferred from the excited chromophore to the lanthanide. This is followed by a fluorescence emission characteristic of the lanthanide. Europium chelates, for instance, have Stokes shifts of about 250 to about 350 nanometers, as compared to only about 28 nanometers for fluorescein. Also, the fluorescence of europium chelates is long-lived, with lifetimes of about 100 to about 1000 microseconds, as compared to about 1 to about 100 nanoseconds for other fluorescent labels. In addition, these chelates have narrow emission spectra, typically having bandwidths less than about 10 nanometers at about 50% emission. One suitable europium chelate is N-(p-isothiocyanatobenzyl)-diethylene triamine tetraacetic acid-Eu.sup.+3.

In addition, lanthanide chelates that are inert, stable, and intrinsically fluorescent in aqueous solutions or suspensions may also be used in the present invention to negate the need for micelle-forming reagents, which are often used to protect chelates having limited solubility and quenching problems in aqueous solutions or suspensions. One example of such a chelate is 4-[2-(4-isothiocyanatophenyl)ethynyl]-2,6-bis([N,N-bis(carboxymethyl)amino] methyl)-pyridine [Ref: Lovgren, T., et al.; Clin. Chem. 42, 1196-1201 (1996)]. Several lanthanide chelates also show exceptionally high signal-to-noise ratios. For example, one such chelate is a tetradentate .beta.-diketonate-europium chelate [Ref: Yuan, J. and Matsumoto, K.; Anal. Chem. 70, 596-601 (1998)]. In addition to the fluorescent labels described above, other labels that are suitable for use in the present invention may be described in U.S. Pat. No. 6,030,840 to Mullinax, et al.; U.S. Pat. No. 5,585,279 to Davidson; U.S. Pat. No. 5,573,909 to Singer, et al.; U.S. Pat. No. 6,242,268 to Wieder, et al.; and U.S. Pat. No. 5,637,509 to Hemmila, et al., which are incorporated herein by reference in their entirety. Any substrate or enzyme disclosed here may have one or more chemiluminescent probes adsorbed, conjugated or attached to its structure (either on an amino acid side chain or in sequence with the alpha, beta, and/or gamma carbon atoms of the amino acid backbone.

Detectable substances (such as those capable of associating with or reacting to the presence of the reaction products cleaved by the proteases described herein), such as described above, may be used alone or in conjunction with a particle (sometimes referred to as "beads" or "microbeads"). For instance, naturally occurring particles, such as nuclei, mycoplasma, plasmids, plastids, mammalian cells (e.g., erythrocyte ghosts), unicellular microorganisms (e.g., bacteria), polysaccharides (e.g., agarose), etc., may be used. Further, synthetic particles may also be utilized. For example, in one embodiment, latex microparticles that are labeled with a fluorescent or colored dye are utilized. Although any synthetic particle may be used in the present invention, the particles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and so forth, or an aldehyde, carboxyl, amino, hydroxyl, or hydrazide derivative thereof. Other suitable particles may be described in U.S. Pat. No. 5,670,381 to Jou, et al.; U.S. Pat. No. 5,252,459 to Tarcha, et al.; and U.S. Patent Publication No. 2003/0139886 to Bodzin, et al., which are incorporated herein in their entirety by reference thereto for all purposes. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc. Metallic particles (e.g., gold particles) may also be utilized in the present invention.

When utilized, the shape of the particles may generally vary. In one particular embodiment, for instance, the particles are spherical in shape. However, it should be understood that other shapes are also contemplated by the present invention, such as plates, rods, discs, bars, tubes, irregular shapes, etc. In addition, the size of the particles may also vary. For instance, the average size (e.g., diameter) of the particles may range from about 0.1 nanometers to about 100 microns, in some embodiments, from about 1 nanometer to about 10 microns, and in some embodiments, from about 10 to about 100 nanometers.

In some instances, it may be desired to modify the detection probes so that they are more readily able to bind to the analyte. In such instances, the detection probes may be modified with certain specific binding members that are adhered thereto to form conjugated probes. For instance, the detection probe may be conjugated with antibodies as are further described below that are specific to aspartyl proteases. The detection probe antibody may be a monoclonal or polyclonal antibody or a mixture(s) or fragment(s) thereof.

Antibodies that are capable of binding any one or plurality of biomarkers or proteases disclosed herein may generally be attached to the detection probes using any of a variety of well-known techniques. For instance, covalent attachment of the antibodies to the detection probes (e.g., particles) may be accomplished using carboxylic, amino, aldehyde, bromoacetyl, iodoacetyl, thiol, epoxy and other reactive or linking functional groups, as well as residual free radicals and radical cations, through which a protein coupling reaction may be accomplished. A surface functional group may also be incorporated as a functionalized co-monomer as the surface of the detection probe may contain a relatively high surface concentration of polar groups. In addition, although detection probes are often functionalized after synthesis, such as with poly(thiophenol), the detection probes may be capable of direct covalent linking with an antibody without the need for further modification. For example, in one embodiment, the first step of conjugation is activation of carboxylic groups on the probe surface using carbodiimide. In the second step, the activated carboxylic acid groups are reacted with an amino group of an antibody to form an amide bond. The activation and/or antibody coupling may occur in a buffer, such as phosphate-buffered saline (PBS) (e.g., pH of 7.2) or 2-(N-morpholino) ethane sulfonic acid (MES) (e.g., pH of 5.3). The resulting detection probes may then be contacted with ethanolamine, for instance, to block any remaining activated sites. Overall, this process forms a conjugated detection probe, where the antibody is covalently attached to the probe. Besides covalent bonding, other attachment techniques, such as physical adsorption, may also be utilized in the present invention.

In one embodiment, the antibody may be detectably labeled by linking to an enzyme. The enzyme, in turn, when later exposed to a substrate, will react with the substrate in such a manner as to produce a chemical moiety which may be detected as, for example, by spectrophotometric or fluorometric means. Examples of enzymes which may be used to detectably label the antibodies as herein described include malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase.

Another technique that may also result in greater sensitivity when used in conjunction with the present invention consists of coupling the antibodies to low molecular weight haptens. The haptens may then be specifically detected by means of a second reaction. For example, it is common to use such haptens as biotin (reacting with avidin) or dinitrophenol, pyridoxal and fluorescamine (reacting with specific antihapten antibodies) in this manner.

The antibodies of the present invention also may be detectably labeled by coupling to a chemiluminescent compound or a fluorescent compound. The presence of the chemiluminescent-tagged antibody is then determined by detecting the presence of luminescence that arises during the course of the chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the antibodies as further described below. Bioluminescence is a type of chemiluminescence found in biological systems in which a catalytic protein increases the efficiency of the chemiluminescent reaction. The presence of a bioluminescent reagent is determined by detecting the presence of luminescence. Important bioluminescent compounds for purposes of labeling are luciferin, luciferase and aequorin.

In some embodiments, the system disclosed herein comprises a chip, slide or other silica surface comprising one or a plurality of addressable locations or reaction vessels within which one or a plurality of peptides, protease or peptidase substrates, and/or antibodies with an affinity for the biomarkers disclosed herein are immobilized or contained. Upon contacting a sample comprising any one of the peptides or functional fragments thereof to the one or a plurality of peptides, protease substrates, and/or antibodies with an affinity for the biomarkers disclosed herein, a reaction ensues whose reaction products are detectable by any means known in the art or disclosed herein. For instance, the reaction products may be detectable by fluorescence, optical imaging, field microscopy, mass spectrometry, or the like.

The disclosure provides for quantifying the amount or detecting the presence or absence of a mucinous cyst by exposure of a sample taken from a subject to quantum dots (QDs). There has been substantial interest in exploiting the properties of compound semiconductor particles with dimensions on the order of about 2 to about 50 nm, often referred to as QDs or nanocrystals. These materials are of commercial interest due to their size-tunable electronic properties that can be exploited in many commercial applications.

The most studied of semiconductor materials have been the chalcogenides II-VI materials namely ZnS, ZnSe, CdS, CdSe, CdTe; especially CdSe due to its tunability over the visible region of the spectrum. Reproducible methods for the large-scale production of these materials have been developed from "bottom up" techniques, whereby particles are prepared atom-by-atom, i.e., from molecules to clusters to particles, using "wet" chemical procedures.

Two fundamental factors, both related to the size of the individual semiconductor nanoparticles, are responsible for their unique properties. The first is the large surface-to-volume ratio. As particles become smaller, the ratio of the number of surface atoms to those in the interior increases. This leads to the surface properties playing an important role in the overall properties of the material. The second factor is a change in the electronic properties of the material when the material is very small in size. At extremely small sizes quantum confinement causes the material's band gap to gradually increase as the size of the particles decrease. This effect is a consequence of the confinement of an 'electron in a box' giving rise to discrete energy levels similar to those observed in atoms and molecule rather than a continuous band as observed in the corresponding bulk semiconductor material. Thus, the "electron and hole" produced by the absorption of electromagnetic radiation are closer together than they would be in the corresponding macrocrystalline material. This leads to a narrow bandwidth emission that depends upon the particle size and composition of the nanoparticle material. QDs therefore have higher kinetic energy than the corresponding macrocrystalline material and consequently the first excitonic transition (band gap) increases in energy with decreasing particle diameter.

QD nanoparticles of a single semiconductor material tend to have relatively low quantum efficiencies due to electron-hole recombination occurring at defects and dangling bonds situated on the nanoparticle surface, which may lead to non-radiative electron-hole recombinations. One method to eliminate such defects and dangling bonds on the inorganic surface of the QD is to grow a second inorganic material, having a wider band-gap and small lattice mismatch to that of the core material, epitaxially on the surface of the core particle, producing a "core-shell" particle. Core-shell particles separate any carriers confined in the core from surface states that would otherwise act as non-radiative recombination centers. One example is QDs having a ZnS shell grown on the surface of a CdSe core.

Rudimentary QD-based light-emitting devices have been made by embedding colloidally produced QDs in an optically clear LED encapsulation medium, typically a silicone or an acrylate, which is then placed on top of a solid-state LED. The use of QDs potentially has some significant advantages over the use of the more conventional phosphors, such as the ability to tune the emission wavelength, strong absorption properties, improved color rendering, and low scattering. Any of the methods herein may comprise one or more steps comprising normalizing values obtained from exposure of a sample to a substrate specific for one or a plurality of known enzymes disclosed herein (or functional fragments thereof) comprising one or a plurality of quantum dots.

For the commercial application of QDs in next-generation light-emitting devices, the QDs are preferably incorporated into the LED encapsulating material while remaining as fully mono-dispersed as possible and without significant loss of quantum efficiency. The methods developed to date are problematic, not least because of the nature of current LED encapsulants. QDs can agglomerate when formulated into current LED encapsulants, thereby reducing the optical performance of the QDs. Moreover, once the QDs are incorporated into the LED encapsulant, oxygen can migrate through the encapsulant to the surfaces of the QDs, which can lead to photo-oxidation and, as a result, a drop in quantum yield (QY).

One way of addressing the problem of oxygen migration to the QDs has been to incorporate the QDs into a medium with low oxygen permeability to form "beads" of such a material containing QDs dispersed within the bead. The QD-containing beads can then be dispersed within an LED encapsulant. Examples of such systems are described in U.S. patent application Ser. No. 12/888,982, filed Sep. 23, 2010 (Pub. No.: 2011/0068322) and Ser. No. 12/622,012, filed Nov. 19, 2009 (Pub. No.: 2010/0123155), the entire contents of which are incorporated herein by reference.

Compositions

The disclosure relates to substrates specific for binding, association to the enzymes disclosed herein. In some embodiments, the substrates are specific for aspartyl proteases, such as cathespin E and/or gastricsin. In some embodiments, the substrates are parts of kits and are labeled with one or more probes and, when exposed to a enzyme, the enzyme may react with the substrate creating one or more reaction products. In the case of cathepsin E and/or gastriscin, the reaction products are amino acid sequences that are cleavage products. Compositions comprising the substrates and/or the cleavage products are contemplated by the disclosure. In some embodiments, the composition comprise one or a plurality of amino acid sequences comprising an amino acid substrate specific for an aspartyl protease. In some embodiments, the composition comprises an amino acid sequence that is a substrate for the aspartyl protease or aspartyl proteases, such amino acid sequence comprises at least one amino acid sequence comprising the formula:

$$N_1-X_1-X_2-X_3-X_4-X_5-X_6-X_7-N_2$$ (SEQ ID NO: 49)

wherein:

$N_1$ is an amino terminus and/or one or a plurality of natural or modified amino acids, nucleic acids, or probes covalently or non-covalently attached to the terminus;

$X_1$ is a natural or modified amino acid residue chosen from: D, A, V, N, P, F, H, I E, M, W, K and G;

$X_2$ is a natural or modified amino acid residue chosen from: E, F, G, M, K, A, K, L and W;

$X_3$ is a natural or modified amino acid residue chosen from: G, F, K, D, M, T, I, Y, W, L and R;

$X_4$ is a natural or modified amino acid residue chosen from: Y, A, S, F, W, L, T and M;

$X_5$ is a natural or modified amino acid residue chosen from: Y, M, L, A, F, and S;

$X_6$ is a natural or modified amino acid residue chosen from: L, T, and R;

$X_7$ is a natural or modified amino acid residue chosen from: Q and Y; and $N_2$ is a carboxy terminus or one or a plurality of natural or modified amino acids, nucleic acids, or probes covalently or non-covalently attached to the terminus. In some embodiments, the composition further comprises an additional amino acid residue $X_8$ downstream of the $X_7$ residue, wherein $X_8$ is a natural or modified amino acid residue chosen from: H, M, L, K, G, and W.

In some embodiments, the composition comprises an amino acid sequence that is a substrate for the aspartyl protease or aspartyl proteases, such amino acid sequence comprises at least one amino acid sequence comprising the formula:

$$N_1-X_3-X_4-X_5-X_6-N_2$$ (SEQ ID NO: 50)

wherein:

$N_1$ is an amino terminus and/or one or a plurality of natural or modified amino acids, nucleic acids, or probes covalently or non-covalently attached to the terminus in any contiguous or non-contiguous order or pattern;

$X_3$ is a natural or modified amino acid residue independently selected from: A, H, N, Q, G, F, K, D, M, T, I, Y, W, L, norleucine and R;

$X_4$ is a natural or modified amino acid residue independently selected from: D, E, Y, A, S, F, W, H, L, T, norleucine and M;

$X_5$ is a natural or modified amino acid residue independently selected from: Y, D, E, I, norleucine, M, L, A, F, and S;

$X_6$ is a natural or modified amino acid residue chosen from: L, V, H, Q, N, I, norleucine, Y, A, G, E, T, and R; and $N_2$ is a carboxy terminus or one or a plurality of natural or modified amino acids, nucleic acids, or probes covalently or non-covalently attached to the terminus in any contiguous or non-contiguous order or pattern. In some embodiments, the composition further comprises an additional amino acid residue $X_8$ downstream of the $X_7$ residue, wherein $X_8$ is a natural or modified amino acid residue chosen from: H, M, L, K, G, and W.

In some embodiments, the composition comprises an amino acid sequence that is a substrate for the aspartyl protease or aspartyl proteases, such amino acid sequence comprises at least one amino acid sequence comprising the formula:

$$N_1-X_3-X_4-X_5-X_6-N_2$$ (SEQ ID NO: 50)

wherein:

$N_1$ is an amino terminus and/or one or a plurality of natural or modified amino acids, nucleic acids, or probes covalently or non-covalently attached to the terminus in any contiguous or non-contiguous order or pattern;

$X_3$ is a natural or modified amino acid residue independently selected from: A, H, N, Q, G, F, K, D, M, T, I, Y, W, L, norleucine and R;

$X_4$ is a natural or modified amino acid residue independently selected from: D, E, Y, A, S, F, W, H, L, T, norleucine and M;

$X_5$ is a natural or modified amino acid residue independently selected from: Y, D, E, I, norleucine, M, L, A, F, and S;

$X_6$ is a natural or modified amino acid residue chosen from: L, V, H, Q, N, I, norleucine, Y, A, G, E, T, and R; and $N_2$ is a carboxy terminus or one or a plurality of natural or modified amino acids, nucleic acids, or probes covalently or non-covalently attached to the terminus in any contiguous or non-contiguous order or pattern; and wherein $X_3$ and $X_4$ flank the amide bond upon which a cleavage reaction is performed by the enzyme.

In some embodiments, the composition comprises an amino acid sequence that is a substrate for the aspartyl protease or aspartyl proteases, such amino acid sequence comprises at least one amino acid sequence comprising the formula:

$$N_1-X_3-X_4-X_5-X_6-N_2$$ (SEQ ID NO: 51)

wherein:

$N_1$ is an amino terminus and/or one or a plurality of natural or modified amino acids, nucleic acids, or probes covalently or non-covalently attached to the terminus in any contiguous or non-contiguous order or pattern;

$X_3$ is a natural or modified amino acid residue independently selected from: any of the amino acid residues at a position immediately adjacent and contiguous to $X_4$ on its N terminal side in the amino acid orientation depicted in the Figures or Examples;

$X_4$ is a natural or modified amino acid residue independently selected from: any of the amino acid residues at a position immediately adjacent to a cleavage site on the N terminal side of the amino acid sequence depicted in the Figures or Examples;

$X_5$ is a natural or modified amino acid residue independently selected from: any of the amino acid residues at a position immediately adjacent to a cleavage site on the C terminal side of the amino acid sequence depicted in the Figures or Examples;

$X_6$ is a natural or modified amino acid residue chosen from: any of the amino acid residues at a position immediately adjacent and contiguous to $X_5$ on its carboxy terminal side in the amino acid orientation depicted in the Figures or Examples;

$N_2$ is a carboxy terminus or one or a plurality of natural or modified amino acids, nucleic acids, or probes covalently or non-covalently attached to the terminus in any contiguous or non-contiguous order or pattern; wherein $X_4$ and $X_5$ are the amino acid residues between which the enzyme or enzymes disclosed in the Figures cleaves the substrate (depicted by a vertical line in the Figures). In some embodiments, $X_4$ is independently selected from: Y, F, W, L, or norleucine, or a modified residue thereof.

$X_5$ is independently selected from: Y, norleucine, L, A, F, S, or a modified residue thereof.

The substrates of the disclosure may be of any length including from about 7 to about 20 amino acids residues in length, from about 5 to about 30 amino acids in the length, from about 5 to about 40 amino acids in the length, from about 5 to about 30 amino acids in the length, from about 5 to about 50 amino acids in the length, from about 5 to about 60 amino acids in the length, from about 5 to about 70 amino acids in the length, from about 5 to about 80 amino acids in the length, from about 5 to about 90 amino acids in the length, from about 5 to about 100 amino acids in the length, from about 7 to about 30 amino acids in the length, from about 7 to about 15 amino acids in the length, from about 7 to about 10 amino acids in the length, or any positive integer in between those values. In some embodiments, the substrate is no more than 25, 20, 19, 18, 17, 16, 15, 14, 13, 12, 11, 10, 9, 8, 7 or six amino acids in length, but may comprise any one or plurality of probes which are detectable after the enzymes disclosed herein catalyze the production of reaction products upon contact with substrates.

In some embodiments, the composition comprises an amino acid sequence that is a substrate for the aspartyl protease or aspartyl proteases, such amino acid sequence comprises at least one amino acid sequence comprising the formula:

$$N_1-X_1-X_2-X_3-X_4-X_5-X_6-X_7-N_2 \quad \text{(SEQ ID NO: 49)}$$

wherein:

$X_1$ is a natural or modified amino acid residue chosen from: D, A, V, N, P, F, H, I E, M, W, K and G;

$X_2$ is a natural or modified amino acid residue chosen from: E, F, G, M, K, A, K, L and W;

$X_3$ is a natural or modified amino acid residue chosen from: G, F, K, D, M, T, I, Y, W, L and R;

$X_4$ is a natural or modified amino acid residue chosen from: Y, A, S, F, W, L, T and M;

$X_5$ is a natural or modified amino acid residue chosen from: Y, M, L, A, F, and S;

$X_6$ is a natural or modified amino acid residue chosen from: L, T, and R;

$X_7$ is a natural or modified amino acid residue chosen from: Q and Y; and wherein the $N_1$ comprises an amino terminus, from about 1 to about 20 natural or modified amino acids and a fluorophore, or a chromophore; and wherein $N_2$ is a carboxy terminus, from about 1 to about 20 natural or modified amino acids and a fluorescent quencher, or a chromophore.

In some embodiments, the amino acid sequence comprises or consists of at least one amino acid sequence with the formula: DEGWALQH (SEQ ID NO: 1), VGKWSYRM (SEQ ID NO: 2), NMKWTRVL (SEQ ID NO: 3), PWTWYGVK (SEQ ID NO: 4), FGIFYLNG (SEQ ID NO: 5), HMIALYWG (SEQ ID NO: 6), IKILMFYW (SEQ ID NO: 7), GLYFRYE (SEQ ID NO: 8), or AGFSLPA (SEQ ID NO: 9) or those amino acid sequence that are at least about 70%, 80%, 85%, 86%, 87%, 88% homologous to SEQ ID NOS: 1, 2, 3, 4, 5, 6, 7, 8, and/or 9. In some embodiments, the substrates are bonded to one or a plurality of probes, such as an activity-based probe.

Substrates disclosed herein may also be lyophilized or dessicated in a container for storage and future use. In some embodiments, the disclosure relates to a composition comprising one or a plurality of substrates disclosed herein adsorbed, bound, or otherwise associated with a reaction vessel in a solid support or a bead, such as a magnetic bead. Solid supports can be tissue culture plates, plastic or polystyrene multiwall plates or other plastic element with one or a plurality of reaction vessels. Enzymes contained in a sample can be contacted with the one or more substrates within one or a plurality of reaction vessels on the plastic element for a time period sufficient to catalyze a reaction between the enzyme a substrate. In some embodiments, substrates may be encapsulated by or associated with nanodroplets. In some embodiments, reaction products such as cleavage product can be detected in solution or within the reaction vessel after exposure of the reaction vessel to one or a plurality of chemical stimuli for a chemiluminescent probe, visible or non-visible light that is capable of activated the electronic state of a fluorescent probe, or exposure to an antibody specific to the enzyme or substrate. In some embodiments, the substrates disclosed herein can be bound to the surface of the solid support where one or more of FRET analysis, Raman spectroscopy, mass spectroscopy, fluorescent microscopy or absorbance of light may be performed after the enzymatic reaction is complete.

In some embodiments, one or more species of substrate disclosed herein may be stored in a container for later use with a kit comprising the solid support.

Kits

In some embodiments, kits in accordance with the present disclosure may be used to culture and/or to propagate cells or mucinous cell types of interest. In some embodiments, kits in accordance with the present disclosure may be used to diagnose, prognose or calculate the likelihood that a subject has a pancreatic or mucinous cyst, a pancreatic ductal adenocarcinoma (PDA), an intraductal papillary mucinous neoplasm (IPMN), a mucinous cystic neoplasm (MCN), a serous cystadenoma (SCA), or a pseudocyst. In some embodiments, kits for culturing cells comprise any substrate or polypeptide described herein with an affinity to one or more biomarkers; and, optionally, further comprise cell culture medium and a control cell type of interest. Any array, system, or component thereof disclosed may be arranged in a kit either individually or in combination with any other array, system, or component thereof. The invention provides a kit to perform any of the methods described herein. In some embodiments, the kit comprises at least one container comprising one or a plurality of polypeptides comprising a polypeptide sequence with an affinity for the one or plurality of enzymes or functional fragments thereof disclosed herein. In some embodiments, the kit comprises at least one container comprising any of the polypeptides or functional fragments described herein. In some embodiments, the polypeptides are in solution (such as a buffer with adequate pH and/or other necessary additive to minimize degradation of the polypeptides during prolonged storage). In some embodiments, the polypeptides are lyophilized for the purposes of resuspension after prolonged storage. In some embodiments, the kit comprises: at least one container comprising one or a plurality of polypeptides comprising a polypeptide sequence associated with an aspartyl protease (or functional fragments thereof); and a solid support upon which polypeptides with affinity for any biomarkers for such synthesis or maintenance may be affixed. In some embodiments, the kit optionally comprises instructions to perform any or all steps of any method described herein. In some embodiments, the kit comprises an array or system described herein and instructions for implementing one or a plurality of steps using a computer program product disclosed herein. It is understood that one or a plurality of the steps from any of the methods described herein can be performed by accessing a computer program product encoded on computer storage medium directly through one or more computer processors or remotely through one or more computer processors via an internet connection or other virtual connection to the one or more computer processors. In some embodiments, the kit comprises a computer-program product described herein or requisite information to access a computer processor comprising the computer program product encoded on computer storage medium remotely. In some embodiments, the computer program product, when executed by a user, calculates one or more raw values of signal intensity, normalizes the one or more values into a one or more scores based upon values from a control sample, generates one or more protease signatures or one or more protease profiles, and/or displays any of the values, protease signatures, protease profiles to a user. In some embodiments, the kit comprises a computer program product encoded on a computer-readable storage medium that comprises instructions for performing any of the steps of the methods described herein. In some embodiments, the invention relates to a kit comprising instructions for providing one or more protease signatures, protease profiles, or any combination thereof. In some embodiments, the kit comprises a computer program product encoded on a computer storage medium that when, executed on one or a plurality of computer processors, quantifies a raw value corresponding to an amount of biomarker present in a sample, determines protease signatures or protease profiles, and/or displays the signature, value, signature, and/or any combination thereof. In some embodiments, the kit comprises a computer program product encoded on a computer storage medium that, when executed by one or a plurality of computer processors, quantifies values of one or more samples and determines a protease signature based at least partially upon the values corresponding to the amount of biomarker present in a sample. In some embodiments, kit comprises instructions for accessing the computer storage medium, quantifying values, normalizing the values, determining a signature of a protease, and/or any combination of steps thereof. In some embodiments, the computer-readable storage medium comprises instructions for performing any of the methods described herein. In some embodiments, the kit comprises an array or system disclosed herein and a computer program product encoded on computer storage medium that, when executed, performs any of the method steps disclosed herein individually or in combination and provides instructions for performing any of the same steps. In some embodiments, the instructions comprise an instructions to adhere any one or plurality of polypeptides disclosed herein to a solid support.

The invention further provides for a kit comprising one or a plurality of containers that comprise one or a plurality of the polypeptides or fragments disclosed herein. In some embodiments, the kit comprises cell media that enhances the culture or proliferation of cells. In some embodiments, the kit comprises: an array disclosed herein, any cell media disclosed herein, and a computer program product disclosed herein optionally comprising instructions to perform any one or more steps of any method disclosed herein. In some embodiments, the kit comprises a device for affixing one or more polypeptides disclosed herein to a solid support.

The kit may contain two or more containers, packs, or dispensers together with instructions for preparation of an array. In some embodiments, the kit comprises at least one container comprising the array or system described herein and a second container comprising a means for maintenance, use, and/or storage of the array such as storage buffer. In some embodiments, the kit comprises a composition comprising any polypeptide disclosed herein in solution or lyophilized or dried and accompanied by a rehydration mixture. In some embodiments, the polypeptides and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The invention also provides a kit comprising: an array of polypeptides, the array comprising: a solid support and a plurality of polypeptides capable of binding to one or a plurality of biomarkers disclosed herein. In some embodiments, the kit further comprises at least one of the following: cell media, a volume of fluorescent stain or dye, a cell sample, and a set of instructions, optionally accessible remotely through an electronic medium.

In some embodiments, the disclosure provides a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof. In some embodiments, the disclosure provides a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof. In some embodiments, the disclosure provides a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof, wherein the any one or plurality of substrates comprises a fluorogenic probe, the fluorescence of which correlates to the amount of substrate converted to a reaction product upon exposure to any one or more of the enzymes disclosed herein, or functional fragments thereof. In some embodiments, the solid support is a plastic plate arranged in a single well or multiplexed format. In some embodiments, the solid support is a multi-well plate (such as a 364-well plate) in which substrates labeled with fluorogenic probes are positioned within one or a plurality of the wells.

The disclosure provides for a kit comprising a solid support comprising one or a plurality of wells, receptacles or compartments addressable or accessible through at least one opening, at least one or a plurality of such wells, receptacles or compartments comprising one or a plurality of substrates specific for any one of the enzymes disclosed herein, or functional fragments thereof, wherein the any one or plurality of substrates comprises a fluorogenic probe, the fluorescence of which correlates to the amount of substrate converted to a reaction product upon exposure to any one or more of the enzymes disclosed herein, or functional fragments thereof. in some embodiments the substrates are capable of being cleaved upon exposure to any one or plurality of the enzymes disclosed herein. In some embodiments, the reaction products are quantifiable by fluorescence values obtained through use of a fluorimeter or spectrophotometer. In some embodiments, the reaction products are quantifiable by detecting fluorescence energy transfer of a fluorogenic probe exposed to a known wavelength of electromagnetic energy after a substrate, comprising the probe, is treated with a sample. One example of FRET measurements are provided for in US Application No. 20040191786, which is incorporated by reference in its entirety.

The disclosure also provides for kits comprising a solid support in one container and a series of containers comprising one or a plurality of substrates comprising amino acid sequences with cleavage sites specific for any one or plurality of enzymes that are at least 70% homologous to any of the enzymes disclosed herein.

Methods

The disclosure relates to methods of diagnosing and/or prognosing subjects comprising correlating the amount of aspartyl protease in a sample to the stage of disease. The present disclosure also relates to a method for characterizing the stage of development or pathology of a cyst from a subject comprising a hyperproliferative cell. In one aspect, the method of characterizing the stage of development or pathology of a cyst comprising a hyperproliferative cell comprises: (a) contacting one or a plurality of probes specific for cathepsin E and/or gastricsin and/or functional fragment thereof with a sample from a subject; (b) quantifying the amount of cathepsin E and/or gastricsin and/or functional fragment thereof in the sample; (c) calculating one or more normalized scores based upon the presence, absence, or quantity of cathepsin E and/or gastricsin and/or functional fragment thereof as compared to the presence, absence, or quantity of cathepsin E and/or gastricsin and/or functional fragment thereof in a control sample; and (d) correlating the one or more scores to the presence, absence, or quantity of cathepsin E and/or gastricsin and/or functional fragment thereof in the sample, such that if the amount of cathepsin E and/or gastricsin and/or functional fragment thereof from the subject is greater than the quantity of cathepsin E and/or gastricsin and/or functional fragment thereof in a control sample, the correlating step comprises characterizing the cyst as comprising a hyperproliferative cell.

In some embodiments, the present disclosure also relates to a method for characterizing the stage of development or pathology of a cyst from a subject as being cancerous or malignant. In one aspect, the method of characterizing the stage of development or pathology of a cyst comprises: (a) contacting one or a plurality of probes specific for cathepsin E and/or gastricsin and/or functional fragment thereof with a sample from a subject; (b) quantifying the amount of cathepsin E and/or gastricsin and/or functional fragment thereof in the sample; (c) calculating one or more normalized scores based upon the presence, absence, or quantity of cathepsin E and/or gastricsin and/or functional fragment thereof as compared to the presence, absence, or quantity of cathepsin E and/or gastricsin and/or functional fragment thereof in a control sample; and (d) correlating the one or more scores to the presence, absence, or quantity of cathepsin E and/or gastricsin and/or functional fragment thereof in the sample, such that if the amount of cathepsin E and/or gastricsin and/or functional fragments thereof from the subject is greater than the quantity of cathepsin E and/or gastricsin and/or functional fragments thereof in a control sample, the correlating step comprises characterizing the cyst as cancerous or malignant.

In some embodiments, the disclosure relates to methods of detecting an aspartyl protease in a subject, the methods comprising: detecting whether an aspartyl protease is present in a sample by contacting the sample with one or more probes specific for the aspartyl protease. In some embodiments, the method further comprises obtaining a sample from the subject prior to the step of detecting. In some embodiments, the step of detecting comprises detecting whether two aspartyl proteases are present in a sample by contacting the sample with a first probe specific for a first aspartyl protease and a second probe specific for a second aspartyl protease and detecting the binding between (i) the first probe and the first aspartyl protease; and (ii) the second probe and the second aspartyl protease. In some embodiments, the method further comprises using the same probes to detect the presence or quantity of the first and second aspartyl protease in a control sample by detecting the binding between (i) the first probe and the first aspartyl protease in the control sample; and (ii) the second probe and the second aspartyl protease in the control sample. If the control sample from a benign or non-cancerous sample, the methods may further comprise, in some embodiments, a step of comparing the binding between the control sample and the sample from the subject.

In some embodiments, the disclosure relates to a method of detecting increased binding of an aspartyl protease in a sample as compared to a control sample, the method comprising: (a) detecting whether one or two aspartyl proteases are present in a sample by contacting the sample with a first probe specific for a first aspartyl protease and a second probe specific for a second aspartyl protease and detecting the binding between (i) the first probe and the first aspartyl protease; and (ii) the second probe and the second aspartyl protease; and (b) comparing the binding between the control sample and the sample from the subject. In some embodiments, the disclosure relates to a method of diagnosing a subject with a malignant form of pancreatic cancer or mucinous cyst comprising any of the aforementioned steps (a) or (b) and further comprising (c) diagnosing the subject as having a malignant form of pancreatic cancer or mucinous cyst if the binding between (i) the first probe and the first aspartyl protease in the sample; and (ii) the second probe and the second aspartyl protease in the sample are greater than the binding between (i) the first probe and the first aspartyl protease in the control sample; and (ii) the second probe and the second aspartyl protease in the control sample. In some embodiments, the binding of the probes in the sample must be greater than or equal to about 1.1, 1.2 or 1.3 times the binding of the probes to the control.

In some embodiments, the method comprises using a probe comprising an amino acid sequence that is a substrate for the aspartyl protease or aspartyl proteases, such amino acid sequence comprises at least one amino acid sequence comprising the formula:

$$N_1—X_3—X_4—X_5—X_6—N_2$$

wherein:

$N_1$ is an amino terminus and/or one or a plurality of natural or modified amino acids, nucleic acids, or probes covalently or non-covalently attached to the terminus in any contiguous or non-contiguous order or pattern;

$X_3$ is a natural or modified amino acid residue independently selected from: any of the amino acid residues at a position immediately adjacent and contiguous to $X_4$ on its N terminal side in the amino acid orientation depicted in the Figures or Examples;

$X_4$ is a natural or modified amino acid residue independently selected from: any of the amino acid residues at a position immediately adjacent to a cleavage site on the N terminal side of the amino acid sequence depicted in the Figures or Examples;

$X_5$ is a natural or modified amino acid residue independently selected from: any of the amino acid residues at a position immediately adjacent to a cleavage site on the C terminal side of the amino acid sequence depicted in the Figures or Examples;

$X_6$ is a natural or modified amino acid residue chosen from: any of the amino acid residues at a position immediately adjacent and contiguous to $X_5$ on its carboxy terminal side in the amino acid orientation depicted in the Figures or Examples;

$N_2$ is a carboxy terminus or one or a plurality of natural or modified amino acids, nucleic acids, or probes covalently or non-covalently attached to the terminus in any contiguous or non-contiguous order or pattern; wherein $X_4$ and $X_5$ are the amino acid residues between which the enzyme or enzymes disclosed in the Figures cleaves the substrate (depicted by a vertical line in the Figures). In some embodiments, $X_4$ is independently selected from: Y, F, W, L, or norleucine or a modified residue thereof.

$X_5$ is independently selected from: Y, n, L, A, F, S or a modified residue thereof. In some embodiments, the method comprises using a probe comprising an amino acid sequence that is a substrate for the aspartyl protease or aspartyl proteases, such amino acid sequence comprises at least one amino acid sequence comprising the formula:

$$X_1—X_2—X_3—X_4$$

wherein $X_1$ is independently selected from: G, K, R, N, I, D, L, Q, T, M, norleucine, H, A, Y, or W;
wherein $X_2$ is independently selected from: W, L, Y, F, D, E, norleucine, or M;
wherein $X_3$ is independently selected from: A, F, L, Y, norleucine, M, I, S, W, or V;
wherein $X_4$ is independently selected from: L, R, V, H, Q, N, I, norleucine, M, T, Y, A, G, or E; and wherein $X_2$ and $X_3$ are the amino acid residues between which the first and/or second aspartyl protease cleaves the probe.

The present disclosure also relates to a method of determining whether a subject has a mucinous cyst or malignant growth. In one aspect, the method comprises: detecting the presence, absence, or quantity of gastricsin or functional fragment thereof in a sample from the subject comprising contacting the sample with a probe specific for gastricsin or functional fragment thereof, and/or a substrate specific for gastricsin or functional fragment thereof. In some embodiments, the method comprises: detecting the presence, absence, or quantity of cathepsin E or functional fragment thereof in a sample from the subject comprising contacting the sample with a probe specific for gastricsin or functional fragment thereof, and/or a substrate specific for Cathepsin E or functional fragment thereof. In some embodiments, the sample is pancreatic cyst fluid or cells from a pancreatic cyst. In some embodiments, the disclosure relates to a method of determining whether a subject has a mucinous cyst or malignant growth, the method comprising: (i) detecting the presence, absence, or quantity of gastricsin or functional fragment thereof in a sample from the subject comprising contacting the sample with a probe specific for gastricsin or functional fragment thereof, and/or a substrate specific for gastricsin or functional fragment thereof; and (ii) detecting the presence, absence, or quantity of cathepsin E or functional fragment thereof in a sample from the subject comprising contacting the sample with a probe specific for cathepsin E or functional fragment thereof, and/or a substrate specific for gastricsin or functional fragment thereof; and, optionally, (iii) comparing the quantity of gastricsin or functional fragment thereof in the sample and/or the quantity of cathepsin E or functional fragment thereof in the sample to the quantity of gastricsin or functional fragment thereof in a control sample and/or the quantity of cathepsin E or functional fragment thereof in a control sample, and, if the amount of gastriscin and/or cathepsin E is significantly higher than the amount of gastriscin and/or cathepsin E in the control, then classifying the subject as having a mucinous cyst or malignant growth.

The present disclosure also relates to a method of determining whether a subject has a mucinous cyst. In one aspect, the method comprises: detecting the presence, absence, or quantity of cathepsin E or functional fragment thereof in a sample from the subject by contacting the sample with a probe specific for cathepsin E or functional fragment thereof, and/or a substrate specific for cathepsin E or functional fragment thereof. In some embodiments, the method comprises: detecting the presence, absence, or quantity of gastricsin or functional fragment thereof in a sample from the subject by contacting the sample with a probe specific for gastricsin or functional fragment thereof, and/or a substrate specific for gastricsin or functional fragment thereof. In some embodiments, the disclosure relates to a method of determining whether a subject has a mucinous cyst or malignant growth, the method comprising: (i) detecting the presence, absence, or quantity of gastricsin or functional fragment thereof in a sample from the subject comprising contacting the sample with a probe specific for gastricsin or functional fragment thereof, and/or a substrate specific for gastricsin or functional fragment thereof; and (ii) detecting the presence, absence, or quantity of cathepsin E or functional fragment thereof in a sample from the subject comprising contacting the sample with a probe specific for cathepsin E or functional fragment thereof, and/or a substrate specific for gastricsin or functional fragment thereof; and, optionally, (iii) comparing the quantity of gastricsin or functional fragment thereof in the sample and/or the quantity of cathepsin E or functional fragment thereof in the sample to the quantity of gastricsin or functional fragment thereof in a control sample and/or the quantity of cathepsin E or functional fragment thereof in a control sample, and, if the amount of gastriscin and/or cathepsin E is significantly higher than the amount of gastriscin and/or cathepsin E in the control, then classifying the subject as having a mucinous cyst.

The present disclosure also relates to a method of detecting the presence of a pre-cancerous or cancerous cell in a subject. In one aspect, the method comprises: (a) contacting a one or a plurality of probes specific for cathepsin E and/or gastricsin and/or CEA and/or functional fragments thereof with a sample from the subject; (b) quantifying the amount of cathepsin E and/or gastricsin and/or CEA and/or functional fragment thereof in the sample; (c) calculating one or more normalized scores based upon the presence, absence, or quantity of cathepsin E and/or gastricsin and/or CEA and/or functional fragment thereof; and (d) correlating the one or more scores to the presence, absence, or quantity of cathepsin E and/or gastricsin and/or CEA and/or functional fragment thereof, such that if the amount of cathepsin E and/or gastricsin and/or CEA and/or functional fragment thereof is greater than the quantity of cathepsin E and/or gastricsin and/or CEA and/or functional fragment thereof in a control sample, the correlating step comprises characterizing the sample as comprising a pre-cancerous or cancerous cell.

The present disclosure also relates to a method of determining whether a subject has a mucinous cyst or malignant growth. In one aspect, the method comprises detecting the presence, absence, or quantity of CEA, wherein the sensitivity to detecting CEA is equal to or greater than about 70%.

The present disclosure relates to the detecting gastricsin in a subject, the method comprising: (i) obtaining a sample from the subject; and; (ii) detecting whether gastricsin is present at biologically significant levels within the sample by contacting the sample with a probe specific for gastricsin and detecting binding between gastricsin and the probe. The present disclosure also relates to the detecting cathepsin E in a subject, the method comprising: (i) obtaining a sample from the subject; and; (ii) detecting whether cathepsin E is present at biologically significant levels within the sample by contacting the sample with a probe specific for cathepsin E and detecting binding between cathepsin E and the probe. In some embodiments, the biologically significant levels of gastricsin, cathpesin E and/or functional fragments thereof within a sample are at or greater than about a 1 fold change in quantity as compared to the amount of gatricsin, cathepsin E or functional fragments thereof in a control sample (for instance, a sample known to be benign or noncancerous or non-malignant). In some embodiments, the biologically significant levels of gastricsin, cathpesin E and/or functional fragments thereof within a sample are at or greater than about a 1.1 fold change as compared to the amount of gatricsin, cathepsin E or functional fragments thereof in a control sample (for instance, a sample known to be benign or noncancerous or non-malignant). In some embodiments, the biologically significant levels of gastricsin, cathpesin E and/or functional fragments thereof within a sample are at or greater than about a 1.2 fold change as compared to the amount of gatricsin, cathepsin E or functional fragments thereof in a control sample (for instance, a sample known to be benign or noncancerous or non-malignant). In some embodiments, the biologically significant levels of gastricsin, cathpesin E and/or functional fragments thereof within a sample are at or greater than about a 1.3 fold change as compared to the amount of gatricsin, cathepsin E or functional fragments thereof in a control sample (for instance, a sample known to be benign or noncancerous or non-malignant). In some embodiments, the biologically significant levels of gastricsin, cathpesin E and/or functional fragments thereof within a sample are at or greater than about a 1.4 fold change as compared to the amount of gatricsin, cathepsin E or functional fragments thereof in a control sample (for instance, a sample known to be benign or noncancerous or non-malignant). In some embodiments, the biologically significant levels of gastricsin, cathpesin E and/or functional fragments thereof within a sample are at or greater than about a 1.5 fold change as compared to the amount of gatricsin, cathepsin E or functional fragments thereof in a control sample (for instance, a sample known to be benign or noncancerous or non-malignant). In some embodiments, the The present disclosure relates to the detecting gastricsin and/or cathepsin E in a subject, the method comprising: (i) obtaining a sample from the subject; and; (ii) detecting whether gastricsin and/or cathepsin E is present within the sample by contacting the sample with a probe specific for gastricsin and/or cathepsin E (or functional fragments thereof) and detecting binding between gastricsin and the probe specific for gatricsin and/or detecting the binding between cathepsin E and the probe specific for cathepsin E. The present disclosure also relates to the detecting functional fragments of gastricsin and/or functional fragments of cathepsin E in a subject, the method comprising: (i) obtaining a sample from the subject; and; (ii) detecting whether functional fragments of gastricsin and/or cathepsin E are present within the sample by contacting the sample with a probe specific for functional fragments of gastricsin and/or cathepsin E and detecting binding between functional fragments of gastricsin and the probe specific for gatricsin or functional fragments thereof and/or detecting the binding between functional fragments of cathepsin E and the probe specific for functional fragments of cathepsin E. In some embodiments, the probe is an antibody against cathepsin E. In some embodiments, the probe is an antibody against gastricsin. In some embodiments, the probe for cathepsin E is an amino acid sequence that comprises at least about 75% sequence identity to any one or combination of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9. In some embodiments, the one or plurality of probes comprise a chemiluminescent moiety or moiety that emits a wavelength of light detectable in the visual spectrum of color.

The present disclosure relates to a method of detecting gastricsin and/or cathepsin E in a subject, the method comprising: (i) obtaining a sample from the subject; and (ii) detecting whether gastricsin and/or cathepsin E is present within the sample by performing mass spectrometry and (i) detecting the mass of gastricsin and/or the mass of amino acid fragments of gastricsin; and/or (ii) detecting the mass of cathepsin E and/or the mass of amino acid fragments of cathepsin E. The present disclosure also relates to the detecting functional fragments of gastricsin and/or functional fragments of cathepsin E in a subject, the method comprising: (i) obtaining a sample from the subject; and; (ii) detecting whether functional fragments of gastricsin and/or cathepsin E are present within the sample by performing mass spectrometry and (i) detecting the mass of gastricsin and/or the mass of amino acid fragments of gastricsin;

and/or (ii) detecting the mass of cathepsin E and/or the mass of amino acid fragments of cathepsin E.

The present disclosure also relates to a method of detecting gastricsin and/or cathepsin E in a subject, the method comprising: (i) obtaining a sample from the subject; and; (ii) detecting whether gastricsin and/or cathepsin E is present within the sample at biologically significant levels by performing mass spectrometry and (i) detecting the mass of gastricsin and/or the mass of amino acid fragments of gastricsin; and/or (ii) detecting the mass of cathepsin E and/or the mass of amino acid fragments of cathepsin E. The present disclosure also relates to a method detecting functional fragments of gastricsin and/or functional fragments of cathepsin E in a subject, the method comprising: (i) obtaining a sample from the subject; and; (ii) detecting whether functional fragments of gastricsin and/or cathepsin E are present at biologically significant levels within the sample by performing mass spectrometry and (i) detecting the mass of gastricsin and/or the mass of amino acid fragments of gastricsin; and/or (ii) detecting the mass of cathepsin E and/or the mass of amino acid fragments of cathepsin E. In some embodiments, the mass amounts of the functional fragments of cathepsin E and/or gastricsin are compared to the mass amounts of the same functional fragments in a control sample (such as one known to be benign or noncancerous). In some embodiments, the biologically significant levels of mass amounts of gastricsin, cathpesin E and/or functional fragments thereof within a sample are at or greater than about a 1 fold change in amount as compared to the amount of gatricsin, cathepsin E or functional fragments thereof in a control sample (for instance, a sample known to be benign or noncancerous or non-malignant). In some embodiments, the biologically significant levels of mass amounts of gastricsin, cathpesin E and/or functional fragments thereof within a sample are at or greater than about a 1.1 fold change as compared to the amount of gatricsin, cathepsin E or functional fragments thereof in a control sample (for instance, a sample known to be benign or noncancerous or non-malignant). In some embodiments, the biologically significant levels of mass amounts of gastricsin, cathpesin E and/or functional fragments thereof within a sample are at or greater than about a 1.2 fold change as compared to the amount of gatricsin, cathepsin E or functional fragments thereof in a control sample (for instance, a sample known to be benign or noncancerous or non-malignant). In some embodiments, the biologically significant levels of mass amounts of gastricsin, cathpesin E and/or functional fragments thereof within a sample are at or greater than about a 1.3 fold change as compared to the amount of gatricsin, cathepsin E or functional fragments thereof in a control sample (for instance, a sample known to be benign or noncancerous or non-malignant). In some embodiments, the biologically significant levels of mass amounts of gastricsin, cathpesin E and/or functional fragments thereof within a sample are at or greater than about a 1.4 fold change as compared to the amount of gatricsin, cathepsin E or functional fragments thereof in a control sample (for instance, a sample known to be benign or noncancerous or non-malignant). In some embodiments, the biologically significant levels of mass amounts of gastricsin, cathpesin E and/or functional fragments thereof within a sample are at or greater than about a 1.5 fold change as compared to the amount of gatricsin, cathepsin E or functional fragments thereof in a control sample (for instance, a sample known to be benign or noncancerous or non-malignant).

The disclosure relates to a method of diagnosing malignant pancreatic cancer in a subject, said method comprising: (i) obtaining a sample from a subject; (ii) detecting whether gastricsin or a functional fragment thereof is in the sample by contacting the sample with one or a plurality of probes specific for gastricin or a functional fragment thereof and detecting binding between gastricsin and/or a functional fragment thereof and the one or plurality of probes specific for gastricin or a functional fragment thereof; and (iii) diagnosing the subject with malignant pancreatic cancer when the presence of gastricsin or a functional fragment thereof is detected. The disclosure relates to a method of diagnosing malignant pancreatic cancer in a subject, said method comprising: (i) obtaining a sample from a subject; (ii) detecting whether cathepsin E or a functional fragment thereof is in the sample by contacting the sample with one or a plurality of probes specific for cathepsin E or a functional fragment thereof and detecting binding between cathepsin E and/or a functional fragment thereof and the one or plurality of probes specific for cathepsin E or a functional fragment thereof; and (iii) diagnosing the subject with malignant pancreatic cancer when the presence of cathepsin E or a functional fragment thereof is detected.

The disclosure relates to a method of diagnosing malignant pancreatic cancer in a subject, said method comprising: (i) obtaining a sample from a subject; (ii) detecting whether gastricsin or a functional fragment thereof is in the sample by contacting the sample with one or a plurality of probes specific for gastricin or a functional fragment thereof and detecting binding between gastricsin and/or a functional fragment thereof and the one or plurality of probes specific for gastricin or a functional fragment thereof; and (iii) diagnosing the subject with malignant pancreatic cancer when the presence of gastricsin or a functional fragment thereof is detected at levels that are at least about 1 times greater than the levels of gastricsin or a functional fragment thereof in a control sample. The disclosure relates to a method of diagnosing malignant pancreatic cancer in a subject, said method comprising: (i) obtaining a sample from a subject; (ii) detecting whether cathepsin E or a functional fragment thereof is in the sample by contacting the sample with one or a plurality of probes specific for cathepsin E or a functional fragment thereof and detecting binding between cathepsin E and/or a functional fragment thereof and the one or plurality of probes specific for cathepsin E or a functional fragment thereof; and (iii) diagnosing the subject with malignant pancreatic cancer when the presence of cathepsin E or a functional fragment thereof is detected at levels that are at least about 1 times greater than the levels of cathepsin E or a functional fragment thereof in a control sample. In some embodiments, the amount of gatriscin or functional fragments thereof in a sample is detected sequentially, contemporaneously or after detecting the amount of cathepsin E or functional fragment is detected in the same sample. In some embodiments, the levels of either or both aspartyl proteases are detected with one or a plurality of probes specific for either or both aspartyl proteases, wherein the probe comprises an amino acid sequence that is a substrate for the particular aspartyl protease being detected. In some embodiments, if the aforementioned one or plurality of probes comprise one or a plurality of substrates for the aspartyl proteases, the presence or quantity of: (i) cathepsin E or a functional fragment thereof; and/or (ii) gastricsin or a functional fragment thereof is measured by detecting the presence or quantity of reaction products produced by exposure of the aspartyl proteases to their respective substrates. In some embodiments, the reaction products are cleaved amino acid sequences of the substrates comprising at least one amino acid sequence comprising the formula:

$$N_1\text{-}X_3\text{-}X_4\text{-}X_5\text{-}X_6\text{-}N_2 \quad \text{(SEQ ID NO: 50)}$$

wherein:

$N_1$ is an amino terminus and/or one or a plurality of natural or modified amino acids, nucleic acids, or probes covalently or non-covalently attached to the terminus in any contiguous or non-contiguous order or pattern;

$X_3$ is a natural or modified amino acid residue independently selected from: A, H, N, Q, G, F, K, D, M, T, I, Y, W, L, norleucine, and R;

$X_4$ is a natural or modified amino acid residue independently selected from: D, E, Y, A, S, F, W, H, L, T, norleucine, and M;

$X_5$ is a natural or modified amino acid residue independently selected from: Y, D, E, I, norleucine, M, L, A, F, and S;

$X_6$ is a natural or modified amino acid residue chosen from: L, V, H, Q, N, I, norleucine, Y, A, G, E, T, and R; and $N_2$ is a carboxy terminus or one or a plurality of natural or modified amino acids, nucleic acids, or probes covalently or non-covalently attached to the terminus in any contiguous or non-contiguous order or pattern; and wherein $X_3$ and $X_4$ flank the amide bond upon which a cleavage reaction is performed by the enzyme. In some embodiments, the reaction products are cleaved amino acid sequences of substrates comprising at least one amino acid sequence comprising any of the disclosed amino acid formula.

The disclosure relates to a method of diagnosing malignant pancreatic cancer in a subject, said method comprising: (i) obtaining a sample from a subject; (ii) detecting whether cathepsin E or a functional fragment thereof is in the sample by contacting the sample with one or a plurality of probes specific for cathepsin E or a functional fragment thereof and detecting binding between cathepsin E and/or a functional fragment thereof and the one or plurality of probes specific for cathepsin E or a functional fragment thereof; and (iii) diagnosing the subject with malignant pancreatic cancer when the presence of cathepsin E or a functional fragment thereof is detected at levels that are at least about 1.1, 1.2 or 1.3 times greater than the levels of cathepsin E or a functional fragment thereof in a control sample. The disclosure relates to a method of diagnosing malignant pancreatic cancer in a subject, said method comprising: (i) obtaining a sample from a subject; (ii) detecting whether gastricsin or a functional fragment thereof is in the sample by contacting the sample with one or a plurality of probes specific for gastricsin or a functional fragment thereof and detecting binding between gastricsin and/or a functional fragment thereof and the one or plurality of probes specific for gastricsin or a functional fragment thereof; and (iii) diagnosing the subject with malignant pancreatic cancer when the presence of gastricsin or a functional fragment thereof is detected at levels that are at least about 1.1, 1.2 or 1.3 times greater than the levels of gastricsin or a functional fragment thereof in a control sample.

The disclosure relates to a method of diagnosing malignant pancreatic cancer in a subject, said method comprising: (i) obtaining a sample from a subject; (ii) detecting whether an aspartyl protease or a functional fragment thereof is in the sample by contacting the sample with one or a plurality of probes specific for the aspartyl protease or a functional fragment thereof and detecting binding between the aspartyl protease and/or a functional fragment thereof and the one or plurality of probes specific for the aspartyl protease or a functional fragment thereof; and (iii) diagnosing the subject with malignant pancreatic cancer when the presence of the aspartyl protease or a functional fragment thereof is detected. The disclosure relates to a method of diagnosing malignant pancreatic cancer in a subject, said method comprising: (i) obtaining a sample from a subject; (ii) detecting whether an aspartyl protease or a functional fragment thereof is in the sample by contacting the sample with one or a plurality of probes specific for the aspartyl protease or a functional fragment thereof and detecting binding between the aspartyl protease and/or a functional fragment thereof and the one or plurality of probes specific for the aspartyl protease or a functional fragment thereof; and (iii) diagnosing the subject with malignant pancreatic cancer when the presence of the aspartyl protease or a functional fragment thereof is detected at levels that are at least about 1.00, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.35, 1.40 or 1.45 times greater than the levels of aspartyl protease or a functional fragment thereof in a control sample. In some embodiments, the step of detecting the presence of the aspartyl protease comprises contacting and detecting the aspartyl protease or functional fragment thereof with one or a plurality of probes specific for one or a plurality of aspartyl proteases. In some embodiments, the method comprises contacting a sample with at least two probes, one probe specific for cathepsin E and one probe specific for gastricsin, in which case the step of detecting comprises contacting and detecting the presence or quantity of two aspartyl proteases sequentially in either order or contemporaneously. In some embodiments, the probes for the aspartyl proteases comprise one or a plurality of probes comprising one or a combination of any formula of amino acid sequences disclosed in the application. In some embodiments, the probe or probes comprise at least one or more contiguous or non-contiguous amino acid sequences specific for aspartyl protease cleavage. In some embodiments, the method comprises a step for contacting and detecting the presence or quantity of aspartyl protease in a sample by correlating the amount of reaction product produced when the aspartyl protease is in contact with a substrate specific for the protease. In some embodiments, the substrate comprises no more than about 4, 5, 6, 7, 8, or more amino acids specific for a cleavage site of the aspartyl protease enzymatic activity. In some embodiments, the step of detecting the presence or quantity of aspartyl protease comprises contacting the aspartyl protease with a probe comprising an antibody specific for the aspartyl protease or functional fragment thereof. In some embodiments, the step of detecting the presence or quantity of aspartyl protease comprises contacting the aspartyl protease with a probe comprising an antibody specific for the aspartyl protease or functional fragment thereof and detecting the presence or quantity of aspartyl protease in the sample based upon binding between the aspartyl protease and/or a functional fragment thereof and the one or plurality of antibodies specific for the aspartyl protease, individually or collectively, or a functional fragment thereof in the sample. In some embodiments, the step of detecting the presence or quantity of aspartyl protease comprises performing mass spectrometry and determining the mass of the aspartyl protease subtypes within the sample.

In some embodiments, any of the disclosed methods comprise a step of detecting the presence of one, two or more aspartyl proteases within a sample by performing mass spectrometry and diagnosing the subject as having pancreatic cancer or a mucinous cyst when the presence of the one, two or more aspartyl proteases is in the sample. In some embodiments, any of the disclosed methods comprise a step of detecting the presence of one, two or more aspartyl proteases within a sample by performing mass spectrometry and diagnosing the subject as having pancreatic cancer or a mucinous cyst when the presence of the one, two or more aspartyl proteases is in the sample in quantities at least about 1.2, 1.3, 1.4, 1.5 or 1.6 or more times greater than the amount of the one, two or more aspartyl proteases in a control sample.

In any of the disclosed methods, the step of detecting the presence or quantity of a particular aspartyl protease is quantitated by measuring the fluorescence, colorimetric absorbance or intensity or chemiluminescence of a probe specific for the one or more aspartyl proteases, normalizing the quantities based upon a control sample or value and calculating a score. In such embodiments, any of the disclosed methods comprise diagnosing a subject as having a mucinous cyst or malignant pancreatic cancer if the score for a given aspartyl protease is significantly higher than the score of control sample.

In some embodiments, the disclosure relates to methods of diagnosing malignant pancreatic cancer or mucinous pancreatic cyst in a subject comprising (i) obtaining a sample from the subject; (ii) detecting the presence or quantity of any one or two or more aspartyl proteases in the sample by contacting the sample with an antibody specific for the one or two or more aspartyl proteases and detecting the binding between the one or two or more aspartyl proteases and the antibodies specific for the one or two or more aspartyl proteases; and (iii) diagnosing the subject with malignant pancreatic cancer or as having a mucinous pancreatic cyst when the presence or quantity of aspartyl proteases is detected or quantified to a biologically significant value.

In some embodiments, any of the methods disclosed herein comprise a step of detecting the presence or quantity of aspartyl protease with a sensitivity of no less than about 10 nM of aspartyl protease concentration in a sample. In some embodiments, any of the methods disclosed herein comprise a step of detecting the presence or quantity of aspartyl protease with a sensitivity of no less than about 10, 11, 12, 13, 14, 15, 16, 17, 18, 19, 20, 21, 22, 23, 24, 25, 30, 35, 40, 45, 50, 55, 60, 65, 70, 75, 80, 85, 90, 91, 92, 93, 94, or 95 nM of aspartyl protease concentration in a sample.

Any and all journal articles, patent applications, issued patents, or other cited references disclosed herein (including GenBank Accession numbers or other genetic information identification tags dated as of the date of the application filing) are incorporated by reference in their respective entireties. Any of the systems, methods or devices disclosed herein comprising proteases may be made or performed or used with any of the proteases disclosed herein. In some embodiments, the systems, methods or devices disclosed herein are selectively free of any one or combination of enzymes disclosed herein.

EXAMPLES

Example 1: Materials and Methods

Patients and Sample Acquisition.

Pancreatic cyst fluid samples were collected from preconsented patients under institutional review board oversight. All patients included in the study underwent surgical resection of their cystic lesion and have a pathologically confirmed diagnosis. The highest grade of dysplasia observed during pathological evaluation of each cystic lesion is reported. Samples were collected either at the time of surgical resection or during diagnostic endoscopic ultrasound prior to resection of the cystic lesion. Cyst fluid samples were split into 100 µL aliquots and frozen to −80° C. within 60 minutes of collection. Samples underwent at most two freeze-thaw cycles prior to experimental analysis. Total cyst fluid protein concentration was determined by the bicinchoninic acid assay. CEA levels were evaluated for the majority of samples, but were unavailable in 21 cases due to limited cyst fluid volume.

Multiplex Substrate Profiling by Mass Spectrometry (MSP-MS) Assay.

The MSP-MS assay was performed as previously described (34). Cyst fluid was diluted to 100 µg/mL in assay buffer (either pH 7.5 phosphate buffer or pH 3.5 acetate buffer) and pre-incubated for 10 minutes. For analysis of protease inhibitor sensitivity, 1 mM AEBSF (Sigma, A8456), 2 µM E-64 (Sigma, E3132), 2 µM pepstatin (Sigma, P5318), 2 mM 1,10-phenanthroline (Sigma, 131337), or DMSO were included in pre-incubation. The 228 tetradecapeptide library was split into two pools and diluted in assay buffer to a concentration of 1 µM of each peptide. 75 µL of diluted cyst fluid and peptide pools were then combined and incubated at room temperature. 30 µL aliquots were removed after 15 and 60 minutes, protease activity quenched with 8 M guanidinium hydrochloride, and flash-frozen in liquid $N_2$. For recombinant gastricsin (R&D Systems, 6186-AS), cathepsin D (R&D Systems, 1014-AS), and cathepsin E (R&D Systems, 1294-AS), the MSP-MS assay was performed as described above with slight modifications: 10 nM of recombinant protease in pH 3.5 acetate buffer was used and aliquots were removed after 15, 60, and 240 minutes.

Prior to peptide cleavage site identification by mass spectrometry, samples were desalted using C18 tips (Rainin). Mass spectrometry analysis was carried out with an LTQ Orbitrap XL mass spectrometer coupled to a 10,000 psi nanoACQUITY Ultra Performance Liquid Chromatography (UPLC) System (Waters) for peptide separation by reverse phase liquid chromatography (RPLC). Peptides were separated over a C18 column (Thermo) and eluted by applying a flow rate of 300 nL/min with a 65-minute linear gradient from 2-30% acetonitrile. Survey scans were recorded over a 325-1500 m/z range and the six most intense precursor ions were fragmented by collision-induced dissociation (CID) for MS/MS.

Raw mass spectrometry data was processed to generate peak lists using MSConvert. Peak lists were then searched in Protein Prospector v. 5.10.0 (35) against a custom database containing the sequences from the 228 tetradecapeptide library. Searches used a mass accuracy tolerance of 20 ppm for precursor ions and 0.8 Da for fragment ions. Variable modifications included N-terminal pyroglutamate conversion from glutamine or glutamate and oxidation of tryptophan, proline, and tyrosine. Searches were subsequently processed using the MSP-xtractor software (http://www.craiklab.ucsf.edu/extractor.html), which extracts the peptide cleavage site and spectral counts of the corresponding cleavage products. Spectral counts were used for the relative quantification of peptide cleavage products.

Proteomic Analysis of Cyst Fluid Samples.

Cyst fluid samples were processed for proteomic analysis using a standard protocol. Briefly, 8 µg of cyst fluid protein was denatured in 40 µL of 6 M urea. Disulfide bonds were reduced with 10 mM dithiothreitol and free thiols were subsequently alkylated with 12.5 mM iodoacetamide. Samples were then diluted to with 25 mM ammonium bicarbonate to 2 M urea and digested with 100 ng trypsin for 16 hours at 37° C. Following trypsin digestion, samples were desalted with C18 tips (Rainin), dried, and resuspended in 0.1% formic acid.

Triplicate LC-MS/MS analysis of all samples was performed on an LTQ Orbitrap XL mass spectrometer and UPLC system described above. Peptides were separated by RPLC over a C18 column (Thermo). A 60-minute linear gradient from 2-15% acetonitrile with a flow rate of 300 nL/min was used for elution of peptides. Survey scans were recorded over a 325-1500 m/z range. The six most intense precursor ions from each survey scan were fragmented by collision-induced dissociation (CID) for MS/MS analysis.

Peak lists were generated using an in-house software called PAVA and searched in Protein Prospector v. 5.10.0 (35). Peak lists were searched against all human protein sequences in the SwissProt database (downloaded Dec. 1, 2015 with 549,832 sequence entries). This database was concatenated with a fully randomized set of entries to estimate the false discovery rate (FDR). For database searches, peptides sequences were matched to tryptic peptides with up to two missed cleavages. Carbamidomethylation of cysteine residues was used as a constant modification and variable modifications included oxidation of methionine, N-terminal pyroglutamate from glutamine, N-terminal acetylation, and loss of N-terminal methionine. The mass accuracy tolerance was set to 20 ppm for precursor ions and 0.8 Da for fragment ions. Protein Prospector score thresholds of 22 for the protein score and 15 for the peptide score were used and yielded a FDR of less than 1%. All reported proteins were identified by at least 2 unique peptides.

Label-free quantitation was used to compare relative abundance of the three aspartyl proteases identified in cyst fluid samples. The Skyline software package was used to obtain extracted ion chromatograms and peak areas for precursor ions from the aspartyl proteases (36). To correct for potential differences in protein loading between runs, peak areas were normalized by the median peak area of all fragmented ions from that run. The average peak area of the precursor ions from a given aspartyl protease was then used to estimate the abundance in each cyst fluid sample.

Western Blots of Gastricsin and Cathepsin E.

Cyst fluid protein (2 µg) or recombinant protease (20 ng) was pre-incubated for 30 minutes in either pH 7.5 phosphate buffer or pH 3.5 acetate buffer. Samples were then subjected to electrophoresis on a 10% NuPAGE Bis-Tris gel. Proteins were transferred to polyvinylidene fluoride membranes and blocked in Tris-buffered saline with 0.1% Tween (TBS-T) and 5% (w/v) non-fat dry milk for 2 hours at room temperature. Membranes were then incubated with either rabbit anti-gastricsin antibody (1:500; Abcam, ab104595) or rabbit anti-cathepsin E antibody (1:1,000; Abcam, ab49800) for 1 hour at room temperature. Following a wash in TBS-T, horseradish peroxidase (HRP)-conjugated secondary antibody (1:15,000; Abcam, ab97051) was applied for 2 hours at room temperatures. Proteins were detected with the enhanced chemiluminescence (ECL) detection system (Thermo).

Animal Strains.

The following mice strains were used: Ptf1a-Cre (gift of Christopher Wright, Vanderbilt University, Nashville, Tenn., USA), LSL-Kras$^{G12D}$ (gift of Dave Tuveson, Cold Spring Harbor Laboratory, USA), Brg1$^{f/f}$(gift of David Reisman, University of Florida, USA with permission of Pierre Chambon). Mice were crossed on a mixed background. The UCSF Institutional Care and Use of Animals Committee (IACUC) approved all mouse experiments.

Immunohistochemical Analysis of Pancreatic Tissue.

Tissue samples were obtained from patients who underwent resection of pancreatic cystic lesions at UCSF. Gastricsin and cathepsin E immunohistochemistry assays were developed and performed on a Ventana Discovery Ultra automated slide stainer (Ventana Medical Systems). In brief, formalin-fixed, paraffin-embedded (FFPE) samples (4 µm sections) were deparaffinized using EZPrep (Ventana Medical Systems) followed by treatment with antigen retrieval buffer (Ventana Medical Systems, 950-124). Specimens were incubated with either goat anti-gastricsin antibody (1:300; Santa Cruz, sc-51185) or goat anti-cathepsin E antibody (1:200; Santa Cruz, sc-6508) for 32 minutes at 36° C. OmniMap anti-goat secondary antibody (Ventana Medical Systems, 760-4647) was then applied for 16 minutes before employing a DAB detection kit (Ventana Medical Systems, 760-500). H&E staining of tissue sections was performed using standard protocols.

Mouse pancreatic tissue samples were collected from 8 Ptf1a-Cre; LSL-Kras$^{G12D}$; Brg1$^{f/f}$ animals between 3 and 40 weeks of age. FFPE samples (5 m sections) were deparaffinized with xylene and subsequently rehydrated. Sections were either subjected to H&E staining or heat-induced epitope retrieval with Citra buffer (BioGenex; HK086). Primary antibodies (goat anti-mouse) for cathepsin E (1:1, 000; R&D Systems; AF1130) and gastricsin (1:1,000; Santa Cruz; sc-51188) were incubated with sections overnight at 4° C. Anti-goat secondary antibody (1:200; Vector Labs; BA-9500) was then added to sections for 1 hour at room temperature. ABC (Vector Labs; PK-6100) and DAB kits (Vector Labs; SK-4100) were employed for detection.

Peptide Synthesis.

Synthesis of internally quenched fluorescent peptides was conducted using Fmoc solid-phase peptide synthesis on a Syro II automated synthesizer (Biotage). Briefly, reactors were charged with Wang resin preloaded with Fmoc-Lys (dinitrophenol) (Anaspec, A23856). Coupling reactions were conducted on a 0.0125 mmol scale in 500 µL of DMF with 5 equivalents of Fmoc amino acid (Anaspec), 4.9 equivalents of HCTU (Anaspec), and 20 equivalents of N-methylmorpholine (NMM). Fmoc deprotection was conducted by incubation with 500 µL 40% 4-methlypiperidine in DMF, followed by 500 µL 20% 4-methlypiperidine in DMF. Substrates were capped with a C-terminal Lys-(7-methoxycoumarin-4-acetic acid)-OH (EMD Millipore, 852095) followed by two D-Arg residues to enhance solubility. Peptides were removed from resin by incubating with 500 µL of cleavage solution (95% trifluoroacetic acid, 2.5% water, 2.5% Triisopropylsilane). Crudes were precipitated in 10 mL cold diethyl ether and isolated by centrifugation. Peptides were purified by HPLC and the correct mass was confirmed by matrix-assisted laser desorption/ionization time-of-flight mass spectrometry.

Fluorescent Protease Activity Assays.

All fluorescent protease activity assays were performed in triplicate in black, round-bottom 384 well plates. Assays were run for 1 hour in 15 µL of acetate buffer with 0.01% Tween. The pH of the acetate buffer was adjusted to promote activity of either aspartyl protease (pH 3.5 for the cathepsin E substrate and pH 2.0 for the gastricsin substrate). 10 µM of substrate was used for all assays (unless otherwise indicated) and was incubated with either 10 nM of recombinant protease or 50 µg/mL of cyst fluid protein. For kinetic analysis of gastricsin activity, the substrate concentration ranged from 0.1-25 µM. For analysis of inhibitor sensitivity, cyst fluid samples were pre-incubated with 2 µM of pepstatin. Fluorescent substrate cleavage was monitored with a Biotek Synergy HT plate reader using excitation and emission wavelengths of 328 nm and 393 nm, respectively. Selectivity of the recombinant proteases was assessed by comparing the initial velocity of substrate hydrolysis in relative fluorescent units per second (RFU/sec). For cyst fluid samples, the change in endpoint RFU was compared relative to wells that contained substrate, but no cyst fluid.

Statistical Analysis and Data Presentation.

A two-tailed Mann-Whitney U test was used to compare the differences in CEA abundance, gastricsin activity, and cathepsin E activity between mucinous and nonmucinous cysts. Univariate and multivariate logistic regression models were used for cyst prediction. Receiver operating characteristic (ROC) curves and Youden's J statistic were employed to identify the optimal cutoff. All mass spectrometry data (spectral counts and peak areas) was log 2 transformed and analyzed with unpaired two-tailed t-tests. GraphPad Prism was used to fit kinetic data and generate scatter plots and bar charts. Volcano plots, heat maps, venn diagrams, ROC curves, and logistic regression models were generated in RStudio v. 0.98.1091. iceLogo software was used to visualize patterns in peptide cleavage sites at ±4 positions away from the scissile bond (37).

Icelogo is a web service for visualizing conserved patterns in protein and nucleotide sequences through probability theory. They rely on Shannon's information theory (Shannon, Claude E. (July 1948). "A Mathematical Theory of Communication". *Bell System Technical Journal.* 27 (3): 379-423.), incorporated herein by reference in its entirety, to calculate the conservation level in a multiple sequence alignment. Usually represented as vertical stacks of symbols, the stack height reflects the level of conservation and the height is a measure for their frequency at a given position. Further information may be found at https://iomics.ugent.be/icelogoserver.

Example 2: Results

Global Protease Activity Profiling of Patient Cyst Fluid.

To identify differences in proteolytic activity between mucinous and nonmucinous cysts, the MSP-MS assay was used, which is a global and unbiased substrate-based protease profiling approach (34). In the MSP-MS assay, a physicochemically diverse library of 228 tetradecapeptide substrates is incubated with a protease-containing sample of interest and tandem mass spectrometry is used to monitor protease-derived peptide cleavage products. This assay has previously been validated using all classes of protease and it has been used to develop selective substrate probes (38-40).

Using the MSP-MS assay, 16 mucinous and 7 nonmucinous cyst fluid samples were profiled. To capture a broad range of protease activities, the assay was performed under acidic conditions and at neutral pH. At pH 7.5, a total of 1117 unique peptide cleavages were detected among the patient sample set (FIG. 1A). Only 7 peptide cleavages met the selectivity criteria for differentiating mucinous from nonmucinous cysts (+/-1 $\log_2$ (mucinous/nonmucinous), p<0.05). Six of these cleavages were enriched in nonmucinous cysts, and overall, there was a slight trend toward increased proteolytic activity in fluid from nonmucinous cysts (FIG. 6A). When the same samples were assayed at pH 3.5, a total of 691 peptide cleavages were detected, and increased proteolytic activity was observed in the mucinous cysts (FIG. 1B and FIG. 6B). All 35 unique substrate cleavages that differentiated mucinous from nonmucinous cysts were enriched in the mucinous set. The degree of dysplasia within a mucinous cyst is also an important factor in determining whether surgical intervention is recommended. However, no major differences in protease activity were evident between mucinous cysts with low- or high-grade dysplasia (FIG. 7A-FIG. 7B).

An iceLogo frequency plot was generated to visualize the substrate specificity pattern of the 35 mucinous-specific peptide cleavages detected at pH 3.5 (FIG. 1C) (37). At the P1 and P1' positions, which flank the cleavage site, there was a predominant enrichment of hydrophobic amino acids with the aromatic residues tyrosine and tryptophan more favored at P1. This mirrors the previously reported substrate specificity of lysosomal aspartyl proteases (41,42). The quantitative frequency data is also found in Table 4 below.

TABLE 4

The frequency (%) of amino acids at various positions relative to the scissile bond (between P1 and P1'). Frequency is for the 35 substrates whose cleavage was enriched in mucinous pancreatic cysts.

| Position | G | A | S | P | V | T | L | I | N | D |
|---|---|---|---|---|---|---|---|---|---|---|
| Frequency P4 | 5.7% | 0.0% | 5.7% | 2.9% | 2.9% | 5.7% | 2.9% | 2.9% | 0.0% | 8.6% |
| Frequency P3 | 11.4% | 2.9% | 2.9% | 5.7% | 5.7% | 2.9% | 2.9% | 14.3% | 5.7% | 0.0% |
| Frequency P2 | 2.9% | 2.9% | 0.0% | 0.0% | 0.0% | 5.7% | 5.7% | 8.6% | 11.4% | 11.4% |
| Frequency P1 | 0.0% | 0.0% | 0.0% | 0.0% | 0.0% | 0.0% | 8.6% | 0.0% | 0.0% | 2.9% |
| Frequency P1' | 0.0% | 14.3% | 8.6% | 0.0% | 2.9% | 0.0% | 14.3% | 8.6% | 0.0% | 0.0% |
| Frequency P2' | 2.9% | 5.7% | 0.0% | 0.0% | 11.4% | 8.6% | 8.6% | 5.7% | 2.9% | 0.0% |
| Frequency P3' | 5.7% | 5.7% | 2.9% | 0.0% | 14.3% | 2.9% | 11.4% | 0.0% | 2.9% | 0.0% |
| Frequency P4' | 0.0% | 8.6% | 0.0% | 2.9% | 0.0% | 5.7% | 0.0% | 2.9% | 17.1% | 2.9% |

| Position | Q | K | E | n | H | F | R | Y | W |
|---|---|---|---|---|---|---|---|---|---|
| Frequency P4 | 0.0% | 8.6% | 5.7% | 8.6% | 5.7% | 2.9% | 8.6% | 5.7% | 0.0% |
| Frequency P3 | 2.9% | 0.0% | 5.7% | 5.7% | 0.0% | 8.6% | 2.9% | 8.6% | 8.6% |
| Frequency P2 | 14.3% | 11.4% | 0.0% | 2.9% | 5.7% | 0.0% | 11.4% | 2.9% | 2.9% |
| Frequency P1 | 0.0% | 0.0% | 8.6% | 8.6% | 0.0% | 28.6% | 0.0% | 22.9% | 20.0% |
| Frequency P1' | 0.0% | 0.0% | 0.0% | 11.4% | 0.0% | 22.9% | 0.0% | 8.6% | 8.6% |
| Frequency P2' | 8.6% | 0.0% | 8.6% | 8.6% | 2.9% | 0.0% | 20.0% | 2.9% | 0.0% |
| Frequency P3' | 11.4% | 0.0% | 0.0% | 11.4% | 0.0% | 11.4% | 5.7% | 8.6% | 2.9% |
| Frequency P4' | 0.0% | 5.7% | 2.9% | 11.4% | 8.6% | 2.9% | 5.7% | 0.0% | 2.9% |

Identification of Cathepsin E and Gastricsin in Mucinous Cysts.

The specific proteases within the mucinous cysts that are responsible for the increased acid-optimal cleavage of the 35 mucinous-specific substrates were next identified. To aid in the characterization of protease activity, the initial focus was a single mucinous cyst fluid sample that cleaved 30 out of the 35 substrates.

The cyst fluid was treated with broad-spectrum inhibitors against all major protease classes and changes in cleavage of the 35 mucinous-specific substrates were analyzed by MSP-MS (FIG. 2A). Treatment with the aspartyl protease inhibitor pepstatin fully inhibited cleavage of 20 mucinous-specific substrates and partially inhibited cleavage of 8 additional substrates. The other broad-spectrum protease inhibitors minimally affected cleavage of the mucinous-specific substrates. The serine protease inhibitor AEBSF and the metal chelator 1,10-phenanthroline only inhibited cleavage of 3 substrates each. In a second mucinous cyst fluid sample, aspartyl protease inhibition with pepstatin was confirmed to block cleavage of the majority of the mucinous-specific substrates (FIG. 8).

The inhibition data demonstrated that aspartyl proteases have increased activity in mucinous cysts. Therefore, shotgun proteomic analysis was performed on a set of mucinous (n=4) and nonmucinous cysts (n=3) to determine if there were differences in the abundance of individual aspartyl proteases. This analysis identified three aspartyl proteases—cathepsin D, cathepsin E, and gastricsin. Label-free quantitation, using precursor ion abundance, revealed that cathepsin D was present at similar levels in the mucinous and nonmucinous cysts, whereas cathepsin E and gastricsin were significantly more abundant in the mucinous cysts (FIG. 2B). Aspartyl proteases are synthesized as inactive zymogens that undergo enzymatic maturation at an acidic pH (43). As the tumor microenvironment is known to be acidic, cathepsin E and gastricsin were investigated for their presence in the pro- or mature forms. Exposure of fluid from a mucinous cyst to acidic pH induced a mass shift in cathepsin E and gastricsin that was comparable to that observed using recombinantly produced proteins (FIG. 2C), indicating that both proteases are released into cyst fluid in their proforms. As expected, no cathepsin E or gastricsin was detected in fluid from a representative nonmucinous cyst. Collectively, these results demonstrate that the proforms of cathepsin E and gastricsin are differentially expressed in mucinous cysts and that this induction is responsible for the increased proteolytic activity under acidic conditions.

Immunohistochemical Analysis of Gastricsin and Cathepsin E in Mucinous cysts.

The overexpression of cathepsin E and gastricsin in 14 mucinous cysts was further examined using immunohistochemical (IHC) analysis. Cytoplasmic gastricsin staining was observed in the epithelial cells lining 11 of the 14 mucinous cysts examined. Interestingly, gastricsin expression was primarily associated with regions of low-grade dysplasia, and no staining was observed in regions of high-grade dysplasia (FIG. 3A-FIG. 3D). Gastricsin staining was also apparent in areas of low-grade dysplasia within mucinous cysts that contained both low- and high-grade dysplasia. Cytoplasmic cathepsin E was detected in all 14 mucinous cysts examined; however, staining did not show a dependence on the degree of dysplasia (FIGS. 3E-FIG. 3H). No gastricsin or cathepsin E staining was evident in the neighboring normal ductal epithelium or stromal tissue. In addition, neither protease was detected in either of the two nonmucinous SCAs examined.

Expression of gastricsin and cathepsin E was also examined in an IPMN genetic mouse model. Ptf1a-Cre; LSL-Kras$^{G12D}$; Brg1$^{f/f}$ mice develop cystic lesions of the pancreas that closely resemble human IPMNs (44). Consistent with the above results, cytoplasmic gastricsin and cathepsin E staining was observed in the epithelial cells surrounding the cystic lesion (FIG. 9A-FIG. 9B). Once again, there was no staining in normal pancreatic tissue.

Development of a Gastricsin Selective Fluorescent Substrate.

The MSP-MS assay is ideal for discovering global differences in protease activity, but is not readily amenable for use as a diagnostic tool. Therefore, sensitive and selective fluorescent substrates were identified that could be used in a standard microplate format to distinguish mucinous from nonmucinous cysts.

Figure 4A:
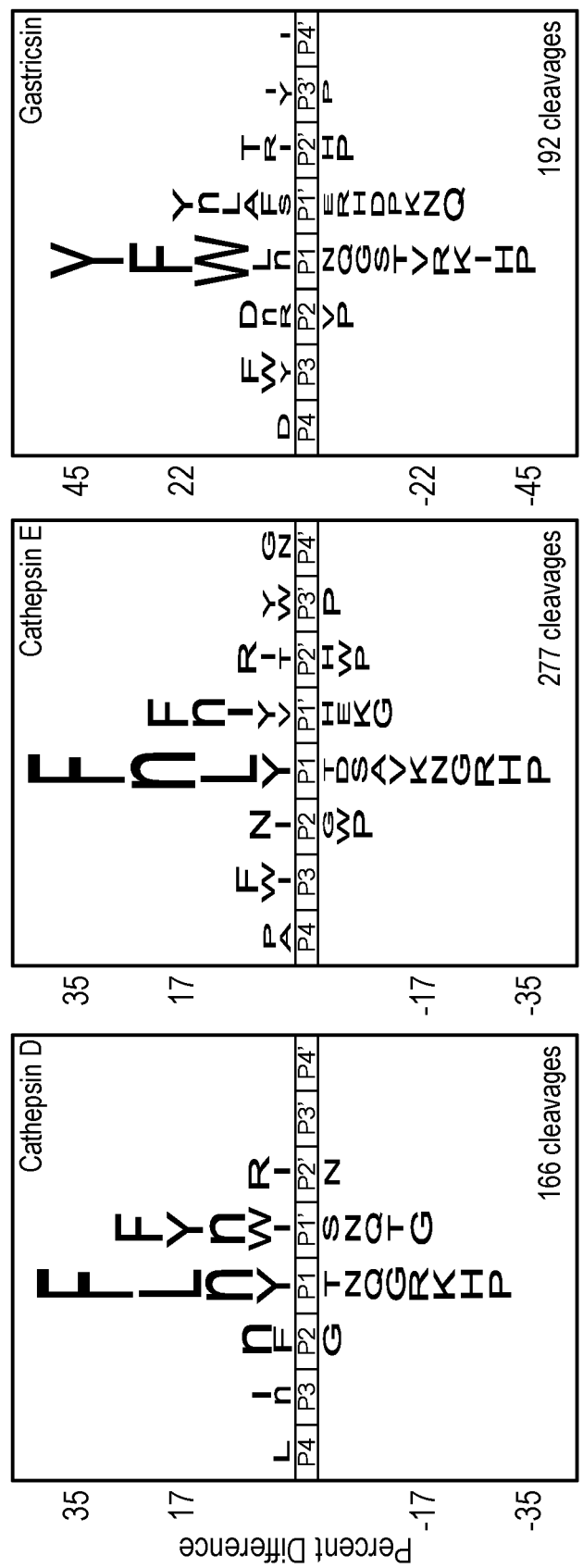

A gastricsin selective substrate was designed, as a cathepsin E selective substrate has been previously reported (45). Substrate specificity of recombinant cathepsin E and gastricsin was first analyzed using the MSP-MS assay (FIG. 4A). Recombinant cathepsin D was also profiled to ensure that the synthesized substrates are not cleaved by this protease, as it was detected in cyst fluid samples by shotgun proteomics analysis (FIG. 2B). Cathepsins E and D showed highly similar substrate specificity with a Pearson correlation coefficient of 0.81 and both proteases displayed a clear preference for hydrophobic residues in the P1 and P1' positions. Gastricsin also preferred hydrophobic residues in the P1 and P1' positions. However, direct comparison of the amino acid enrichment profiles revealed that gastricsin also has distinct cleavage preferences (FIG. 4B). Most notably, gastricsin shows a significantly stronger preference for tyrosine and tryptophan in the P1 position. Gastricsin also slightly favored small amino acids, such as glycine, serine, and alanine, in the P1' position.

Using the MSP-MS assay, 75 peptides were identified that were cleaved by gastricsin and not by cathepsins D or E (FIG. 4C). The specificity information from FIG. 4A-B was used to select a single peptide substrate expected to be highly selective for gastricsin. In particular, a peptide was chosen that was cleaved by gastricsin with a tryptophan and alanine in the P1 and P1' positions, respectively. An internally quenched, fluorescent substrate incorporating the P4 to P4' amino acids was synthesized from this peptide. This substrate was found to be greater than 120-fold selective for gastricsin over both cathepsins D and E (FIG. 4D) and is cleaved with a kcat/Km of $4.8 \times 10^5$ $M^{-1}/s^{-1}$ (FIG. 10). The previously reported cathepsin E selective substrate was also synthesized, and it was confirmed that it is more than 100-fold selective for cathepsin E over both cathepsin D and gastricsin (FIG. 4C) (45). Lastly, these substrates were used to monitor cathepsin E and gastricsin protease activity in cyst fluid. Indeed, both substrates were cleaved in fluid from a mucinous cyst and this activity was fully inhibited by pre-incubation with pepstatin (FIG. 11).

Gastricsin and Cathepsin E Activity Differentiate Mucinous from Nonmucinous cysts.

Next, the gastricsin and cathepsin E fluorescent substrates were used to assess relative protease activities in cyst fluid samples, in order to determine if these activities could be used to differentiate mucinous from nonmucinous cysts. The 23 cyst fluid samples that were previously profiled using the MSP-MS assay were analyzed. Cleavage of both the gastricsin and cathepsin E substrate was significantly higher in mucinous relative to nonmucinous cysts (FIG. 12A-FIG. 12B). This prompted an investigation to assess cathepsin E and gastricsin activity in a validation cohort comprised of an additional 87 cyst fluid samples. Again, mucinous cysts displayed significantly increased levels of gastricsin and cathepsin E activity (FIG. 12A-FIG. 12B). There were no significant differences in activity between the two patient cohorts. Analysis of all 110 patient samples revealed that gastricsin activity was on average increased more than 6-fold in mucinous cysts, while cathepsin E activity was increased only 2-fold (FIG. 5A-FIG. 5B). The ROC curve for gastricsin activity exhibited an area under the curve (AUC) of 0.979 for distinguishing mucinous cysts (FIG. 5C). At the optimal cutoff of a 1.23-fold change in fluorescence, gastricsin activity demonstrated a specificity of 100% and a sensitivity of 93%. Cathepsin E activity had an AUC of 0.828 and, using this same optimal cutoff, displayed 92% specificity and 70% sensitivity for differentiating mucinous from nonmucinous cysts. Gastricsin and cathepsin E activity did not show a dependence on the type of mucinous cyst or the degree of dysplasia within a mucinous cyst (FIG. 13A-FIG. 13D). Considering that gastricsin expression was only observed in regions of low-grade dysplasia (FIG. 3), it was surprising to observe that gastricsin activity was also not associated with the degree of dysplasia. This is likely because highly dysplastic and invasive mucinous lesions also often contain regions of low-grade dysplasia. Gastricsin and cathepsin E activity was examined for correlation with features from the revised Sendai criteria, which is a widely applied consensus guidelines for the management of mucinous cysts (8). Neither gastricsin nor cathepsin E activity showed significant differences in relation to the Sendai features assessed (Table 3).

TABLE 3

Diagnostic performance of individial and combination markers in cyst fluid samples.

| Markers | AUC (95% CI) | Sensitivity (%) (95% CI) | Sensitivity (%) (95% CI) |
|---|---|---|---|
| Gastricsin + Cathepsin E + CEA | 0.998 (0.995-1) | 98.2 (90.3-100) | 100 (89.7-100) |
| Gastricsin + CEA | 0.998 (0.995-1) | 98.2 (90.3-100) | 100 (89.7-100) |
| Gastricsin + Cathepsin E | 0.987 (0.971-1) | 94.4 (0.9713-1) | 100 (91.0-100) |
| Cathepsin E + CEA | 0.909 (0.845-0.973) | 83.6 (71.2-92.2) | 94.1 (80.3-99.3) |
| Gastricsin | 0.979 (0.952-1) | 93.0 (84.3-97.7) | 100 (91.0-100) |
| Cathepsin E | 0.828 (0.75-0.907) | 70.4 (58.4-80.7) | 92.3 (79.1-98.4) |
| CEA | 0.865 (0.792-0.938) | 74.5 (61.5-85.3) | 91.2 (76.3-98.14) |

CEA levels were independently measured for 89 of the cyst fluid samples, and abundance between mucinous (n=55) and nonmucinous cysts (n=34) was compared. As expected, CEA was significantly elevated in the mucinous cysts (FIG. 14). The CEA ROC curve exhibited an AUC of 0.865 for distinguishing mucinous cysts from nonmucinous cysts (FIG. 5C). CEA-based classification underperformed gastricsin activity, but was comparable to cathepsin E activity-based classification. For CEA, a cutoff level of 192 ng/mL is the commonly used clinical standard for differentiating mucinous from nonmucinous cysts (46). At this cutoff, CEA demonstrated a specificity of 94% and a sensitivity of 65%, which is consistent with what has been previously reported. All 19 of the mucinous cyst fluid samples with CEA levels below the standard cutoff of 192 ng/mL were correctly classified by gastricsin activity. Additionally, the two non-mucinous cysts with CEA levels above 192 ng/mL were also correctly classified by gastricsin activity.

Combined analysis of CEA with gastricsin and cathepsin E activity was assessed to see whether it could better differentiate mucinous from nonmucinous cysts. Gastricsin activity with CEA evaluation resulted in a classifier with an AUC of 0.998 (FIG. 5C), exhibiting a specificity of 100% and sensitivity of 98%. Inclusion of all three markers did not lead to improved differentiation of mucinous from nonmucinous cysts.

Example 3: Discussion

Although pancreatic cysts are being detected at an increasing rate, available diagnostic tests do not accurately discriminate between cyst types. Mucinous cysts have malignant potential and may require resection, while nonmucinous cysts are considered benign and require no further evaluation if these lesions are asymptomatic. Increasing the level of certainty in this distinction would spare some patients unnecessary surgical resections and reduce the need for ongoing surveillance for many more individuals. In this study, an unbiased and global substrate-based profiling strategy coupled with proteomics was used to identify distinguish protease activities in cyst fluid samples. Using this approach, gastricsin and cathepsin E activities were found to be promising markers for differentiating benign nonmucinous cysts from potentially malignant mucinous cysts. Selective fluorescent substrates both confirmed induction of these proteases in mucinous cysts and enabled sensitive and specific differentiation of these lesions in 110 patient samples.

To date, CEA remains the most widely used clinical biomarker for differentiating mucinous from nonmucinous cysts. However, the performance of this marker is generally considered suboptimal. Indeed, CEA analysis was only 76% accurate in this study at the standard cutoff of 192/mL. Gastricsin activity was 95% accurate, and correctly classified all 21 cysts that were misclassified by CEA, clearly demonstrating the clinical utility of this marker. Furthermore, classification accuracy was improved to 99% by combining CEA with gastricsin activity analysis.

Preoperatively determining the degree of dysplasia within a mucinous cyst is another major challenge for ensuring appropriate clinical intervention. However, the protease activity markers identified in this study do not differentiate between mucinous cysts with low- or high-grade dysplasia. Although this is a limitation of our markers, correctly differentiating mucinous from nonmucinous cysts is a critical first step in deciding which cysts should undergo resection. For example, pancreatic resection of the 39 benign nonmucinous cysts included in this study could potentially have been avoided through the application of our assay. In addition, 19 mucinous cysts within our patient cohort had CEA levels below the standard cutoff of 192 ng/mL. In high-volume pancreatic centers, radiographic and clinical features allowed experienced clinicians to correctly identify these cysts as mucinous. However, medical centers without dedicated cyst specialists may be inclined to misclassify these samples as nonmucinous and would greatly benefit from this simple and accurate diagnostic assay.

Previous gene expression profiling studies of IPMNs and MCNs demonstrated overexpression of gastricsin and cathepsin E mRNA (29-31). However, the protein levels and activity of these aspartyl proteases has not been previously investigated within these lesions. Protease activity is particularly well suited to the development of a rapid and simple diagnostic test for differentiating cysts. Activity-based detection is highly sensitive because of catalytic signal amplification. Indeed, the assays described in this study use less than 5 µL of cyst fluid, whereas CEA tests often require at least 500 µL. Furthermore, unlike immuno-assays, protease activity assays do not require the costly development of high-quality antibody reagents. Spectrophotometric protease activity assays can be readily adapted to the standard plate readers present in clinical laboratories, and there are already several examples of such assays in common clinical use for other indications (47,48).

The observation that gastricsin expression within mucinous cysts was primarily associated with areas of low-grade dysplasia and was absent in high-grade dysplasia was of interest, although only four cysts containing regions of high-grade dysplasia were assessed. Previous work demonstrated that gastricsin and other foregut markers are over-expressed in other pancreatic cancer precursor lesions, reflecting a cellular dedifferentiation step prior to malignant transformation (49). Gastricsin overexpression within IPMNs and MCNs might be reflective of a similar process. In support of this hypothesis, recent work using the same IPMN genetic mouse model examined in this study showed that cellular dedifferentiation is a critical step in the development of IPMNs (44,50). Dedifferentiation within this genetic mouse model is transient and occurs prior to the development of invasive cancer, which may explain why gastricsin expression is associated with regions of low-grade dysplasia. In contrast to gastricsin, an association between cathepsin E expression and the degree of dysplasia present within a mucinous cyst was not observed. This suggests that different processes control the expression of these two proteases and that cathepsin E levels are less reflective of cellular identity. Additional studies using the recently developed genetic mouse models of mucinous cysts are needed to characterize how the expression of these proteases is regulated and what roles—if any—gastricsin and cathepsin E are playing in neoplastic transformation (44).

In summary, these results demonstrate that gastricsin and cathepsin E activity are sensitive and specific markers for differentiating mucinous from nonmucinous pancreatic cystic lesions. In particular, gastricsin activity is a promising candidate for the development of a simple, diagnostic test with superior performance to CEA. This could provide clinical stratification to properly manage the growing problem of pancreatic cysts.

Example 4: Alternative Method

As an alternative to the methods presented in Example 1, nanoplasmonic resonator (NPR)-enhanced Raman spectroscopy may be performed to quantify the activity of aspartyl proteases. This method is further detailed in Sun et al. (2010), the contents of which are incorporated herein in its entirety.

The NPR will be patterned on quartz substrates by electron beam lithography (EBL). A 30 nm thick indium-tin-oxide (ITO) under-layer will be sputtered on the substrate to prevent charging effects during the EBL process. A 100 nm thick polymethylmethacrylate (PMMA) film spin-coated on the ITO-quartz glass is used as a positive photo-resist. After exposure, the patterns are developed using a 1:3 ratio of a MIBK and IPA mixture followed by multilayer deposition of metal and dielectric materials using electron beam evaporation (Mark 40, CHA) and standard lift-off procedures. Three layered Ag/SiO2/Ag NPR arrays are fabricated with each silver and SiO2 layer thickness equal to 25 and 5 nm, respectively. The geometry of the fabricated NPR is examined by atomic force microscopy, and the total thickness of the NPR confirmed to be 55 nm.

The optical properties of the NPR are characterized by illuminating the NPRs with collimated light delivered by a multimode optical fiber from a 150 W xenon lamp (Thermo Oriel) and collecting the extinction spectra using a grating spectrometer (Triax 550, Jobin Yvon) with a matched liquid nitrogen cooled CCD detector (CCD-3500, Jobin Yvon). For the SERS experiments, Raman spectra are measured using a modified inverted microscope (Axiovert 200, Zeiss) with a 50× objective in a backscattering configuration. Baseline subtraction is applied to remove the fluorescence background of the measured spectra. The spectra are then smoothed in Mat-lab using the Savitsky-Golay method with a second-order polynomial and window size of 9. To correct the possible influence due to the fluctuation of illumination intensity, frequency dependence of Raman scattering, and the variation of initial packing density of the reported molecules, the change in SERS intensity is normalized to the average intensity before protease addition. The normalized SERS intensity change is defined as:

$$\Delta I)[I_t - I_0]/I_0$$

where $I_0$ is the average SERS intensity before the addition of the protease and $I_t$ is the SERS intensity measured at the given time t.

The peptide attaches to the NPR via the thiol group on cysteine. The aspartyl protease substrate peptides are mixed with octanethiol at a 1:3 ratio and at a concentration of 50 M. Octanethiol, with a SAM chain length of 1-2 nm, is used as packing material to manage the distance among the aspartyl protease substrate peptides and help to erect the aspartyl protease substrate peptide for optimal spatial presentation. Thus, the octanethiol SAM improves access for the protease to bind to the peptides. The peptide solution is incubated with the NPR substrate for 24 hours to ensure a well-ordered self-assembled mono-layer on the NPR metallic surface. During incubation, the sample is kept at 20° C. Before incubation with the aspartyl protease enzyme, the sample is washed repeatedly with deionized water to ensure that all of the unattached peptides are removed. Upon washing, the sample is incubated with a sample in a Tris-HCl, pH 8.0, 100 mM NaCl, and 0.1 mM EDTA buffer. Incubation is performed by placing a 100 L drop of the sample on the NPR array. SERS measurements are performed directly after incubation at 1 min intervals.

Cell lines are maintained in RPMI-1640 with 10% FBS and 1× Pen/Strep, at 37° C. with 5% C02; $10 \times 10^6$ cells are cultured overnight in 10 mL of fresh media. Media from both cultures is collected, and aspartyl protease activity is measured by fluorescent methods as described before and calibrated against control (Calbiochem, San Diego, Calif.). Briefly, the aspartyl protease-binding peptides and derivatives with a spacer are chemically synthesized and used to prepare an affinity column, which is used to fractionate aspartyl protease.

Proteolytically active aspartyl proteases are purified to homogeneity by column chromatography, eliminating all known aspartyl protease complexes and retaining its protease fraction. Cleavage of the substrate peptide immobilized on the NPR nanosensor is performed in a buffer of 50 mM Tris-HCl, pH 8.0, 100 mM NaCl, and 0.1 mM EDTA, and the reaction is monitored in real-time in 37° C. Protease inhibitors (to prevent aspartyl protease and granzyme B degradation) are added to the reaction mixture following the manufacturer's instructions, so that the final reaction solution contains 5 M AEBSF, 4.2 nM Aproti-nin, 200 nM Elastatinal, and 10 nM GGACK. The concentration of proteolytically active aspartyl protease in the aspartyl protease reagent is prepared with a wide range of concentration from 6 pM to 6 nM.

Example 5: Alternative Method

Recently, Kokame et al. (2005) and Hovinga et al. (2006), the contents of which are incorporated herein in their entirety, described a new fluorescence resonance energy transfer assay using a truncated, synthetic 73-amino-acid VWF peptide as a substrate for the determination of ADAMTS-13 activity (FRETS-VWF73 assay). This assay may be adapted for the measurement of aspartyl protease activity. Briefly, 100 μL of each diluted standard or patient sample is incubated at 37° C. in a 96-well white plate (NUNC, Roskilde, Denmark). After 10 min, 100 μmol $L^{-1}$ of 4 μmol $L^{-1}$ FRETS-VWF73 peptide substrate dissolved in assay buffer is added to each well and evolution of fluorescence recorded at 37° C. in a TECAN Spectrafluor microplate reader (Tecan, Zuirich, Switzerland) equipped with a 340 nm excitation filter (band width 35 nm) and a 450 nm emission filter (band width 25 nm). Fluorescence is measured every 5 min and the reaction rate is calculated by linear regression analysis of fluorescence over time from 5 to 60 min.

Example 6: Analysis of Gastricsin and Cathepsin E Concentration by Enzyme Linked Immunosorbent Assay (ELISA)

Pancreatic cyst fluid is diluted into phosphate buffered saline (PBS) and each sample is added to a 96-well microtiter plate for 2 hours at room temperature. Unbound protein is washed away and wells are blocked with PBS containing 5% BSA for 2 hours at room temperature. Wells are then incubated with either rabbit anti-gastricsin antibody (1:500; Abcam, ab104595) or rabbit anti-cathepsin E antibody (1:1, 000; Abcam, ab49800) for 1 hour at room temperature. Following a wash step, horseradish peroxidase (HRP)-conjugated secondary antibody is applied for 1 hour at room temperature. Wells are washed and peroxidase substrate is then added to determine protein concentration through absorbance reading at 450 nM on a microplate reader.

Example 7: Parallel Reaction Monitoring (PRM) Assay Development

To develop PRM assays, we initially performed shotgun proteomic analysis of recombinant gastricsin and cathepsin E. Briefly, 10 ng of both recombinant proteases was denatured, reduced, alkylated, and digested with 100 ng of trypsin for 24 hours. Following trypsinization, the sample was desalted using a C18 tip (Rainin), dried, and resuspended in 0.1% formic acid. The sample was then injected onto an Orbitrap Fusion Lumos Mass Spectrometer (Thermo) coupled to an Ultra Performance Liquid Chromatography (UPLC) System (Waters) for peptide separation by reverse-phase liquid chromatography (RPLC). A 240 minute linear gradient from 2-30% acetonitrile was used for peptide separation with a flow rate of 300 nL/min. Survey scans were recorded over a 350-1800 m/z range and the 10 most intense precursor ions from each survey scan were fragmented by high-energy collision dissociation (HCD).

Peak lists were generated from MS/MS data in-house software called PAVA and searched in Protein Prospector v. 5.10.0. Peak lists were searched against all human protein sequences in the SwissProt database (downloaded Nov. 1, 2017). This database was concatenated with a fully randomized set of entries to estimate the false discovery rate (FDR). For database searches, peptides sequences were matched to tryptic peptides with up to two missed cleavages. Carbamidomethylation of cysteine residues was used as a constant modification and variable modifications included oxidation of methionine, N-terminal pyroglutamate from glutamine, N-terminal acetylation, and loss of N-terminal methionine. The mass accuracy tolerance was set to 20 ppm for precursor ions and 30 ppm for fragment ions. An FDR of less than 1% was used for all searches. Reported proteins were identified by at least 2 unique peptides.

From the shotgun proteomic results, we selected two of the identified peptides from both gastricsin (SYYSVYDLGNNR (SEQ ID NO: 54), GLLGEFLR (SEQ ID NO: 55)) and cathepsin E (QFYSVFDR (SEQ ID NO: 56), SQLSEFWK (SEQ ID NO: 57)) for inclusion in PRM assays. These peptides were prioritized as they are from the mature forms of the proteases and are also present in SRMAtlas (Kusebauch, 2016). The charge +2 forms of the gastricsin and cathepsin E precursor peptides were added to our inclusion list.

For PRM assays, 5 μg of cyst fluid protein was prepared as described above for the recombinant proteases. The UPLC System was also operated using the same parameters. The MS acquisition method consisted of a full MS1 scan event followed by 4 unscheduled targeted MS/MS scans for the peptides from gastricsin and cathepsin E. A 1 Da mass window was used for precursor ion isolation. The MS1 scan was performed at a resolving power of 70,000 while the MS/MS scans were performed at a resolving power of 17,500 (both at 200 m/z).

Relative quantitation of gastricsin and cathepsin E peptides was performed using the Skyline software package. Quantitation was based on the area under the curve of the 8 most intense transitions for each peptide. To correct for potential differences in protein loading between runs, peak areas were normalized by the median peak area of all fragmented ions from shotgun proteomic analysis carried out using the same sample. The average area under the curve of the two peptides from each protease was then used to estimate the protein abundance in a given cyst fluid sample.

Example 8: Colorimetric Assay for Analysis of Gastricsin and Cathepsin E Activity The proteolytic activity of gastricsin was previously measured using a colorimetric assay, where normalized optical density values are used as a measure of proteolysis (54). This assay followed the procedure of Anson and Mirsky, which briefly uses a mixture of bovine hemoglobin and enzyme in a sodium citrate buffer; at the end of a short incubation time the reaction is stopped with trichloracetic acid and the absorbance at 280 nm is determined by spectrophotometry. This assay suffers from lack of sequence specificity for gastricsin, and therefore it can only be used with a purified enzyme preparation.

In order to develop a colorimetric assay that would be specific to test the activity of gastriscin in a complex biological mixture such as cyst fluid, an alternative would be to develop a gastricsin-specific substrate with an acetylated N-terminus; following proteolytic cleavage in the presence of gastricsin, newly formed amino termini (which are non-acetylated) could be labeled with ninhydrin hydrate (55), which reacts with amino groups producing the colored ninhydrin chromophore called Ruhemann's purple, with known stechiometry and an absorption spectrum dependent on the solvent used in the reaction ($\lambda_{max}$≈570 nm). Specifically, 1 nmol of purified peptide is dissolved in 12 μL of 0.1% acetic acid (pH 3.3), followed by addition of 5 μL of 0.5 M acetic anhydride in anhydrous tetrahydrofuran (THF). The solution is incubated on ice for 5 min, and the resulting peptides are dried using a SpeedVac and resuspended in DMSO at the appropriate concentration. Peptides (10 μmol/L) are incubated with cyst fluid (1:20 dilution of stock sample) in acetate buffer containing 0.01% Tween (pH 2) for 1 hour at room temperature. A control reaction is set up in parallel and includes cyst fluid without peptide substrates. At the end of the incubation, cleaved substrates are quantified using the ninhydrin assay: a color reagent solution of 2% (w/v) ninhydrin and 0.3% (w/v) hydrindantin is prepared in 75% DMSO and 25% 4M sodium acetate buffer (pH 5.5). 100 μl of sample is incubated with 75 μl of the color reagent solution and incubated at 80° C. for 30 min, then finally mixed with 100 μl of 50% ethanol, cooled to room temperature and the absorbance is measured at 570 nm. Each sample is normalized against its own non-substrate control to subtract background signal. The absorbance values can be either used as is, or converted to active gastricsin concentration using a standard curve with serial dilution of recombinant gastricsin incubated with the same peptide substrates. A further alternative is direct detection of the cleaved synthetic reporter peptides using targeted LC-MS/MS.

REFERENCES

1. Moris M, Bridges M D, Pooley R A, Raimondo M, Woodward T A. Association Between Advances in High-Resolution CrossSection Imaging Technologies and Increase in Prevalence of Pancreatic Cysts From 2005 to 2014. Clin Gastroenterol Hepatol. 2016; 14:585-93.
2. Lee K S, Sekhar A, Rofsky N M, Pedrosa I. Prevalence of incidental pancreatic cysts in the adult population on M R imaging. Am J Gastroenterol. 2010; 105:2079-84.
3. Laffan T A, Horton K M, Klein A P, Berlanstein B, Siegelman S S, Kawamoto S, et al. Prevalence of unsuspected pancreatic cysts on MDCT. Am J Roentgenol. 2008; 191:802-7.
4. Volkan Adsay N. Cystic lesions of the pancreas. Mod Pathol. 2007; 20:71-93.
5. Matthaei H, Schulick R D, Hruban R H, Maitra A. Cystic precursors to invasive pancreatic cancer. Nat Rev Gastroenterol Hepatol. Nature Publishing Group; 2011; 8:141-50.
6. Crippa S, Del Castillo C F, Salvia R, Finkelstein D, Bassi C, Dominguez I, et al. Mucin-Producing Neoplasms of the Pancreas: An Analysis of Distinguishing Clinical and Epidemiologic Characteristics. Clin Gastroenterol Hepatol. 2011; 8:213-9.
7. Jang K-T, Park S M, Basturk O, Bagci P, Bandyopadhyay S, Stelow E B, et al. Clinicopathologic characteristics of 29 invasive carcinomas arising in 178 pancreatic mucinous cystic neoplasms with ovarian-type stroma: implications for management and prognosis. Am J Surg Pathol. 2015; 39:179-87.
8. Tanaka M, Fernindez-del Castillo C, Adsay V, Chari S, Falconi M, Jang J-Y, et al. International consensus guidelines 2012 for the management of IPMN and MCN of the pancreas. Pancreatology. Elsevier; 2012; 12:183-97.
9. Correa-Gallego C, Ferrone C R, Thayer S P, Wargo J A, Warshaw A L, Fernandez-Del Castillo C. Incidental pancreatic cysts: Do we really know what we are watching?Pancreatology. 2010; 10:144-50.
10. Parra-herran C E, Garcia M T, Herrera L, Bejarano P A. Cystic Lesions of the Pancreas: Clinical and Pathologic Review of Cases in a Five Year Period. J Pancreas. 2010; 11:358-64.
11. Quan S Y, Visser B C, Poultsides G A, Norton J A, Chen A M, Banerjee S, et al. Predictive Factors for Surgery Among Patients with Pancreatic Cysts in the Absence of High-Risk Features for Malignancy. J Gastrointest Surg. 2015; 19:1101-5.
12. Cho C S, Russ A J, Loeffler A G, Rettammel R J, Oudheusden G, Winslow E R, et al. Preoperative classification of pancreatic cystic neoplasms: the clinical significance of diagnostic inaccuracy. Ann Surg Oncol. 2013; 20:3112-9.
13. Park W G, Mascarenhas R, Palaez-Luna M, Smyrk T C, Kane D O, Ph D, et al. Diagnostic Performance Of Cyst Fluid Carcinoembryonic Antigen And Amylase In Histologically Confirmed Pancreatic Cysts. Pancreas. 2011; 40:42-5.
14. Ngamruengphong S, Bartel M J, Raimondo M. Cyst carcinoembryonic antigen in differentiating pancreatic cysts: A. Dig Liver Dis. Editrice Gastroenterologica Italiana; 2013; 45:920-6.
15. Almoguera C, Shibata D, Forrester K, Martin J, Arnheim N, Perucho M. Most Human Carcinomas of the Exocrine Contain Mutant c-K-ras Genes. Cell. 1988; 53:549-54.
16. Hezel A F, Kimmelman A C, Stanger B Z, Bardeesy N, Depinho R a. Genetics and biology of pancreatic ductal adenocarcinoma. Genes Dev. 2006; 20:1218-49.
17. Khalid A, Zahid M, Finkelstein S D, Leblanc J K. Pancreatic cyst fluid DNA analysis in evaluating pancreatic cysts: a report of the PANDA study. Gastrointest Endosc. 2009; 69:1095-102.
18. Wu J, Matthaei H, Maitra A, Dal Molin M, Wood L D, Eshleman J R, et al. Recurrent GNAS mutations define an unexpected pathway for pancreatic cyst development. Sci Transl Med. 2011; 3:92ra66.
19. Hata H T, M. Dal Molin, M. Suenaga, J. Yu, M. Pittman, M. Weiss, M. I. Canto, C. Wolfgang, A. M. Lennon, R. H. Hruban, M. Goggins. Cyst fluid telomerase activity predicts the histologic grade of cystic neoplasms of the pancreas. Clin Cancer Res. 2016; 20:5141-41.
20. Zikos T, Pham K, Bowen R, Chen A M, Banerjee S, Friedland S, et al. Cyst Fluid Glucose is Rapidly Feasible and Accurate in Diagnosing Mucinous Pancreatic Cysts. Am J Gastroenterol. 2015; 110:909-14.
21. Yip-Schneider M T, Wu H, Dumas R P, Hancock B A. Vascular Endothelial Growth Factor, a Novel and Highly Accurate Pancreatic Fluid Biomarker for Serous Pancreatic Cysts. J Am Coll Surg. 2014; 218:608-17.
22. Cao Z, Maupin K, Curnutte B, Fallon B, Feasley C L, Brouhard E, et al. Specific glycoforms of MUC5AC and endorepellin accurately distinguish mucinous from non-mucinous pancreatic cysts. Mol Cell Proteomics. 2013; 12:2724-34.
23. Maker A V, Katabi N, Qin L, Klimstra D S, Schattner M, Brennan F, et al. Cyst fluid interleukin-1b (IL1b) levels predict the risk of carcinoma in intraductal papillary mucinous neoplasms of the pancreas. Clin Cancer Res. 2012; 17:1502-8.
24. Kessenbrock K, Plaks V, Werb Z. Matrix metalloproteinases: regulators of the tumor microenvironment. Cell. 2010; 141:52-67.
25. Sevenich L, Joyce J A. Pericellular proteolysis in cancer. Genes Dev. 2014; 2331-47.

26. Sobotic B, Vizovigek M, Vidmar R, Van Damme P, Gocheva V, Joyce J A, et al. Proteomic Identification of Cysteine Cathepsin Substrates Shed from the Surface of Cancer Cells. Mol Cell Proteomics. 2015; 14:2213-28.

27. Joyce J a, Baruch A, Chehade K, Meyer-Morse N, Giraudo E, Tsai F-Y, et al. Cathepsin cysteine proteases are effectors of invasive growth and angiogenesis during multistage tumorigenesis. Cancer Cell. 2004; 5:443-53.

28. Gocheva V, Zeng W, Ke D, Klimstra D, Reinheckel T, Peters C, et al. Distinct roles for cysteine cathepsin genes in multistage tumorigenesis. Genes Dev. 2006; 543-56.

29. Terris B, Blaveri E, Crnogorac-Jurcevic T, Jones M, Missiaglia E, Ruszniewski P, et al. Characterization of gene expression profiles in intraductal papillary-mucinous tumors of the pancreas. Am J Pathol. 2002; 160:1745-54.

30. Sato N, Fukushima N, Maitra A, Iacobuzio-Donahue C a, van Heek N T, Cameron J L, et al. Gene expression profiling identifies genes associated with invasive intraductal papillary mucinous neoplasms of the pancreas. Am J Pathol. 2004; 164:903-14.

31. Fukushima N, Sato N, Prasad N, Leach S D, Hruban R H, Goggins M. Characterization of gene expression in mucinous cystic neoplasms of the pancreas using oligonucleotide microarrays. Oncogene. 2004; 23:9042-51.

32. Ke E, Patel B B, Liu T, Li X, Haluszka O, Hoffman J P, et al. Proteomic Analyses of Pancreatic Cyst Fluids. Pancreas. 2009; 38:1-21.

33. Raty S, Sand J, Laukkarinen J, Vasama K, Bassi C, Salvia R, et al. Cyst fluid SPINK1 may help to differentiate benign and potentially malignant cystic pancreatic lesions. Pancreatology; 2013; 13:530-3.

34. O'Donoghue A J, Eroy-reveles A A, Knudsen G M, Ingram J, Zhou M, Statnekov J B, et al. Global identification of peptidase specificity by multiplex substrate profiling. Nat Methods. 2012; 9:1095-100.

35. Chalkley R J, Baker P R, Medzihradszky K F, Lynn A J, Burlingame A L. In-depth Analysis of Tandem Mass Spectrometry Data from Disparate Instrument Types. Mol Cell Proteomics. 2008; 2386-98.

36. Schilling B, Rardin M J, MacLean B X, Zawadzka a. M, Frewen B E, Cusack M P, et al. Platform-Independent And Label-Free Quantitation Of Proteomic Data Using M S 1 Extracted Ion Chromatograms In Skyline: Application To Protein Acetylation And Phosphorylation. Mol Cell Proteomics. 2012; 11:202-14.

37. Colaert N, Helsens K, Martens L, Vandekerckhove J, Gevaert K. Improved visualization of protein consensus sequences by iceLogo. Nat Methods. 2009; 6:786-7.

38. Winter M B, Salcedo E C, Lohse M B, Hartooni N, Gulati M, Sanchez H, et al. Global Identification of Biofilm-Specific Proteolysis in Candida albicans. MBio. 2016; 7:1-13.

39. O'Donoghue A J, Knudsen G M, Beekman C, Perry J a., Johnson A D, DeRisi J L, et al. Destructin-1 is a collagen-degrading endopeptidase secreted by Pseudogymnoascus destructans, the causative agent of white-nose syndrome. Proc Natl Acad Sci. 2015; 112:7478-83

40. Small J L, O'Donoghue A J, Boritsch E C, Tsodikov O V, Knudsen G M, Vandal O, et al. Substrate specificity of MarP, a periplasmic protease required for resistance to acid and oxidative stress in Mycobacterium tuberculosis. J Biol Chem. 2013; 288:12489-99.

41. Impens F, Colaert N, Helsens K, Ghesquibre B, Timmerman E, De Bock P-J, et al. A quantitative proteomics design for systematic identification of protease cleavage events. Mol Cell Proteomics. 2010; 9:2327-33.

42. Donoghue A J O, Ivry S L, Chaudhury C, Hostetter D R, Hanahan D, Craik C S. Procathepsin E is highly abundant but minimally active in pancreatic ductal adenocarcinoma tumors. Biol Chem. 2016; 397:871-81.

43. Dunn B M. Structure and Mechanism of the Pepsin-Like Family of Aspartic Peptidases. Chem Rev. 2002; 102: 4431-58.

44. von Figura G, Fukuda A, Roy N, Liku M E, Morris J P, Kim G E, et al. The chromatin regulator Brg1 suppresses formation of intraductal papillary mucinous neoplasm and pancreatic ductal adenocarcinoma. Nat Cell Biol. 2014; 16:255-67.

45. Abd-Elgaliel W R, Tung C-H. Selective detection of Cathepsin E proteolytic activity. Biochim Biophys Acta. 2010; 1800:1002-8.

46. Brugge W R, Lewandrowski K, Lee-Lewandrowski E, Centeno B A, Szydlo T, Regan S, et al. Diagnosis of Pancreatic Cystic Neoplasms: A Report of the Cooperative Pancreatic Cyst Study. Gastroenterology. 2004; 126: 1330-6.

47. Kremer Hovinga J A, Mottini M, Lammle B. Measurement of ADAMTS-13 activity in plasma by the FRETS-VWF73 assay: Comparison with other assay methods. J Thromb Haemost. 2006; 4:1146-8.

48. Moll S, Ortel T L. Monitoring Warfarin Therapy in Patients with Lupus Anticoagulants. Ann Intern Med. 1997; 127:177-85.

49. Prasad N B, Biankin A V, Fukushima N, Maitra A, Dhara S, Elkahloun A G, et al. Gene Expression Profiles in Pancreatic Intraepithelial Neoplasia Reflect the Effects of Hedgehog Signaling on Pancreatic Ductal Epithelial Cells Gene Expression Profiles in Pancreatic Intraepithelial Neoplasia Reflect the Effects of Hedgehog Signaling on. Cancer Res. 2005; 1619-26.

50. Roy N, Malik S, Villanueva K E, Urano A, Lu X, Von Figura G, et al. Brg1 promotes both tumor-suppressive and oncogenic activities at distinct stages of pancreatic cancer formation. Genes Dev. 2015; 29:658-71.

51. Sun C, Su K-H, et al. Time-Resolved Single-Step Protease Activity Quantification Using Nanoplasmonic Resonator Sensors. ACS Nano. 2010; 4(2):978-984.

52. Kokame K, Nobe Y, et al. FRETS-VWF73, a first fluorogenic substrate for ADAMTS13 assay. Brit J Haem. 2005 Mar. 14; 129(1):93-100.

53. Hovinga J A K, Mottini M, Lammle B. Measurement of ADAMTS-13 activity in plasma by the FRETS-VWF73 assay: comparison with other assay methods. J Thrombo Haem. 2006 May; 4(5):1146-1148.

54. Chiang L, Sanchez-Chiang L, Mills J N, Tang J. (1967) Purification and properties of porcine gastricsin. *J Biol Chem.* 242(13):3098-102. PubMed PMID:6027790.

55. Friedman M. (2004) Applications of the ninhydrin reaction for analysis of amino acids, peptides, and proteins to agricultural and biomedical sciences. *J Agric Food Chem.* 52(3):385-406. PubMed PMID: 14759124.

The invention claimed is:

1. A method of diagnosing a subject with a mucinous cyst or a pseudocyst comprising:
   (a) detecting the presence, absence, and/or quantity of at least one aspartyl protease or functional fragment thereof in a sample; wherein detecting the presence, absence, and/or quantity of at least one aspartyl protease or functional fragment thereof comprises:
      (i) contacting the sample to at least one substrate specific for cathepsin E, gastricsin, functional fragments thereof, or combinations thereof; and
      (ii) calculating one or more scores based upon the presence, absence, or quantity of cathepsin E and/or gastricsin and/or functional fragment thereof;
   (b) diagnosing the subject with a mucinous cyst when the presence or quantity of cathepsin E and/or gastricsin and/or functional fragment thereof or combinations thereof is detected or quantified;
   wherein the step of diagnosing comprises correlating the one or more scores to the presence, absence, or quantity of cathepsin E and/or gastricsin and/or functional fragment thereof, such that, if the amount of cathepsin E and/or gastricsin and/or functional fragment thereof is greater than the quantity of cathepsin E and/or gastricsin and/or functional fragment thereof in a control sample; or, if the amount of cathepsin E and/or gastricsin and/or functional fragment thereof is substantially equal to or greater than the quantity of cathepsin E and/or gastricsin and/or functional fragment thereof in a sample taken from a subject known to have a mucinous cyst, then the subject is diagnosed as having a mucinous cyst.

2. The method of claim 1, wherein the step of detecting further comprises measuring the quantity of the at least one aspartyl protease or functional fragment thereof in the sample by one or a combination of: digitally imaging the sample, exposing the sample to a known amount of labeled antibody specific for an epitope of cathepsin E and/or gastricsin, or a functional fragment thereof; exposing the sample to a library of substrates for cathepsin E and/or gastricsin, or a functional fragment thereof; exposing the sample to at least one labeled antibody specific for an epitope of cathepsin E and/or gastricsin, or a functional fragment thereof; exposing the sample to chromatography; and/or exposing the sample to mass spectrometry.

3. The method of claim 1 further comprising measuring a quantity of Carcinoembryonic antigen (CEA) in the sample.

4. The method of claim 1, wherein the substrate specific for cathepsin E, gastricsin, or functional fragments thereof is one or a plurality of substrates chosen from a substrate having an amino acid sequence with formula: DEGWALQH (SEQ ID NO: 1), VGKWSYRM (SEQ ID NO: 2), NMKWTRVL (SEQ ID NO: 3), PWTWYGVK (SEQ ID NO: 4), FGIFYLNG (SEQ ID NO: 5), HMIALYWG (SEQ ID NO: 6), IKILMFYW (SEQ ID NO: 7), GLYFRYE (SEQ ID NO: 8), AGFSLPA (SEQ ID NO: 9), or an analog that is at least 70%, 80%, 87%, 90%, 95%, 96%, 97%, 98%, or 99% homologous to the amino acid sequences SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

5. The method of claim 4, wherein the substrate specific for cathepsin E, gastricsin, or functional fragments thereof is an amino acid comprising at least 87% homology to one or a plurality of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9.

6. The method of claim 3, further comprising calculating one or more scores based upon the quantity of CEA.

7. The method of claim 1, wherein the sample is cystic fluid.

8. The method of claim 1, wherein the step of detecting further comprises measuring the quantity of the at least one aspartyl protease or functional fragment thereof in the sample by Raman spectroscopy.

* * * * *

SEQUENCE LISTING

<160> NUMBER OF SEQ ID NOS: 58

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Asp Glu Gly Trp Ala Leu Gln His
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Val Gly Lys Trp Ser Tyr Arg Met
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Asn Met Lys Trp Thr Arg Val Leu
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Pro Trp Thr Trp Tyr Gly Val Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Phe Gly Ile Phe Tyr Leu Asn Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

His Met Ile Ala Leu Tyr Trp Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Ile Lys Ile Leu Met Phe Tyr Trp
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Gly Leu Tyr Phe Arg Tyr Glu
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Ala Gly Phe Ser Leu Pro Ala
1               5

<210> SEQ ID NO 10
<211> LENGTH: 396
<212> TYPE: PRT
<213> ORGANISM: Homo sapiens

<400> SEQUENCE: 10

Met Lys Thr Leu Leu Leu Leu Leu Val Leu Leu Glu Leu Gly Glu
1               5                   10                  15

Ala Gln Gly Ser Leu His Arg Val Pro Leu Arg Arg His Pro Ser Leu
                20                  25                  30

Lys Lys Lys Leu Arg Ala Arg Ser Gln Leu Ser Glu Phe Trp Lys Ser
            35                  40                  45

His Asn Leu Asp Met Ile Gln Phe Thr Glu Ser Cys Ser Met Asp Gln
    50                  55                  60

Ser Ala Lys Glu Pro Leu Ile Asn Tyr Leu Asp Met Glu Tyr Phe Gly
65                  70                  75                  80

Thr Ile Ser Ile Gly Ser Pro Pro Gln Asn Phe Thr Val Ile Phe Asp
                85                  90                  95

Thr Gly Ser Ser Asn Leu Trp Val Pro Ser Val Tyr Cys Thr Ser Pro
            100                 105                 110

Ala Cys Lys Thr His Ser Arg Phe Gln Pro Ser Gln Ser Ser Thr Tyr
        115                 120                 125

Ser Gln Pro Gly Gln Ser Phe Ser Ile Gln Tyr Gly Thr Gly Ser Leu
    130                 135                 140

Ser Gly Ile Ile Gly Ala Asp Gln Val Ser Val Glu Gly Leu Thr Val
145                 150                 155                 160

Val Gly Gln Gln Phe Gly Glu Ser Val Thr Glu Pro Gly Gln Thr Phe

```
                165                 170                 175
Val Asp Ala Glu Phe Asp Gly Ile Leu Gly Leu Gly Tyr Pro Ser Leu
            180                 185                 190

Ala Val Gly Gly Val Thr Pro Val Phe Asp Asn Met Met Ala Gln Asn
            195                 200                 205

Leu Val Asp Leu Pro Met Phe Ser Val Tyr Met Ser Ser Asn Pro Glu
            210                 215                 220

Gly Gly Ala Gly Ser Glu Leu Ile Phe Gly Gly Tyr Asp His Ser His
225                 230                 235                 240

Phe Ser Gly Ser Leu Asn Trp Val Pro Val Thr Lys Gln Ala Tyr Trp
                245                 250                 255

Gln Ile Ala Leu Asp Asn Ile Gln Val Gly Gly Thr Val Met Phe Cys
            260                 265                 270

Ser Glu Gly Cys Gln Ala Ile Val Asp Thr Gly Thr Ser Leu Ile Thr
            275                 280                 285

Gly Pro Ser Asp Lys Ile Lys Gln Leu Gln Asn Ala Ile Gly Ala Ala
            290                 295                 300

Pro Val Asp Gly Glu Tyr Ala Val Glu Cys Ala Asn Leu Asn Val Met
305                 310                 315                 320

Pro Asp Val Thr Phe Thr Ile Asn Gly Val Pro Tyr Thr Leu Ser Pro
                325                 330                 335

Thr Ala Tyr Thr Leu Leu Asp Phe Val Asp Gly Met Gln Phe Cys Ser
            340                 345                 350

Ser Gly Phe Gln Gly Leu Asp Ile His Pro Pro Ala Gly Pro Leu Trp
            355                 360                 365

Ile Leu Gly Asp Val Phe Ile Arg Gln Phe Tyr Ser Val Phe Asp Arg
370                 375                 380

Gly Asn Asn Arg Val Gly Leu Ala Pro Ala Val Pro
                385                 390                 395

<210> SEQ ID NO 11
<211> LENGTH: 388
<212> TYPE: PRT
<213> ORGANISM: Homo sapiens

<400> SEQUENCE: 11

Met Lys Trp Met Val Val Leu Val Cys Leu Gln Leu Leu Glu Ala
1               5                   10                  15

Ala Val Val Lys Val Pro Leu Lys Lys Phe Lys Ser Ile Arg Glu Thr
            20                  25                  30

Met Lys Glu Lys Gly Leu Leu Gly Glu Phe Leu Arg Thr His Lys Tyr
        35                  40                  45

Asp Pro Ala Trp Lys Tyr Arg Phe Gly Asp Leu Ser Val Thr Tyr Glu
    50                  55                  60

Pro Met Ala Tyr Met Asp Ala Ala Tyr Phe Gly Glu Ile Ser Ile Gly
65                  70                  75                  80

Thr Pro Pro Gln Asn Phe Leu Val Leu Phe Asp Thr Gly Ser Ser Asn
                85                  90                  95

Leu Trp Val Pro Ser Val Tyr Cys Gln Ser Gln Ala Cys Thr Ser His
            100                 105                 110

Ser Arg Phe Asn Pro Ser Glu Ser Ser Thr Tyr Ser Thr Asn Gly Gln
            115                 120                 125

Thr Phe Ser Leu Gln Tyr Gly Ser Gly Ser Leu Thr Gly Phe Phe Gly
        130                 135                 140
```

Tyr Asp Thr Leu Thr Val Gln Ser Ile Gln Val Pro Asn Gln Glu Phe
145                 150                 155                 160

Gly Leu Ser Glu Asn Glu Pro Gly Thr Asn Phe Val Tyr Ala Gln Phe
            165                 170                 175

Asp Gly Ile Met Gly Leu Ala Tyr Pro Ala Leu Ser Val Asp Glu Ala
            180                 185                 190

Thr Thr Ala Met Gln Gly Met Val Gln Glu Gly Ala Leu Thr Ser Pro
            195                 200                 205

Val Phe Ser Val Tyr Leu Ser Asn Gln Gln Gly Ser Ser Gly Gly Ala
            210                 215                 220

Val Val Phe Gly Gly Val Asp Ser Ser Leu Tyr Thr Gly Gln Ile Tyr
225                 230                 235                 240

Trp Ala Pro Val Thr Gln Glu Leu Tyr Trp Gln Ile Gly Ile Glu Glu
                245                 250                 255

Phe Leu Ile Gly Gly Gln Ala Ser Gly Trp Cys Ser Glu Gly Cys Gln
            260                 265                 270

Ala Ile Val Asp Thr Gly Thr Ser Leu Leu Thr Val Pro Gln Gln Tyr
            275                 280                 285

Met Ser Ala Leu Leu Gln Ala Thr Gly Ala Gln Glu Asp Glu Tyr Gly
290                 295                 300

Gln Phe Leu Val Asn Cys Asn Ser Ile Gln Asn Leu Pro Ser Leu Thr
305                 310                 315                 320

Phe Ile Ile Asn Gly Val Glu Phe Pro Leu Pro Pro Ser Ser Tyr Ile
                325                 330                 335

Leu Ser Asn Asn Gly Tyr Cys Thr Val Gly Val Glu Pro Thr Tyr Leu
            340                 345                 350

Ser Ser Gln Asn Gly Gln Pro Leu Trp Ile Leu Gly Asp Val Phe Leu
            355                 360                 365

Arg Ser Tyr Tyr Ser Val Tyr Asp Leu Gly Asn Asn Arg Val Gly Phe
370                 375                 380

Ala Thr Ala Ala
385

<210> SEQ ID NO 12
<211> LENGTH: 14646
<212> TYPE: DNA
<213> ORGANISM: Homo sapiens

<400> SEQUENCE: 12
atcattcggc cctcgagactg ggctgggcag gtctgagagt tagggaaagt ccgttcccac    60
tgccctcggg gagagaagaa aggaggggggc aagggagaag ctgctggtcg gactcacaat   120
gaaaacgctc cttcttttgc tgctggtgct cctggagctg ggagaggccc aaggatccct   180
tcacaggtga gaagacgtcc ccgcactgtg ttcagctggg tagtcccatg ccctgcaact   240
cagggctgct ctggggtagg aaagctgatg gggaggtgaa gaggaggaga agctgagggc   300
ttgcgtcaat gcatggaaga gactcatcca gtgaccgcct gtgtatggcc ttaatctcca   360
gtcctcaaca agtcatcctc ctgcctccac ctccacggag gtgccttccc aagtcccagg   420
ggtcttcttg tgttgcaaaa gagcaggaac ctgcagttgt ggtttgtagc tcaaagcgcc   480
ccaggacttc cccaggggac tgaccatcac tgtccccaag agtttttctg tccctttaaa   540
tcagcccttc gtgatgttca tgtaaaactg tagaccgccc cacatctccc attttcctag   600
atctcaaaga cctcagctcc aggagggggag ccatttccac tctaagattc taagactcta   660
tagggcagag atgaggccgg gcaggctgag tggcagagag gacgctgatc ccacctgtat   720

```
cctgcgtgct gtcttgcaga tccccccctc ccaccccatc ttctctagtt ggcccctgag      780
aaaatgggac gagaatgggg ggaagaggga ggcagaagta catctcctgc ttacatgggg      840
gtttgtctcc agggtgcccc tcaggaggca tccgtccctc aagaagaagc tgcgggcacg      900
gagccagctc tctgagttct ggaaatccca taatttggac atgatccagt tcaccgagtc      960
ctgctcaatg gaccagagtg ccaaggaacc cctcatcaac tacttggatg tgaggcctcc     1020
tggggtcagg gctggggaga ggtgggagcg ggaggaaggc ccagcattag gcatggccag     1080
gtgccacatc agtagcaccg aaggccattg tggatttctt cacttggatg atgatccatg     1140
gggactgatt ccctgggtcc ccatggagtt ggctaagcag ccccccatgt acccaaatgt     1200
cagagttctc tgcagaagga aagggctggg agtgaaagca tcatcccaca ctgaaggccc     1260
ctgcttctgc tctcagctgg gcagcttact ggctgtgtac ccttaggcaa gttacttaac     1320
ctctcccagc cccagttccc tggtctgtaa acagatggt tcttcctcca ctgcctctcc      1380
tacaatgtat ttataagaat caggttagtg caagtaaaat caaatgaagt agccagaggc     1440
ttggtttgat ttcctccttc atggccattt ctctgctcct tttaccttt attttccagc       1500 gttgccactt cctaggctct gtaaactcca gtctgtatta ccccaggctc tggcccctgg     1560
gagctttccc ctggcttcct ggtgagcacc cttgtccctc ccaccaccc acaccctctt       1620 tccttctcac tcttccttgc agatggaata cttcggcact atctccattg ctccccacc       1680 acagaacttc actgtcatct cgacactgg ctcctccaac ctctgggtcc cctctgtgta      1740
ctgcactagc ccagcctgca gtaagtgggg ccaggagcac cagcagagaa tgtctggggg     1800
ctagtcctgg gaggccaagc ctggtactct ggggaagggg ggcttaggtt ccagaaactg     1860
gccatccctg ccacaccagc ttccactctc catctttgag tcagccgtgg aactgcttat     1920
agcagagata gagcaaagcc aaggaagaac taaaatgtgg ctgctgtcca agagagtaac     1980
tttcatactg atcagaatta atagaaagaa agccattgaa aagagaaatc tttgacataa     2040
tgactcactt cctttggaac acccaaagga atgtagggga agtttaattt aattggttat     2100
ttctgagcag ggaggtgagt cgggttctag tgtagatagt ctgcttgttt caaggaggct     2160
tggtagcctt atctcctggt gcacacaggt ggggctggtg gggcacaatg gcatgggtgg     2220
gtccatttgt ccagaggtaa ctcagaagtt tcagtgagga ttggaaaaga agagctacag     2280
aaagatgtct tgttcgatac aggacaagtc ccagagacag aatgtctctg gaaaccccaa     2340
ggctagagat gtccatcggt tgggagaaaa gttgggagta atttcctggg gcaattgttt     2400
atccctgagt ttcttttgaa gccaacctct gacccacaat gggtggcagg gactgtggct     2460
ggcgcctgat aaatgacact tatcttggtg tgcctcatga ggtcattgtg gacaatcagg     2520
tttgctcagg gatagctatt tggtccccag ttaggccaca tctgtagcta gagggaaatg     2580
tagttgttca ttagggaggg gcatcaccag gcttctaggg gcccccactc agtgttgaga     2640
gctgagggaa gagaccctgc cgctgtgggg ctggtggca ttagggcagg gatgcagcca      2700
gtgagccgat ggcataagca agagcagtgc acttctttcc agagacgcac agcaggttcc     2760
agccttccca gtccagcaca tacagccagc caggtcaatc tttctccatt cagtatggaa     2820
ccgggagctt gtccgggatc attggagccg accaagtctc tgtgagtgca agtccttcat     2880
tttttctctc ttggacagaa acttgggaga cttattcaga ggtcttacat ttcaaatctg     2940
cctcaggaat gggtggaaac aggggttagc actaacttct aggagaaagg gcaagcaaca     3000
ctccccacct gagatggtgg cagtgggtca gtctccacag cacgctgggc cctgggggag     3060
```

```
agcagcacag ggggactctg gcaggaagca gtgcccagtg cacaaagcct ggtggcaggg      3120
tgcacagctg gatctccagt ctctagggca ttgaggagat aaaaccacgt ctccgtcttg      3180
aaggataaag aagtccacac caggggggaga gatttggact cagtaacata aggggcaag      3240 gtctgaaatg ggagtccaat cacagaggca aggcagaagc ccagttgtcc aaaggccaag      3300
gtccaaactg aactcagtgc tgagctcatg agctgttcct caaactccct ctgacctctg      3360
accctctgac tccctctgaa gtcctatggg tcctagaact atgggaatca gacaaatgtg      3420
gggacagaga gccaggtact ttttcaggct tatagacagc aatatatgcc tgggccttgg      3480
gagaaagaga ggttgaccta ctcctggtga acgttggtcc ctggggtatt cccgaggcca      3540
gcagggcaca gccttcatca acatccctta gagtgggtgg agtaggacat attatcaact      3600
gaaagaatgc cagaagcaga aaacaccat ctatgtaaaa atatcataca gataaaacaa      3660
tgtactgtat tttctattgg aactatgtat gcgtgtgtat acacacatta catatataat      3720
atataatata taatatccat atatgaatat atgtaatata cagtatattt gtatatataa      3780
tatatatcca tctgtatata ttatatagat acaaatgtta acatattaaa gtatataata      3840
attgcataat tatatcatat aatacatgtt atatattata taattaatat aatatgtaat      3900
acattacatt aatatatgtt atataatata taatatatta tagaatataa ttgatataat      3960
gtattatatt aataatatag tatgtgttat ataatatatt aatatgttgt atgtaataat      4020
atattacata atatattatg ttaatctatt atataataga ttaacctatt atataataga      4080
ttaacataat atattacata atatgttaat ctattatata atagattaac acaatatata      4140
tgtaatgtgt atatattatg ttatatataa gattctatat atattatgac atatacatat      4200
atattatata tctaattaca tataatatat atataaaagt taaaatgact attttgaagg      4260
ctacatccct aactgatcat cacagtaacc tctgagatgc agggaaggga ctgaaattag      4320
catagaaagg ggaattcaag cctatagctt gtcacgtatc tgttggctca cctggctggt      4380
gtagggcagc agccaagccc acagcaatgt cagctgcatt gctccttccc tcagttttttc      4440 tggctccagg accaggtgtg cacttacctc taacaaatca tcagctttttg ctgcataaca      4500 tccccatcat tgaggctgga gacttgggga cagtgagaga acaatgtggg ttccagtcca      4560
ccctcaccct catgggttcc aactggccct ttttctccca cttgacatct atcttcctt      4620 tctgctgtgc aaactgtaga ctgctgctgc agcatcagga cagaaacagt atcctaaagt      4680
acactgttta actagcaccc acagttgcat ataatcaata tctatatcca catcattata      4740
gctatatcta taatctatag tacctcctaa tggttctgct tctcttatca aaccctgact      4800
gacataataa agatatgaca tgtgaaaatt tgtagatgaa gctgatgcag cccttaaagg      4860 gaccattag cctaaaatgc atgcgttgtt aatagaaatg ctaatgatca attatctaag      4920
ctcctatttc aagaaatgaa taacaagaaa atgagcaaac cgtaaacaaa caatagcaaa      4980
tcaaacccaa agaaatcaaa aggaaggaaa taataaagag tagaatggga cacaaatgaa      5040
atagagaaat cacacagtac agaaaattaa caaagccaag aatgaactct ttgcaaagag      5100
taataaaatt ggttagcctc tcacatgact aaataagaaa aagaaagaa aatacaactt      5160 aacaatgtta gaaatgagaa agagaacatt agtaaagtta tcaagaataa ttttatattg      5220
ataaatttta caattttcag aaaatcaaca aatgccttga gaaatacagc ataccaaaac      5280
tgatgcaaaa acaaaaaata gaaaatgtga atctttttaaa gatatactct gttattaaaa      5340
aatctttcca caaagaaaac tccacgaaga aaagcctcac tgataaattc tctcaacact      5400
aaaaaaaatc agtctttcac aaactcttcc agatatttga caaagtaaaa acactttata      5460
```

```
actcatttta tgaaaccagc ataactttaa taatgaaact tgaaaaggac attataacaa    5520
aagaaaatat aaaattacag accaatctct tctctcatga atatagatgc aaaagttcta    5580
aatgaaatac tagcaaataa aatcttttgg tatataaaaa gatcatacca agggtcatct    5640
ttccaggaat ttatcattta acagaataaa aggagaaaaa tcatatgacc aatatgatta    5700
tattagtagg ttaataacat tcaatatcta ttcatgactt caagaaaaac tcttagcaaa    5760
ctaggagtag aaagtaactc ccttaatctg ataaaaatga aggacttcat ctaaaagaag    5820
cccacagcaa actttatact taatggtgaa ttgtcgagag acttctccat aagatcaaga    5880
atgagacaag gacactcaat ctcaccactt ctattcaaca ttgtactgaa atcctagcc     5940 agtgcaacaa ggcaagaaaa aagaaataaa gaacattaag atggaaaagg aagaaataac    6000
tctgtcaata ttaatgtatg acaagattcc ataagtagaa aatccaaaaa tatctacaga    6060
aaggatattg ggattaatat gtgaacttag cgaagttgct ggatatgagg tcaacataaa    6120
aaaaatcatc tggggccagg cacagtggct cacgcctgta atcccagcac tttgggaggc    6180
cgaggcaggt ggatcatgag gtcaggagtt tgagaccagc ctgaccaaca tttctctact    6240
aaaaatacaa aaattagcca ggcgtggtgg cacacgcctg tagtcccagc tactcaggag    6300
gctgaggcag aagaactgct tgaacccagg aggtggaggt tgcagtgagc caagatcatg    6360
ccatggcact ccagcctgag tgacagagtg agactctgtc tcaaaaaaaa tcatttggat    6420
ttatatatac aggttatgga tccttatccc aaatgcttgg gaccggaagc cttttagatt    6480
tcaaattttt tcagattttg aaatatttgc attatactta ccagtttagt atcccaaatc    6540
tgaaaatcca taatctgtaa tgctccaatg agcattttct ttgagcctca tgttggcact    6600
caaaaagttt tggattttga agcacttcag tttcagattt tcagatttgt gatgctcaac    6660
ctgtagcaag taaacaaat ggcaaataga ttttttaatga cactatttat aatactatca    6720
aaaccatcag ctactttgat gtaaatttaa caaaaaatgt gcgagaactc tactctgata    6780
atagcaaaca ttactaaata aaagtaaaag acttgcataa aaatcacaaa cattaatgaa    6840
taaaattaaa agaagacctg tattgaaaac taaaccatgc tcatagattg aatgactctg    6900
tttcattaaa aagtcaaatt ttttcaaatt ggtctataca accaattttta ttccaatcaa    6960 aacaacagca tttttcttta gacattagca aactgattct aacatttata tggatatgta    7020
atacaccaat acaatcttgc tgaagaaaaa cactggtaaa tattaagatt tattataaag    7080
ttacagtaat gtagacgtgt ggtgttggca cagaatttaa aaaataaaca aatgtaacag    7140
aacagaaaat acaaaactat caacacagtc atctgacttg cgttgaacaa gatactgcag    7200
tatgtggagg aaatgatggt atatttatta aatagtgcca ggtcatatga atatccagat    7260
agaaaaaaat aaatcttaat tcctacctta cacattatca catttcatat aggttccaga    7320
tcgcaatgtg aaaagtaaac aataaagctt ttagaagaaa acatgagaaa atgttttcat    7380
gaccttaagg taggcaaaat tttctgaaac aagttacaaa aaaacagtgt acaataagca    7440
catgatgagt gacagaagcc agataccaaa gagttcatat gggatgattc catttatata    7500
aaatccaaaa aataggcaaa accaatatat gttattagaa gtcaggagac tggctcttct    7560
tgaggagggg cgcaatgatt ggcaggtgca tgagggcttc tgaggtttgg aatgtcctgt    7620
tttttgggaa tatagcaagc atctttgtgc tcatttagtc aaggaaagtt gggaaggaga    7680
ggcattagct tcaagacaga ggaaaatcca ggagtcaaac cctttgccag caatcccctg    7740
tgccattctc ctgttctcct gtgggctttc tcctaccagg tggaaggact aaccgtggtt    7800
```

```
ggccagcagt ttggagaaag tgtcacagag ccaggccaga cctttgtgga tgcagagttt    7860
gatggaattc tgggcctggg ataccoctcc ttggctgtgg gaggagtgac tccagtattt    7920
gacaacatga tggctcagaa cctggtggac ttgccgatgt tttctgtcta catgagcagg    7980
taaggcccat caagtctgtg aggttaaagt cagttataac tacagggaga caacacatac    8040
acttgactta gcagtcaaaa gacctggttt aggtagcttg gtccattacc agctgtgtga    8100
tcttagtcaa acatttaacc ctctctgaat attgaggaaa tgggatttgc ttcatcaagt    8160
agctgtaaaa acactttgta aactctacca cactggctta aatttaagga atctctggga    8220
ttggttcttc attgatgctg tcactaaata tcaagctcct attatatgct gattatgatg    8280
ctcacactgg ggacccagtg aaacaagaaa gacagtacct gcaggaggag gaggcagaaa    8340
aaaatgaaaa gctgacaata aaataattgc atgctgatgg atgaataaac aaaatgtggc    8400
atatccaaat aatcaaatat tattcagcct taaaaaggaa gaaaattctg agacatgcta    8460
caacatagaa gaaacttgag gacataatgc taagtgaaat aagctagtca caaaagaca    8520 aatactgtat gattccactt aggtgaggta cctagactag tcaaattcat aggcagaaag    8580
tagactgcca gttgccagag cctgggagg ggaagtgagg aattcttaaa ccgttgttga    8640
tggcctaatg ggtataaagt tccagttctg taaaatgaaa ggtctggatt ttacaacagt    8700
gtgaacatac ttaacactac tgaattgtag actcaaaaat gggtaagata gtacatttta    8760
tgtgacatat ttttacaaca attttttaaaa ttgcacattg tttttggaaa aggtcatgag    8820
gctcacctgt ttctaggcac tcttgcccgg catccttgga gggtcatctc ctcttcctcc    8880
ttacacagga aggtgatttc tgaccttgct gactttttcc agctcagacc tggcctgcgt    8940
tcacactgtt tcagcataag cccattcctc tcattcccct ctcccacatg gagggtcctg    9000
gattttccct atcaagctat gtttcctctc cagcatgaca gcactcagga ccaggcctag    9060
gaagagctgt gagtaagaga ggcaagttgt ctagacacct ctgcttcccc ttgcagaact    9120
tccttctccc gtcgcctggg aaagtgggc tgtaatggag aatatcaagg cttggcagtc    9180
agactggcct ggatttgaat cctgccactt acattgcttc atctcactga ggctcagttt    9240
cttccacgga ccactaggtt gatgtgagtt aaataagttt agacagataa aatccccact    9300
acacggcctt gcaccaaggt aatcaacaaa tgtgagttcc tttccccact ccctctgtaa    9360
aaccactgtc ctaaaattcc tacaggtatt cactcctctc cctctttacc accctgattt    9420
cagttttgta tctttctgat ccttttcctc ctcaaaatga atctgtctta ggtcctattt    9480
ctccagagtc ctgctaggtt ccagaacata atctgagaaa tcaataccaa tgaaaataag    9540
ttttcaggct ctagtaagtc atgatacatt catattagcc tctttgcctt aacataagga    9600
gtgaataaca caaaaacgcc aggcactgtc acaaccatag tggggaagat actttgggaa    9660
aaggtgtctt tgggggttgc ttcaagccac acagtgtata cccacccagg atggtcctgg    9720
ccttggttct gaatgacaga cctgctggcc ccatttccca cctccttaac cttttttatcc    9780 aagaagcaga aacacattca caaatggtca aggggagttg tttctaacct tgtgtcaaaa    9840
aggcccagac caattcactt gcagtagtca gagtcccggt ctcaaagccc agactgatgt    9900
ttctgcctac ctgtgtgctt ggcatgagac caagaagcaa agggtcctag ctgaggctca    9960
cccctagagt tttgcagtgg ccccttcctgg acagtttgtc tttctctcca tgtagtaacc    10020
cagaaggtgg tgcggggagc gagctgattt ttggaggcta cgaccactcc catttctctg    10080
ggagcctgaa ttgggtccca gtcaccaagc aagcttactg gcagattgca ctggataagt    10140
gagtattccc catgaagtag tgacagtact aggggtaaac tgaaaagagg cacaactcaa    10200
```

```
accgatttaa ctgaaaaacc actggtcact agcagaggat gccagaagct tactgtggtt    10260
ggaggtatgg aggtgctgag caagtgtgca ggaagggacc tctgtaacca gggcagcaga    10320
cacagcttcc ttccttgtac acatggcgtg cttttaactc aacatacagt caataccagt    10380
gcacagcctg ctcccctttg ttcttttaac attaacacac aaggcaaggg atgagtaaca    10440 tgggggggttg cacaggtgaa ttgggctcag atcttgtcct caaaaaactt gtacagaaga    10500
tgagatgcac ccaaaccact atcctgtaaa atggaaggtg gtcagtgctc caagagaggt    10560
gccaccaatg tggtccagca gacaggcatg accgcttcta tctgaatgct ccagtgcatc    10620
atggaggggg ttacattgaa actgagccag gaaatatata caatatctgg gcacgaagca    10680
attggggaag tgggactaca tgcctgcctc atacctagcg ccgtgctaga caatgcagga    10740
attgaaaaag tgtagttcaa gtttcaattc agctaggatt gagttcctgc aaggtaccag    10800
gcattaggaa tgcaaaaaat aaaaggcctc aatgctcact gtctattcag agtttttcaa    10860
actgtaggaa ttcacctatt tatgggtcat gacatcattt tagaagatcc tgacctgacc    10920
aggtgtggtg gctcacacct gtaatcccag gactttggga ggccgaggca ggtggatcac    10980
aaggtcaaga gattgagaca cctacatttt ttagacgaat tggaatacag tagaaaatac    11040
cagagtgcac ttcaattgca tgaatgtgtg tgtgtgtgca ctgggtcaag aagtaaacag    11100
atttcttcct atggatctca gtagaaaaca attgaggaac actcatatgg tgggtggaaa    11160
tcattgatgt gctccaggca tttgagaggc caaaaagag tgggagtttc ctaggagccg     11220
ggggagggaa ggtgggccga ccacaaccct gtcccctcag catccaggtg ggaggcactg    11280
ttatgttctg ctccgagggc tgccaggcca ttgtggacac agggacttcc ctcatcactg    11340
gcccttccga caagattaag cagctgcaaa acgccattgg ggcagccccc gtggatggag    11400
aagtgagtgc ctgcctgcgc aagggagtgg tggggacagg agagccaggc cttctcttgg    11460
gaggtggcaa ggctctaaac ggatcctccg tattgggttt tagtatgctg tggagtgtgc    11520
caaccttaac gtcatgccgg atgtcacctt caccattaac ggagtcccct ataccctcag    11580
cccaactgcc tacaccctac tggtaagaac tgtttcctta ttctgcaggc cacagggccc    11640
tccccacatg cctgccactt cccctttttca atcgcctgca ctttgcccgc ctttacccta    11700
agccccgccc cacgttgttc tgctctcatg tggcattccc tctgggaggg acacagctgc    11760
ctgtggtgga aagaccacgg ggcttgctct aatttccagt tctgccatga agcagtagtg    11820
aacttcaggc aagccattta aggaagtctt ctgatattgc catgtagggc ttttccactg    11880
acaaagttta atctcctcaa ccaccaggtc agactggagc tattactatc tcattttata    11940
ggtgagaata tcaagactca gagagtcaaa taaatggttc aagatatgag ctgtttgcag    12000
ggaggagtgg agaataagat tatatttgtt ctaacttcaa attaacattc ctcctctagc    12060
aagaaaatgt cttttgttgc agtaaattct caagtttgta gggtgaagta gaaagggaac    12120
tcccagacct tttggacacc tatgagcacc tcacaccaca gttggtctga attttcagca    12180
ttctaggtat tcggcaccac acttcaacac actaattttt ccaagagtca ctcacagcat    12240
cagggtgact gcatcagaag aggggtgcta aggtatagac tgagggcttc agccctaccc    12300
ctaagcctct attaactcct tcccaaagcc accaacagac aatccaaata aaaacaaatg    12360
tttgctttaa aacacagctt catggtaagt cccctaagct cctgccacat agggattatg    12420
gagctgccac tctgaacacc acactgagga ccagtgagac atttagactg agccctgttc    12480
atcagtccac atgccatca acaccccagc acacccacac tctcacccttc ccccacgtga   12540
```

```
gttgagtccc tgcccaggtg gaaatcactg atgtgctcca ggcgctggag agcccaaaaa    12600
agagtgggag tttcctagaa gccaggggag gggaggtgcg tggttcttc ccggtatggt    12660 gagtggttct tttagaagat cattttagaa gatcatgacc tgaccgggca tggtgactca    12720
cacctgtaat cccaggactt tgggaggccg aggcgggtgg atcacaaggt cttgtgctgg    12780
ttctttcgca gtacagtgag tggttctttc ccaccagcag atttcaatca gagccacctt    12840
gatccatcaa aactgctgta aaaattttga cttttcacgt ccttcctctc aagaagtctc    12900
cctgagccct ctgcaaattt tcccacaccc tcatcagcaa cttcacattt caaatcattg    12960
ttggaaagac cacacttgcc tggtagagca cgtctttgcc aaactaaaaa ttagattgga    13020
gaaggtgaca ctcttctctt gaacaaggaa tgcctacttg cctcatctaa aggggtcac    13080 tcaaatgttt gtttccagaa catcaacaag aaaatagcag tggatagcca ctaacacagt    13140
tctttctctc ccttaacaaa aactaagctg agcttcacta gaaactaaag aaaccagaat    13200
ttaaaccaag gtcttccggt gccaacccctt ttgctcttct agccatgcag caagggtttc    13260
ccagttgtaa aatgatggtg acaggggtag gtgggagtat ataacagatg aacagttctc    13320
aaaattgtag aacatagacc ccaggcccat aagaatggac ttgtgcagac aaacactta    13380 ttaagcaacc tagggtaggg acatatgaag caggaggaag aacccaccga ccaaaatggt    13440
ggaacccacc agctgtccaa ggccacccag tgccagccac caccaccaca caggcagcct    13500
ccaggcagta ctactacctt cttccccccgt ttgtcatttg catccttctt tccaacccac    13560
aggacttcgt ggatggaatg cagttctgca gcagtggctt tcaaggactt gacatccacc    13620
ctccagctgg gccctctgg atcctggggg atgtcttcat tcgacagttt tactcagtct    13680
ttgaccgtgg gaataaccgt gtgggactgg ccccagcagt cccctaagga ggggccttgt    13740
gtctgtgcct gcctgtctga cagaccttga atatgttagg ctggggcatt ctttacacct    13800
acaaaaagtt attttccaga gaatgtagct gtttccaggg ttgcaacttg aattaagacc    13860
aaacagaaca tgagaataca cacacacaca cacatataca cacacacaca cttcacacat    13920
acacaccact cccaccaccg tcatgatgga ggaattacgt tatacattca tattttgtat    13980 tgattttga ttatgaaaat caaaattttt cacatttgat tatgaaaatc tccaaacata    14040
tgcacaagca gagatcatgg tataataaat cccttttgcaa ctccactcag ccctgacaac    14100
ccatccacac acggccaggc ctgttatct acactgctgc ccactcctct ctccagctcc    14160
acatgctgta cctggatcat tctgaagcaa attccgagca ttacatcatt ttgtccataa    14220 atattctaa catccttaaa tatacaatcg gaattcaagc atctcccatt gtcccacaaa    14280
tgtttggctg tttttgtagt tggattgttt gtattaggat tcaagcaagg cccatatatt    14340
gcatttattt gaaatgtctg taagtctctt tccatctaca gagtttagca catttgaacg    14400
ttgctggttg aaatcccgag gtgtcatttg acatggttct ctgaacttat ctttcctata    14460
aaatggtagt tagatctgga ggtctgattt tgtggcaaaa atacttccta ggtggtgctg    14520
ggtacttctt gttgcatcct gtcaggaggc agataatgct ggtgcctctc tattggtaat    14580
gttaagactg ctgggtgggt ttggagttct tggctttaat cattcattac aaagttcagc    14640
atttta                                                               14646
```

<210> SEQ ID NO 13
<211> LENGTH: 10691
<212> TYPE: DNA
<213> ORGANISM: Homo sapiens

<400> SEQUENCE: 13

```
cttcactcca ctgcgactgc agaactcaga gctgctcttc ctctgtggcc agttggggac    60
cagcatcatg aagtggatgg tggtggtctt ggtctgcctc cagctcttgg aggcagcagt   120
ggtcaagtga gtctgggatc tggctgctgg tgcagggagc ctggatggga gcctaaagcc   180
ctgcaaaggg caactgggcc aggggacacc ctgcctgtct ctactctggg acttctgcta   240
ggggaaggga agtctccctt tgctgatgtt agacaggaca catgggtgga aggagacaca   300
gcccctgcct tcaggaaact tcctatcaaa gggaaaagca cgatcccttc ccccatctga   360
tgaggaaaga tggacctgaa acagaggtgg taagggtgac tactgcccaa gcagcccttg   420
aatggcaggt gtggattctt ctcacagaag ggagcaatcc tttttggata agggatatct   480
tatccactat cctctctaaa agttgcttta aggctgaaaa tttactggca gatgccaaaa   540
tcatctaagc agaaacacca gtaaatgtaa atctctacac ctgaggggtc aggagaaaac   600
tctggagtag atggcatggc tcacaggcca tcaggaaggc gcccagcctg ccatcctgcc   660
tgttatttct ctacccaaga gtacttcctg aggccaagag ctggctcctc tcagaaactc   720
ctatcaatat gcatatttgg tagaggtggt taattagtct tcatagctca gggtgaaggg   780
gtttagcaga gaatttctgg agaatgcaga gtccccaggg aatggggatt aagcagaatt   840
ctggagccta gagcaaggcc agagtggacc cctagagact cccaagcaat ggcagcaagc   900
aagtctggga aggagagtgc cgagggtgtg actgagccca taggatggga cagaaacggt   960
gatttataag ttccaactcc agagctgatc tgtgctccag accacccagg ccaacttccc  1020
gtggtcctgg tgtcctgaga ggagcagtga tggggcctag gccatgcgat tagcagctgg  1080
gacagaacta ggactctgtg tcctgagtcc cagctagtgc tgttgccgtt gctccatgct  1140
ctgtcacatc cagctggtgc caggtgcctg agggctgccg tagaaaggaa ctctggggtg  1200
aactttgcca tctctgaaat cttctttgtt ttttttttg aaacagaact tcgctcttgt   1260
tgcccaggct gcagtgcaat ggcgcgatct cggctcactg aaacctctgc ctcccaggtt   1320
caagcgattc tcccacctca gcctcccgag tagctaggat tacaggcatg cgccaccatg   1380
cccggctaat tttgtaattt tagtagagat gggttttcac catcttggcc agtctggtct   1440
cgaactcctg acctcaagtg atccacccgc ctcggcctcc caaagtgctg ggattacagg   1500
cgtgagctac cgtgcctggc ctgaaatctt ctgttaaaaa tgtgcatttc ctgggctggg   1560
cgcagtggct cacgcctgta atcctagcac tttaggaggc caaggcgggc ggatcatttg   1620
aggtcgggag tttgagacca gcctgaccaa catagagaaa ccctatctct actaaaaata   1680
caaaattagc tgggcatggt ggcccttgcc tgtaatccca gctactcagg aggctgaggc   1740
agaagaatag cttgaactcg ggaggtggaa gttgaggtga gccgagatca agccattgca   1800
ctccagcctg gcaacaaga gcgaaactct gtctcaaaaa aaaaaaaaa aactacatat   1860 cctgggccag gtgcggtggc tcacacctgt aatgccagca ctttgggagg cctaggcagg   1920
cgagtcacga ggtcaggaga tcaagaccag cctggccaac atagtgaaac cctgtctctg   1980
ctaaagatac aaaaaattag ccaggcatgg tgacaggcgc ctgtaattcc agctactcgg   2040
gaggctgagg caggagaatt ttctgaaccc aggaggtaga ggttgcagtg agcggagatt   2100
gtgccattgc actctagcct gggtgacaaa agtgaaactg cgtctcaaaa aaaaaaagt   2160 acatatcctg aaaagggtaa agcctaaagt ccctcttcct ttcctgggga ggaatctatg   2220
ggatatttga cagcaaaggg ccaggagat aggaggaccc ttgagatgag gtgaggagtg   2280
catgcatggt gaaatgaatg gttttctgaa tcttagagca agtgctgaga agagctttgt   2340
```

| | | | | | |
|---|---|---|---|---|---|
| aagaaagagg | ggaagaggca | aagggaggaa | gaaacacgcg | cgcgcgcaca | cacacacaca | 2400 |
| cacacagaga | gacagacaga | cagagacaga | gagcaaaagg | ctgagagaga | gaaaaagaca | 2460 |
| cacacagaca | aggggggaaca | aacagagtgg | cagggaggtt | gaagcatgca | gttaagagaa | 2520 |
| ggagagagag | aaagagagga | gtgggaagag | aggaaggagg | gagggccttg | cctcatatgc | 2580 |
| aacctttctg | tagagtgccc | ctgaagaaat | ttaagtctat | ccgtgagacc | atgaaggaga | 2640 |
| agggcttgct | gggggagttc | ctgaggaccc | acaagtatga | tcctgcttgg | aagtaccgct | 2700 |
| ttggtgacct | cagcgtgacc | tacgagccca | tggcctacat | ggatgtgagt | cctgacccttt | 2760 |
| tctggcggta | gccttctctc | tggtgtgggc | tggagggaag | gggcaggtcc | cttcactcct | 2820 |
| ctgcccatgg | aggagcctgg | ggcccctgga | tccctctgga | actaacagct | tgctccatgg | 2880 |
| cccccaggct | gcctactttg | gtgagatcag | catcgggact | ccaccccaga | acttcctggt | 2940 |
| ccttttttgac | accggctcct | ccaacttgtg | ggtgccctct | gtctactgcc | agagccaggc | 3000 |
| ctgcagtgag | tgctgggctg | gcagagagg | ggtggttggc | agggcaaggc | actgataccc | 3060 |
| tctggggagg | gccaaacttc | cagagggagc | tcaggactga | ggggagctca | gtcctgggga | 3120 |
| ggaccaggga | catgtgcagg | gccacacagc | atgcccaagc | cagaggaaag | atgctggtcc | 3180 |
| tgcagctgga | tggccccttt | gccttccctg | ccaaatatgta | tccctttgct | tatgccagcc | 3240 |
| cctaactccc | cactcccttt | tattccactc | tccccattct | gtttactctg | ggcagtgcca | 3300 |
| ttccattcca | tgtgactaat | ttccagtcca | ttccatccca | ctccatccca | ctccattcta | 3360 |
| ctccattcta | ttctgctcca | cctcagtatt | tactaagttc | tcactgagtg | tctccaagag | 3420 |
| acacaacaga | acaatatagg | atgtgggctc | cgtactatag | tggttttggg | agacaggcag | 3480 |
| tgtttgcttt | cttaaggttg | ccttggtccc | tgctgaagcc | ttggtgtttg | gtcctgata | 3540 |
| cctttggccc | aagggggtccc | ttgatgtccc | caccctatgt | tatgactggc | ttcttgatga | 3600 |
| gtgaaggtgg | ggagtacttg | gggatgccct | ggagggctgg | ggggaatgct | gggatgtggt | 3660 |
| gcaggcccat | tcacttcttc | atctgatgag | taattactca | gcactgctgt | gagccacgtg | 3720 |
| ctttgctggg | gaccagggac | tcagggctgg | gttctctgca | aacctgtcca | cagggaggcc | 3780 |
| acagtcctga | ggcatcccaa | gattctgtaa | gtcagaaggg | gctttgggga | caaggctggc | 3840 |
| cagctcccat | gggccttcca | atgccacccc | ttgacttggc | aaccaggggt | gctgaggtcc | 3900 |
| caggatgtga | gcgcagcctg | agcgagaggc | tgaggtggga | acccggcagg | cctgagagct | 3960 |
| gagcagccct | gccccagccg | gcctgactcc | ccatgccctg | actcccctgc | agccagtcac | 4020 |
| tcccgcttca | accccagcga | gtcgtccacc | tactccacca | atgggcagac | cttctccctg | 4080 |
| cagtatggca | gtggcagcct | caccggcttc | tttggctatg | acaccctgac | tgtgagtggg | 4140 |
| catgggagt | ggaggctggg | gctgtgagct | ataagctgga | ggggacagtt | agatggactc | 4200 |
| tcctgaaaca | cggtggaatg | ctagtgttct | ggtgtgcagg | acaggaaggc | aggacaagac | 4260 |
| aggtccattc | agtcactccc | ccaacactca | ctggtggcca | ccatgtgcta | ggcactgggg | 4320 |
| caccatactg | aacaagaggg | acatggtcct | ttttccttaag | aagcataagg | cctggggagc | 4380 |
| tcagagaaga | aggagacggg | tgaggaggtg | agctgtggca | gtcaaggaag | gctacgcagg | 4440 |
| agaggtggct | cctgcaacac | ctgtcaagag | gcagaggtgg | ctggctacgg | tggctcacgc | 4500 |
| ctgtaatccc | agcactttgg | aaggccaagg | cgggcagatc | atgaggtcaa | gagatagaga | 4560 |
| ccatcctggc | caacatggtg | aaaccctgtc | tctattaaaa | gtacaaaaaa | ttagctgagc | 4620 |
| gtggtggcac | gcgcctgcag | tcccagctac | tcggaggct | gaggcaggag | aatcgctaga | 4680 |
| accaggggag | cagaggttgc | tgtgagctga | gattgcgcca | ctgcattcca | gcctggtgac | 4740 |

```
agggcgagac tctgtctcaa acaagcaaac aaacaaacaa gaaaaccaaa acaaaaaaga    4800
aggggggcaga ggtgaggaag ggatgaacag aggcttgagg agtctctagg ggaacctgga    4860
ggaggtgagt ggagtcagac tggtcacctc ccctcgtttg tgtctccatt aggtccagag    4920
catccaggtc cccaaccagg agttcggctt gagtgagaat gagcctggta ccaacttcgt    4980
ctatgcgcag tttgatggca tcatgggcct ggcctaccct gctctgtccg tggatgaggc    5040
caccacagct atgcagggca tggtgcagga gggcgccctc accagcccg tcttcagcgt     5100
ctacctcagc aagtgagcaa ccagctggcc agtccccacc tcccgggatg ctccccggc     5160
cgccctggac gactgaggct cagtgctcaa tgctttgggg tttggaggca tcccagcggg    5220
catctggctc cagtcagtct tgctccaggg ccttccttcc tgggcttcct ctcgaatcct    5280
ctcccagcca cccgaccaca ccccatccct gcacctgtcc ccagtcccct ccgacttgtc    5340
tttgcattcc atggccacga tggaatgaat ctcttccaca gcagctgaac tttgccctga    5400
gttttgctgc tctgattctc agcaccccct ggacaggctt cctggtggag aagcgggtgg    5460
ggcagttcgc tcacttcctt ctgaccgaat gttttctacc tgtatccctc ttttgcatag    5520
taatgtattg cttcatctcc ttttatctat tgttctagcc tggtcctgga gtcttctggt    5580
ctaggtccac tgctgacccc tagcaggttg ttatccttgc cagtcaacac aagcatgtgc    5640
aggcatttag tgagacaggc agtgggtggg ggtgagcggc ctggggcctg cttttctttg    5700
ttcttcttca gaattaacca gcaacttgct tttgttttgt tttgttttgt ttttttgaga    5760
tggggtctca ctctgtcacc cggtctggag tgcagtggcg caatctcggc tcactgctac    5820
ttctgcctcc cggattcaag ctattttcca gcctcagcct cccaagtagc tgggattaca    5880
ggcatgcgcc actgtgttcg gctaattttt gtgttttag tagagacggg gtttcaccat     5940
gttggccagg ctggtctcaa actcctgacc tcaggtgatc caccgcctc ggccttccaa     6000
agtgttggga ttacaggtgt gagccactgc gccggcctt aggcagccac tttctagaga     6060
cagttagctt cattggacta atctggggaa tctgaagttc aaggacctca ccctgttact    6120
aatgttgcta acttcctctc cacctctgtt tatgattcct ctgcgtgtaa acagagcagc    6180
tccacccagc tccacactcc agctaccaga gaagcctctg gaacaaacat ggaatatcct    6240
tacccccttc accaagaccc tacctgtctc caatctcagc agaaaagtaa caagctgggc    6300
cggggtgggg atcccggtga catgtctacc agaggcagga agcggagggg agaggagagc    6360
agagtgtggg ctgggggtcc caaccactag gggaccccc agaagtcagc atcattcggg     6420
agcctgaggc gctgggaatt ccaaggcctg gccagaaagc cccagtctaa gggacgcatc    6480
ccagtcccca gggagcccca atctaaggga tacagcccca tcctcaggga gcccagtct     6540
gagggagaca cagactcgtc ctcagggagg cccagtctaa gggacacagc ccatcctca    6600
gggagctcca atctaaggga tacagccctg tcctcaggga gcccagtct gaagggagac     6660
tcagtgctct cctcagggag ccccgtctg gatcagggaa ggagctctgt ttccctgtgg     6720
aggtgactgc tcaggaggaa agtccttttc catggcactc cctgacttcc ccttcccttt    6780
ctctcctgca gccagcaggg ctccagcggg ggagcggttg tctttggggg tgtggatagc    6840
agcctgtaca cggggcagat ctactgggcg cctgtcaccc aggaactcta ctggcagatt    6900
ggcattgaag agtgagtctg cggtgggcc ctggggatgt ggcacttcct tggagtgggc     6960
ttccaggcca tgtcacacac acacacagtc tggcactgct ctgggatggg gcagaggacc    7020
cctgaggctt actcctacaa agccacaact gtcctctgca ggggtgacaa agcccagctc    7080
```

```
agcctggaga agagagtgga tgtggacaac atagggaggg gcaggacctg gactcccgaa    7140
cattagggac cctgcagtcc agccccatca tgggctcaca gattagaaac gaaggtgtgt    7200
tagcaactaa tttgctcaaa gtccttacaa tgaatcagtg gacctggttt tcagtgtttt    7260
tagaaacttc cttgacactt ttaaggacta ggtcccatgg catgatgcag ggaatagcc     7320 ggattgatct ttgcagggtc ctcactttcc tcaagaaagt agctgtagct ctttgtccca    7380
cagtggtggg gaaagcccgc cccagctgcc ctgaactggg ggagtcctga ggctgcctgt    7440
cttctcccca tacaggttcc tcatcggcgg ccaggcctcc ggctggtgtt ctgagggttg    7500
ccaggccatc gtggacacag gcacctctct gctcactgtg cccagcagt acatgagtgc     7560 tcttctgcag gccacagggg cccaggagga tgagtatgga caggtgtgac tggtgagggt    7620
gtctctcttc cccaggaggc tactccagag gcattcatga tttctcctgg gaacacaata    7680
gccagctggg cgccgtggct catgcctgta atcccaacac tttgggaggc caaggcaggc    7740
agatcttttg agcccaggag tttgagacca gcctgggcaa catggcgaga ctctgtctct    7800
acaagaaata caaaaattag ctgggtgcgg tggcatgcgc ctgtagttcc agctacttgg    7860
taggctgagg tgagaggatt gtttgagccc aggaggtgga ggctgcagtg agccgtgatc    7920
tcactattgc actccagcct gggtgacaaa gcaagaccct gtctcaaaaa aaaaaaaaag    7980
cctaactctt gacctccaag cctctatctg cccaaggcgc tggaggcagg gggacctggg    8040
acgactgggc ctgtgtgcag gatggggggcc tggaggcttg ttcaggcggg gccagttgct    8100
tgtgctgaag gggagaagga ggttactatt aggcaggaat tcttctgag ctgcagtcac     8160 tcagcagaaa cagaggaaat gcttgctgga ctttgggata agagcaaaat gactggaatg    8220
tggggctgag tatgtgagca accagggctg accctttatc cccacctctc tcacctccac    8280
agggccatgc tcccctgcgc ttgtctgtct tgagtccagc caagggtttg tttaattaac    8340
ccaagcccac taccactaat tttaattttg ggagaccagt ggggtactca ttatgcagat    8400
ctgtgttttt cttttttttt tgttttttgt ttttgttttt ttgagacgga gtctctctct    8460
gtcgcccagg ctggagtgca atggcgtgat cttggctcac tgcaacctcc actttcctgg    8520
gttcaagcaa ttctctggct tcagcttcct gagtagctgg gactacaggt gtatgtcacc    8580
acgcctggct aattttttttg tattttttaat agagatgagg tttcaccata ttggccaggc   8640
tggtctcgaa ctcctgacct caagtaatct gcctgccttg gcctcccaaa gtgctgggat    8700
tacagatgtg agccaccacg cccagccatc tgtgttgttt ttgtcgttgt tgttgttgtt    8760
gttattgttg ttttgagaca gagtctcact ctgtcaccca ggctggagtg cagtgacaca    8820
atctcagctc actgcaagct ccgcctcctg ggctcaagca atcctcccac ctcagcctcc    8880
tgagtagctg ggactacacg tgtgtgccat catgcccagc taattttgt attttttggtg    8940 gaggcgggt tcatcatgt cactcaggct ggtctcgaac ttctggactc aagcaatctg       9000
cctacctcgg cctcccaaag tattgggatt acaggcacga ccaccatgc ccggccagat     9060 ctgcgtgttt taaaatgcca cttgcaagct gggcatcatg gctcatgcct gtgtatgtgt    9120
gtgtgtgtgt gtgtgtgcat atatatatat gcatatatat atacatatat atatgcatat    9180
atatatgcat atatatatgc atatatatat gcatatatat atgtatatat atatgcatat    9240
atatgtatat atatatgcat atatatatgc atatatatgt atataggcac ttgcagagaa    9300
agagcagagg ttcgatcttt aatatgggaa atcgaggcaa gaggagttag gaggctctgg    9360
gatcactcca aatcacaccc attctatgag tccatgggat aatgccagca ttacctacac    9420 aggacttttcc cttggagctg cattctctag tccaaaaaca ggcttagggc ttgggcccgg   9480
```

```
agctcaggcc tgggatccag gggctgagat gatggggctg gtgggtgcta tcaggggag      9540 gatgagttaa ccagggacct attcctcttg cagtttctcg tgaactgtaa cagcattcag      9600
aatctgccca gcttgacctt catcatcaat ggtgtggagt tccctctgcc accttcctcc      9660
tatatcctca gtgtaagtcc tggtccctgc aggctgagcc accatgattg gggttgggag      9720
gaagggctgg ggagccagaa atgctgggtc tcctgccttg tgccattttc cgactccacg      9780
cttgtactca tttatcttcc ccactcattg attctaaacc cccttctctg gaacaaggct      9840
atgaaataga agattgtcat ctatgatcaa ttattattaa ttagtgggga gaggcactgg      9900
gctctttgtt gagcacttac tagggcagac cactgtgcaa agcactttgc ttcatgatcc      9960
catttaattg tcacagtatt taatgaggga gatactcatt tctgttttac aaatgaaaac     10020
ttggaggttc agagaggttg agtaactgac tcaaggcgac acagctaagg tttgaattca     10080
agttggtttg gctccaaggt ttaaccacca ggctgatctg ctccaaattg ggagcaggag     10140
ggaggtctgt gggaagagaa gtttcccatc atggggagag gagaccctgc tgaggaccac     10200
ggcagcctga atgtacctgt tccagaaatc ctcccacccg ctctgctctg gtggctcagt     10260
tggcctatga gccctcaagg cagagaccct ggctccctca gctctgcact tgtgctccca     10320
gcccagggct cagagctgag cagggcccag ctcatgtgtg gacaaatgaa tgagtgctgc     10380 cttttctttgt tgagcagaac aacggctact gcaccgtggg agtcgagccc acctacctgt     10440
cctcccagaa cggccagccc ctgtggatcc tcggggatgt cttcctcagg tcctactatt     10500
ccgtctacga cttgggcaac aacagagtag gctttgccac tgccgcctag acttgctgcc     10560
tcgacacgtg ggctcccctc ttcctcttga ccctgcaccc tcctagggca ttgtatctgt     10620
ctttccactc tggattcagc cttctttttc tggactctgg actttctcta ataataaata     10680
gttcttcttt a                                                         10691
```

<210> SEQ ID NO 14
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 14

His Val Lys Leu Phe Arg Phe Asn
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (7)..(7)
<223> OTHER INFORMATION: X is norleucine or methionine

<400> SEQUENCE: 15

Asp Gln Arg Tyr Tyr Val Xaa Asn
1               5

<210> SEQ ID NO 16
<211> LENGTH: 8
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<222> LOCATION: (1)..(1)
<223> OTHER INFORMATION: X is norleucine or methionine

<400> SEQUENCE: 16

Xaa Ala Asn Phe Leu Arg Gly Pro
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Ile Asn Asp Phe Leu Val Arg
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is norleucine or methionine
<220> FEATURE:
<221> NAME/KEY: MISC_FEATURE
<222> LOCATION: (5)..(5)
<223> OTHER INFORMATION: X is norleucine or methionine

<400> SEQUENCE: 18

Phe Xaa Ile Glu Xaa His Val Ile
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Lys Leu Asp Glu Leu Gln Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: X is norleucine or methionine
<220> FEATURE:
<221> NAME/KEY: MISC_FEATURE
<222> LOCATION: (8)..(8)
<223> OTHER INFORMATION: X is norleucine or methionine

<400> SEQUENCE: 20

His Xaa Arg Tyr Ile Asn Val Xaa
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Arg Gly Leu Tyr Phe Ile Thr His
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X is norleucine or methionine

<400> SEQUENCE: 22

Thr Phe Gln Glu Ser Xaa Leu Asp
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Asp Ile Gln Phe Ala Thr Ala Asn
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X is norleucine or methionine

<400> SEQUENCE: 24

Glu Ser Lys Tyr Phe Xaa Gln
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is norleucine or methionine

<400> SEQUENCE: 25

Tyr Phe Arg Xaa Ile Arg Trp Ala
1               5

<210> SEQ ID NO 26
```

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26

Leu Phe Thr Tyr Phe Arg Ala Trp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Ile Asn Asp Phe Leu Val Arg Thr
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Val Gly Lys Trp Ser Tyr Arg Met
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is norleucine or methionine
<220> FEATURE:
<221> NAME/KEY: MISC_FEATURE
<222> LOCATION: (8)..(8)
<223> OTHER INFORMATION: X is norleucine or methionine

<400> SEQUENCE: 29

Lys Ile Xaa Tyr Ile Arg Phe Xaa
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(7)
<223> OTHER INFORMATION: X is norleucine or methionine

<400> SEQUENCE: 30

Thr Gly His Trp Leu Xaa Xaa His
1               5

<210> SEQ ID NO 31
<211> LENGTH: 6
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: X is norleucine or methionine
<220> FEATURE:
<221> NAME/KEY: MISC_FEATURE
<222> LOCATION: (6)..(6)
<223> OTHER INFORMATION: X is norleucine or methionine

<400> SEQUENCE: 31

Asn Phe Xaa Ala Phe Xaa
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is norleucine or methionine
<220> FEATURE:
<221> NAME/KEY: MISC_FEATURE
<222> LOCATION: (8)..(8)
<223> OTHER INFORMATION: X is norleucine or methionine

<400> SEQUENCE: 32

Gly Ile Lys Xaa Trp Gln Ser Xaa
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide

<400> SEQUENCE: 33

Pro Trp Thr Trp Tyr Gly Val Lys
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is norleucine or methionine
<220> FEATURE:
<221> NAME/KEY: MISC_FEATURE
<222> LOCATION: (5)..(5)
<223> OTHER INFORMATION: X is norleucine or methionine

<400> SEQUENCE: 34

Xaa Glu Asn Tyr Xaa Val Leu Thr
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide
```

```
<400> SEQUENCE: 35

Asp Glu Gly Trp Ala Leu Gln His
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: X is norleucine or methionine

<400> SEQUENCE: 36

Tyr Ala Phe Xaa Gln Val Ala
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic peptide

<400> SEQUENCE: 37

Gly Trp Tyr Leu Ala Ile Gln Ala
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

Gly Leu Tyr Phe Arg Tyr Glu
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: X is norleucine or methionine

<400> SEQUENCE: 39

Tyr Gln Leu Leu Thr Xaa Asn
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Arg Trp His Phe Ser Glu Asn
1               5
```

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is norleucine or methionine

<400> SEQUENCE: 41

Xaa Ile Arg Trp Ala Val Leu
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Ser Asn Trp Phe Phe Glu Gln
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic peptide

<400> SEQUENCE: 43

Arg Val Ile Phe Phe Arg Leu Asn
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic peptide

<400> SEQUENCE: 44

Lys Ile Met Tyr Ile Arg Phe Asn
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic peptide

<400> SEQUENCE: 45

Pro Asp Phe Tyr Leu Gly Arg
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic peptide

<400> SEQUENCE: 46

Glu Tyr Gln Phe Val Thr Tyr Lys
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is D
<220> FEATURE:
<221> NAME/KEY: MISC_FEATURE
<222> LOCATION: (2)..(2)
<223> OTHER INFORMATION: X is E, F, W, or Y
<220> FEATURE:
<221> NAME/KEY: MISC_FEATURE
<222> LOCATION: (3)..(3)
<223> OTHER INFORMATION: X is G, D, M, or R
<220> FEATURE:
<221> NAME/KEY: MISC_FEATURE
<222> LOCATION: (4)..(4)
<223> OTHER INFORMATION: X is Y, F, W, L, or M
<220> FEATURE:
<221> NAME/KEY: MISC_FEATURE
<222> LOCATION: (5)..(5)
<223> OTHER INFORMATION: X is Y, M, L, A, F, or S
<220> FEATURE:
<221> NAME/KEY: MISC_FEATURE
<222> LOCATION: (6)..(6)
<223> OTHER INFORMATION: X is L, T, or R
<220> FEATURE:
<221> NAME/KEY: MISC_FEATURE
<222> LOCATION: (7)..(7)
<223> OTHER INFORMATION: X is Q or Y
<220> FEATURE:
<221> NAME/KEY: MISC_FEATURE
<222> LOCATION: (8)..(8)
<223> OTHER INFORMATION: X is H

<400> SEQUENCE: 47

Xaa Xaa Xaa Xaa Xaa Xaa Xaa Xaa
1               5

<210> SEQ ID NO 48
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is G, K, T, D, M, I, L, S, R, or a modified
    amino acid residue thereof
<220> FEATURE:
<221> NAME/KEY: MISC_FEATURE
<222> LOCATION: (2)..(2)
<223> OTHER INFORMATION: X is Y, F, A, W, L, Y, norleucine, M, or a
    modified amino acid residue thereof
<220> FEATURE:
<221> NAME/KEY: MISC_FEATURE
<222> LOCATION: (3)..(3)
<223> OTHER INFORMATION: X is Y, M, L, A, F, T, P, S, or a modified
    amino acid residue thereof
<220> FEATURE:
<221> NAME/KEY: MISC_FEATURE
<222> LOCATION: (4)..(4)
<223> OTHER INFORMATION: X is L, Y, G, A, T, R, or a modified amino acid
    residue thereof

<400> SEQUENCE: 48

Xaa Xaa Xaa Xaa

```
<210> SEQ ID NO 49
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is a natural or modified amino acid residue
      chosen from: D, A, V, N, P, F, H, I, E, M, W, K, and G
<220> FEATURE:
<221> NAME/KEY: MISC_FEATURE
<222> LOCATION: (2)..(2)
<223> OTHER INFORMATION: X is a natural or modified amino acid residue
      chosen from: E, F, G, M, K, A, K, L, and W
<220> FEATURE:
<221> NAME/KEY: MISC_FEATURE
<222> LOCATION: (3)..(3)
<223> OTHER INFORMATION: X is a natural or modified amino acid residue
      chosen from: G, F, K, D, M, T, I, Y, W, L, and R
<220> FEATURE:
<221> NAME/KEY: MISC_FEATURE
<222> LOCATION: (4)..(4)
<223> OTHER INFORMATION: X is a natural or modified amino acid residue
      chosen from: Y, A, S, F, W, L, T, and M
<220> FEATURE:
<221> NAME/KEY: MISC_FEATURE
<222> LOCATION: (5)..(5)
<223> OTHER INFORMATION: X is a natural or modified amino acid residue
      chosen from: Y, M, L, A, F, and S
<220> FEATURE:
<221> NAME/KEY: MISC_FEATURE
<222> LOCATION: (6)..(6)
<223> OTHER INFORMATION: X is a natural or modified amino acid residue
      chosen from: L, T, and R
<220> FEATURE:
<221> NAME/KEY: MISC_FEATURE
<222> LOCATION: (7)..(7)
<223> OTHER INFORMATION: X is a natural or modified amino acid residue
      chosen from: Q and Y

<400> SEQUENCE: 49

Xaa Xaa Xaa Xaa Xaa Xaa Xaa
1               5

<210> SEQ ID NO 50
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is a natural or modified amino acid residue
      chosen from: A, H, N, Q, G, F, K, D, M, T, I, Y, W, L,
      norleucine, and R
<220> FEATURE:
<221> NAME/KEY: MISC_FEATURE
<222> LOCATION: (2)..(2)
<223> OTHER INFORMATION: X is a natural or modified amino acid residue
      chosen from: D, E, Y, A, S, F, W, H, L, T, norleucine, and M
<220> FEATURE:
<221> NAME/KEY: MISC_FEATURE
<222> LOCATION: (3)..(3)
<223> OTHER INFORMATION: X is a natural or modified amino acid residue
      chosen from: Y, D, E, I, norleucine, M, L, A, F, and S
<220> FEATURE:
<221> NAME/KEY: MISC_FEATURE
<222> LOCATION: (4)..(4)
<223> OTHER INFORMATION: X is a natural or modified amino acid residue
      chosen from: L, V, H, Q, N, I, norleucine, Y, A, G, E, T, and R
```

```
<400> SEQUENCE: 50

Xaa Xaa Xaa Xaa
1

<210> SEQ ID NO 51
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is G, K, R, N, I, D, L, Q, T, M, norleucine,
      H, A, Y, or W
<220> FEATURE:
<221> NAME/KEY: MISC_FEATURE
<222> LOCATION: (2)..(2)
<223> OTHER INFORMATION: X is W, L, Y, F, D, E, norleucine, or M
<220> FEATURE:
<221> NAME/KEY: MISC_FEATURE
<222> LOCATION: (3)..(3)
<223> OTHER INFORMATION: X is A, F, L, Y, norleucine, M, I, S, W, or V
<220> FEATURE:
<221> NAME/KEY: MISC_FEATURE
<222> LOCATION: (4)..(4)
<223> OTHER INFORMATION: X is L, R, V, H, Q, N, I, norleucine, M, T, Y,
      A, G, or E

<400> SEQUENCE: 51

Xaa Xaa Xaa Xaa
1

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide

<400> SEQUENCE: 52

Glu Gly Trp Ala Leu Gln
1               5

<210> SEQ ID NO 53
<211> LENGTH: 4
<212> TYPE: PRT
<213> ORGANISM: Artificial Sequence
<220> FEATURE:
<223> OTHER INFORMATION: Synthetic peptide

<400> SEQUENCE: 53

Gly Trp Ala Leu
1

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide

<400> SEQUENCE: 54

Ser Tyr Tyr Ser Val Tyr Asp Leu Gly Asn Asn Arg
1               5                   10

<210> SEQ ID NO 55
<211> LENGTH: 8
<212> TYPE: PRT
```

```
<213> ORGANISM: Artificial Sequence
<220> FEATURE:
<223> OTHER INFORMATION: Synthetic peptide

<400> SEQUENCE: 55

Gly Leu Leu Gly Glu Phe Leu Arg
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide

<400> SEQUENCE: 56

Gln Phe Tyr Ser Val Phe Asp Arg
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic peptide

<400> SEQUENCE: 57

Ser Gln Leu Ser Glu Phe Trp Lys
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is a natural or modified amino acid residue
      chosen from: D, A, V, N, P, F, H, I E, M, W, K, and G
<220> FEATURE:
<221> NAME/KEY: MISC_FEATURE
<222> LOCATION: (2)..(2)
<223> OTHER INFORMATION: X is a natural or modified amino acid residue
      chosen from: E, F, G, N, M, K, A, K, L, and W
<220> FEATURE:
<221> NAME/KEY: MISC_FEATURE
<222> LOCATION: (3)..(3)
<223> OTHER INFORMATION: X is a natural or modified amino acid residue
      chosen from: G, F, K, D, M, T, I, N, Y, W, L, and R
<220> FEATURE:
<221> NAME/KEY: MISC_FEATURE
<222> LOCATION: (4)..(4)
<223> OTHER INFORMATION: X is a natural or modified amino acid residue
      chosen from: Y, A, S, F, N, W, L, T, and M
<220> FEATURE:
<221> NAME/KEY: MISC_FEATURE
<222> LOCATION: (5)..(5)
<223> OTHER INFORMATION: X is a natural or modified amino acid residue
      chosen from: Y, M, N, L, A, F, and S
<220> FEATURE:
<221> NAME/KEY: MISC_FEATURE
<222> LOCATION: (6)..(6)
<223> OTHER INFORMATION: X is a natural or modified amino acid residue
      chosen from: L, T, and R
<220> FEATURE:
<221> NAME/KEY: MISC_FEATURE
<222> LOCATION: (7)..(7)
<223> OTHER INFORMATION: X is a natural or modified amino acid residue
      chosen from: Q and Y
<220> FEATURE:
<221> NAME/KEY: MISC_FEATURE
```

-continued

```
<222> LOCATION: (8)..(8)
<223> OTHER INFORMATION: X is a natural or modified amino acid residue
      chosen from: H, M, L, K, N, G, and W

<400> SEQUENCE: 58

Xaa Xaa Xaa Xaa Xaa Xaa Xaa Xaa
1               5
```